US010124058B2

(12) United States Patent
Cheminay et al.

(10) Patent No.: US 10,124,058 B2
(45) Date of Patent: *Nov. 13, 2018

(54) RECOMBINANT MODIFIED VACCINIA VIRUS ANKARA (MVA) RESPIRATORY SYNCYTIAL VIRUS (RSV) VACCINE

(71) Applicant: Bavarian Nordic A/S, Kvistgaard (DK)

(72) Inventors: Cédric Cheminay, Munich (DE); Robin Steigerwald, Munich (DE); Paul Chaplin, Grafelfing (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/662,382

(22) Filed: Jul. 28, 2017

(65) Prior Publication Data

US 2017/0326228 A1    Nov. 16, 2017

Related U.S. Application Data

(60) Continuation of application No. 15/294,480, filed on Oct. 14, 2016, now Pat. No. 9,717,787, which is a division of application No. 14/417,779, filed as application No. PCT/EP2013/055483 on Mar. 5, 2013, now Pat. No. 9,480,738.

(60) Provisional application No. 61/678,367, filed on Aug. 1, 2012.

(51) Int. Cl.
| | |
|---|---|
| *A61K 39/00* | (2006.01) |
| *A61K 39/12* | (2006.01) |
| *C12N 15/86* | (2006.01) |
| *C12N 7/00* | (2006.01) |
| *A61K 39/285* | (2006.01) |
| *A61K 39/155* | (2006.01) |
| *C12Q 1/6851* | (2018.01) |
| *C07K 14/005* | (2006.01) |

(52) U.S. Cl.
CPC ............ *A61K 39/155* (2013.01); *A61K 39/12* (2013.01); *C07K 14/005* (2013.01); *C12N 7/00* (2013.01); *C12N 15/86* (2013.01); *C12Q 1/6851* (2013.01); *A61K 2039/5254* (2013.01); *A61K 2039/5256* (2013.01); *A61K 2039/543* (2013.01); *A61K 2039/57* (2013.01); *A61K 2039/575* (2013.01); *C07K 2319/00* (2013.01); *C12N 2710/24142* (2013.01); *C12N 2710/24143* (2013.01); *C12N 2710/24171* (2013.01); *C12N 2760/18534* (2013.01); *C12N 2760/18571* (2013.01)

(58) Field of Classification Search
CPC ........ C12N 7/00; C12N 15/86; C07K 14/005; A61K 2039/5254; A61K 39/12
See application file for complete search history.

(56) References Cited

FOREIGN PATENT DOCUMENTS

| WO | WO2007/007344 | * | 1/2007 |
| WO | WO2008/114149 | * | 9/2008 |

OTHER PUBLICATIONS

GenBank Sequence CAA26143.1, "unnamedprotein product" (Apr. 18, 2005).
Elango et al., Respiratory syncytial virus fusion glycoprotein: nucleotide sequence of mRNA, identification of cleavage activation site and amino acid sequence of N-terminus of F1 subunit, Nucleic Acids Research, 13: 1559-1574 (1985).

\* cited by examiner

*Primary Examiner* — Barry A Chestnut

(57) ABSTRACT

Provided herein are recombinant modified vaccinia virus Ankara (MVA) strains as improved vaccines against infection with Respiratory Syncytial Virus (RSV virus) and to related products, methods and uses. Specifically, provided herein are genetically engineered recombinant MVA vectors comprising at least one nucleotide sequence encoding an antigenic determinant of an RSV membrane glycoprotein and at least one nucleotide sequence encoding an antigenic determinant of an RSV nucleocapsid protein. Also provided herein are products, methods and uses thereof, e.g., suitable to affect an immune response in a subject, or suitable to diagnose an RSV infection, as well as to determine whether a subject is at risk of recurrent RSV infection.

18 Claims, 18 Drawing Sheets

Specification includes a Sequence Listing.

RECOMBINANT MODIFIED VACCINIA VIRUS ANKARA (MVA) RESPIRATORY SYNCYTIAL VIRUS (RSV) VACCINE

This application is a continuation application of U.S. application Ser. No. 15/294,480, now U.S. Pat. No. 9,717,787, which is a divisional application of U.S. application Ser. No. 14/417,779, now U.S. Pat. No. 9,480,738, which is a National Phase application under 35 U.S.C. § 371 of International Application No. PCT/EP2013/055483, filed Mar. 15, 2013, and claims the benefit under 35 U.S.C. § 365 of European Application 1200594.2 filed Aug. 1, 2012, and the benefit under 35 U.S.C. § 119(e) of U.S. Provisional Patent Application 61/678,367 filed Aug. 1, 2012, the disclosures of which are incorporated by reference herein in their entirety.

FIELD

The present invention relates to a recombinant modified vaccinia virus Ankara (MVA virus) as an improved vaccine against an infection with Respiratory Syncytial Virus (RSV virus) and to related products, methods and uses. Specifically, the present invention relates to a genetically engineered recombinant MVA vector comprising at least one nucleotide sequence encoding an antigenic determinant of an RSV membrane glycoprotein and at least one nucleotide sequence encoding an antigenic determinant of an RSV nucleocapsid protein. The invention also relates to products, methods and uses thereof, e.g., suitable to affect an immune response in a subject, or suitable to diagnose an RSV infection, as well as to determine whether a subject is at risk of recurrent RSV infection.

BACKGROUND

RSV is a significant respiratory pathogen. Acute lower respiratory tract (LRT) infection causes significant morbidity and mortality in infants and children under the age of five years worldwide [A. M. Aliyu et al. (2010), *Bayero J. Pure Appl. Sci.* 3(1):147-155]. Respiratory syncytial virus (RSV) is the most clinically important cause of LRT infection; primary infection with RSV generally occurs by age 2 [W. P. Glezen (1987), *Ped. Virol.* 2:1-4; Y. Murata (2009), *Clin. Lab. Med.* 29(4):725-739]. Because primary RSV infection does not induce complete immunity to RSV, frequent re-infections occur throughout life, with the most severe infections developing in the very young, the very old, and in immune-compromised patients of any age [Y. Murata (2009)].

As many of 40% of those infected with RSV eventually develop serious LRT disease requiring hospitalization, with the severity and intensity of the disease depending on the magnitude and intensity of infection and the host response [Aliyu et al. (2010)]. RSV can also cause serious LRT disease in patients of any age having compromised immune, respiratory, or cardiac systems, and may also predispose children to later development of asthma. In the United States alone, RSV causes an estimated 126,000 hospitalizations and 300 infant deaths a year [Y. Murata (2009)]. Furthermore, RSV accounts for more than 80,000 hospitalizations and more than 13,000 deaths each winter among elderly patients, and those with underlying cardiopulmonary or immunosuppressive conditions [Y. Murata (2009)]. Despite the importance of RSV as a respiratory pathogen, however, there is currently no safe and effective RSV vaccine on the market.

RSV is an enveloped RNA virus of the family Paramyxoviridae, subfamily Pneumovirinae [Aliyu et al. (2010)]. Each RSV virion contains a non-segmented, negative-sense, single-stranded RNA molecule of approximately 15,191 nucleotides containing ten genes encoding eleven separate proteins (M2 contains two open reading frames), including eight structural (G, F, SH, M1, N, P, M2.1, and L) and three non-structural proteins (NS1, NS2, and M2.2) [Y. Murata (2009)]. The genome is transcribed sequentially from NS1 to L, in the following order: 3'-NS1-NS2-N-P-M1-SH-G-F-M2.1-M2.2-L-5'.

The viral envelope contains three transmembrane glycoproteins (attachment glycoprotein (G), fusion glycoprotein (F), and small hydrophobic protein (SH)), as well as the matrix (M1) protein [Y. Murata (2009)]. During RSV replication, the virus first attaches to the target cell in a process mediated by the heavily glycosylated G protein. The virus then fuses with the host cell in a process mediated by the F protein, thereby penetrating the cell membrane and entering the host cell; the F protein is also required for the formation of the syncytia characteristic of RSV-infected cells. The attachment and fusion processes are augmented by SH protein. The M1 protein regulates the assembly of mature RSV by interacting with the envelope proteins F and G and with the nucleocapsid proteins N, P, and M2.1 (see below). Within the envelope, viral RNA is encapsidated by a transcriptase complex consisting of the nucleocapsid protein (N), phosphoprotein (P), transcription elongation factor (M2.1) and RNA polymerase (L) proteins [Y. Murata (2009)]. N associates with the genomic RNA, while P is a cofactor for L, the viral RNA polymerase. M2.1 is an elongation factor necessary for viral transcription, and M2.2 regulates transcription of the viral genome. Finally, NS1 and NS2 inhibit type I interferon activity.

Clinical RSV isolates are classified according to antigenic group (A or B) and further subdivided into multiple genotypes (e.g., A2 or $A_{Long}$ for the A group; and B1, CH-18537, or 8/60 for the B group) based on the genetic variability within the viral genome of each antigenic group [Y. Murata (2009)]. Classification is based on the reactivity of the viruses with monoclonal antibodies directed against the attachment glycoprotein (G protein) and by various genetic analyses. [M. Sato et al., *J. Clin. Microbiol.* 43(1):36-40 (2005)]. Among viral isolates, some RSV-encoded proteins are highly conserved at the level of amino acid sequence (e.g., F), while others vary extensively (e.g., G) between and within the two major antigenic groups [Y. Murata (2009)]. The F proteins from the A and B antigenic groups share considerable homology. In contrast, the G protein differs considerably between the two antigenic groups.

The G protein is the most variable RSV protein, with its hypervariable C-terminal region accounting for most of the strain-specific epitopes. The molecular epidemiology and evolutionary patterns of G protein have provided important information about the clinical and epidemiological features of RSV. Typically several different genotypes circulate at once, and the one that predominates in a community every year may change. However, the importance of strain diversity to the clinical and epidemiological features of RSV remains poorly understood. Recombinant RSV proteins are therefore accompanied by a strain designation to indicate the original RSV strain from which the gene or protein was cloned. For example, a cloned G protein from RSV strain $A_{Long}$ is designated $G(A_{Long})$, RSV $A_{Long}$ G, or RSV $A_{Long}$ G protein.

RSV stimulates a variety of immune responses in infected hosts, including the secretion of chemokines and cytokines, production of neutralizing humoral and mucosal antibodies, and production of CD4+ (e.g., $T_H1$ and $T_H2$) and CD8+ (e.g., CTL) T-cells. Such host immune responses are largely responsible for the clinical manifestations of RSV infection, since the virus causes limited cell cytopathology in vivo [Y. Murata (2009)]. The phenotypic manifestations and severity of RSV-induced disease are apparently mediated by the balance and interactions among the range of immune responses stimulated by RSV infection [Y. Murata (2009)].

Many previous studies suggest that the cellular and humoral immune responses play different roles in the induction of immunity to RSV and the resolution of RSV infection, as well as in disease progression [Y. Murata (2009) and references therein]. For example, studies with a humanized anti-F antibody showed that while anti-RSV antibodies are sufficient to prevent or limit the severity of infection, they are not required for clearing viral infection [Y. Murata (2009); A. F. G. Antonis et al. (2007), Vaccine 25:4818-4827]. In contrast, T-cell responses are necessary for clearing established RSV infections [Y. Murata (2009)]. The RSV-induced T-cell response also plays a key role in pulmonary pathology during infection. For example, interferon-γ (IFNγ)-secreting $T_H1$ cells—with or without an associated CD8+ CTL response—clear RSV with minimal lung pathology, while interleukin 4 (IL-4)-secreting $T_H2$ cells also clear RSV, but frequently accompanied by significant pulmonary changes, including eosinophilic infiltration, a hallmark of the enhanced disease observed during previous vaccine trials (see below).

Despite the abundance of information available regarding the immunology, virology, and physiology of RSV infection, however, it remains far from clear precisely what sort of immune response is likely to be most effective at inducing lasting immunity while also not producing enhanced disease on post-vaccination exposure to RSV, as discussed in more detail in the following sections.

Prior Vaccine Development

Vaccines typically use one of several strategies to induce protective immunity against a target infectious agent or pathogen (e.g., a virus, bacterium, or parasite), including: (1) inactivated pathogen preparations; (2) live attenuated pathogen preparations, including genetically attenuated pathogen strains; (3) purified protein subunit vaccine preparations; (4) viral vector-based vaccines encoding pathogen antigens and/or adjuvants; and (5) DNA-based vaccines encoding pathogen antigens.

Initial RSV vaccine development efforts focused on an inactivated virus preparation, until a clinical trial testing efficacy of a formalin-inactivated RSV (FI-RSV) vaccine was conducted in the United States during the 1960s with disastrous results [M. R. Olson & S. M. Varga (2007), J. Immunol. 179:5415-5424]. A significant number of vaccinated patients developed enhanced pulmonary disease characterized by eosinophil and neutrophil infiltrations and a substantial inflammatory response after subsequent natural infection with RSV Olson & Varga (2007), [Blanco J C et al. (2010) Hum Vaccin. 6:482-92]. Many of those patients required hospitalization and a few critically ill patients died. Consequently, investigators began searching for viral and/or host factors contributing to the development of enhanced disease after subsequent challenge in an effort to develop a safer RSV vaccine. That search has yielded much new information about RSV biology and the broad spectrum of immune responses it can induce, but a safe and effective RSV vaccine remains elusive.

Post-FI-RSV vaccine development efforts have focused in large part on single antigen vaccines using G, F, and, to a lesser extent, N or M2, with the viral antigens delivered either by viral or plasmid DNA vectors expressing the viral genes or as purified proteins. [See, e.g., W. Olszewska et al. (2004), Vaccine 23:215-221; G. Taylor et al. (1997), J. Gen. Virol. 78:3195-3206; and L. S. Wyatt et al. (2000), Vaccine 18:392-397]. Vaccination with a combination of F+G has also been tested in calves, cotton rats and BALB/c mice with varying results [Antonis et al. (2007) (calves); B. Moss, U.S. patent application Ser. No. 06/849,299 ('the '299 application'), filed Apr. 8, 1986 (cotton rats); and L. S. Wyatt et al. (2000) (BALB/c mice)]. Both F and G are immunogenic in calves, mice, cotton rats, humans, and to at least some degree in infant macaques [A. F. G. Antonis et al. (2007) (calves); B. Moss, the '299 application (cotton rats); L. de Waal et al. (2004), Vaccine 22:923-926 (infant macaques); L. S. Wyatt et al. (2000) (BALB/c mice); Y. Murata (2009) (humans)].

Significantly, however, the nature and type of immune response induced by RSV vaccine candidates varies—often quite considerably—depending on the type of vaccine used, the antigens selected, the route of administration, and even the model organism used. For example, immunization with live RSV or with replicating vectors encoding RSV F protein induces a dominant $T_H1$ response accompanied by production of neutralizing anti-F antibodies and CD8+ CTLs, both associated with minimal pulmonary pathology upon post-vaccination virus challenge [Y. Murata (2009) and references cited therein]. In contrast, immunization with an FI-inactivated RSV preparation induces a dominant $T_H2$ response completely lacking a CD8+ CTL response, which produces increased pathological changes in the lungs [Y. Murata (2009) and references cited therein]. Interestingly, the administration of RSV G protein as a purified subunit vaccine or in a replicating vector induces a dominant $T_H2$ response eventually producing eosinophilic pulmonary infiltrates and airway hyper-reactivity following post-vaccination virus challenge, a response very similar to the enhanced disease observed with FI-RSV [Y. Murata (2009) and references cited therein]. In addition, while vaccination with modified vaccinia virus Ankara (MVA) encoding RSV F protein induced anti-F antibodies and F-specific CD8+ T-cells in calves, vaccination with MVA-F+MVA-G induced anti-F and anti-G antibodies but no F- or G-specific CD8+ T-cells [A. F. G. Antonis et al. (2007)].

Vaccination of mice with vaccinia virus (VV) expressing F protein (VV-F) induced a strong CD8+ T-cell response which lead to clearance of replicating RSV from lung accompanied by a similar or greater weight loss than mice immunized with FI-RSV [W. Olszewska et al. (2004)]. However it was not related to the enhanced disease induced by FI-RSV or VV expressing G protein (VV-G) (combined $T_H2$ response lung eosinophilia and weight loss) resulting from enhanced secretion of $T_H2$ cytokines such as IL-4 and IL-5. Some in the field suggested that an RSV vaccine capable of inducing a relatively balanced immune response including both a cellular and a humoral component would be less likely to display enhanced immunopathology on post-vaccination challenge [W. Olszewska et al. (2004)].

However, while vaccination of BALB/c mice with modified vaccinia virus Ankara (MVA) encoding F, G, or F+G induced just such a balanced immune response, including both a humoral response (i.e., a balanced IgG1 and IgG2a response) and a $T_H1$ response (i.e., increased levels of IFNγ/interleukin-12 (IL-12) and decreased levels of interleukin-4 (IL-4)/interleukin-5 (IL-5)), vaccinated animals nevertheless still displayed some weight loss [W. Olszewska et al. (2004)].

Despite expending considerable effort to characterize the nature and extent of the immune responses induced by various vaccine candidates in several different model systems, it remains unclear precisely what sort of immune response is required to convey lasting and complete immunity to RSV without predisposing vaccine recipients to enhanced disease. Because of the marked imbalance between the clinical burden of RSV and the available therapeutic and prophylactic options, development of an RSV vaccine remains an unmet medical need.

Description

While prior unsuccessful efforts to develop an RSV vaccine focused primarily on vaccination with either RSV-F or RSV-G membrane glycoprotein or both, the present inventors have discovered that vaccination with a recombinant vaccinia virus Ankara (MVA) expressing at least one antigenic determinant of an RSV membrane glycoprotein and at least one antigenic determinant of an RSV nucleocapsid protein induces better protection. In addition, such constructs induce almost complete sterile immunity when applied by the intranasal route compared to subcutaneous application, or even when compared to the intramuscular route of administration used by Wyatt and colleagues [L. S. Wyatt et al. (2000)]. Enhanced protection can be obtained by administering candidate RSV vaccines intranasally in comparison to intramuscular administration.

With recombinant MVAs expressing either RSV F or RSV G membrane glycoprotein (or both) (e.g., MVA-mBN199B) or with recombinant MVAs expressing at least one antigenic determinant of an RSV membrane glycoprotein and at least one antigenic determinant of an RSV nucleocapsid protein (e.g., MVA-mBN201B), the present inventors observed no replicating RSV in the lung 4 days post-challenge, although RSV genomes were still detectable by RT-qPCR. Recombinant MVAs expressing at least one antigenic determinant of an RSV membrane glycoprotein and at least one antigenic determinant an RSV nucleocapsid protein (e.g., MVA-mBN201B) induced better protection and a larger decrease in the RSV viral load detectable by RT-qPCR because they induced a stronger CD8+ T cell response against the antigenic determinant of an RSV nucleocapsid protein. Administration of such recombinant viruses by the intranasal route furthermore induced almost complete sterile immunity (almost no RSV viral load detectable by RT-qPCR) because they induced the mucosal immune response and IgA antibody secretion, responses which were absent when such constructs were administered subcutaneously.

In contrast to FI-RSV, such constructs induce a balanced Th1-immune response generating good antibody responses, as well as strong, specific cellular immune responses to the RSV antigens. With intranasal administration of the vaccine producing IgG antibody levels even higher than those resulting from conventional subcutaneous administration in addition to the induction of a good IgA antibody response, protection is improved and body weight loss reduced. The magnitude of the cellular immune response was independent of the route of administration, however. Interestingly, the inventors observed a pattern of T-cell response induced by recombinant MVAs expressing at least one heterologous nucleotide sequence encoding an antigenic determinant of an RSV membrane glycoprotein and at least one heterologous nucleotide sequence encoding an antigenic determinant of an RSV nucleocapsid protein (e.g., MVA-mBN201B, expressing RSV F, G, N, and M2 proteins) that was similar to the T-cell response induced by RSV administrations, albeit much higher.

Thus, in a first aspect, the present invention provides a recombinant modified vaccinia virus Ankara (MVA) comprising at least one nucleotide sequence encoding an antigenic determinant of a respiratory syncytial virus (RSV) membrane glycoprotein and at least one nucleotide sequence encoding an antigenic determinant of an RSV nucleocapsid protein.

Modified Vaccinia Virus Ankara (MVA)

MVA has been generated by more than 570 serial passages on chicken embryo fibroblasts of the dermal vaccinia strain Ankara [Chorioallantois vaccinia virus Ankara virus, CVA; for review see Mayr et al. (1975), Infection 3, 6-14] that was maintained in the Vaccination Institute, Ankara, Turkey for many years and used as the basis for vaccination of humans. However, due to the often severe post-vaccinal complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells [Mayr et al. (1975)]. It was shown in a variety of animal models that the resulting MVA was avirulent [Mayr, A. & Danner, K. (1978), Dev. Biol. Stand. 41: 225-234]. As part of the early development of MVA as a pre-smallpox vaccine, there were clinical trials using MVA-517 in combination with Lister Elstree [Stickl (1974), Prev. Med. 3: 97-101; Stickl and Hochstein-Mintzel (1971), Munich Med. Wochenschr. 113: 1149-1153] in subjects at risk for adverse reactions from vaccinia. In 1976, MVA derived from MVA-571 seed stock (corresponding to the $571^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), *Zentralbl. Bacteriol.* (B) 167: 375-390). MVA-572 was deposited at the European Collection of Animal Cell Cultures as ECACC V94012707.

As a result of the passaging used to attenuate MVA, there are a number of different strains or isolates, depending on the passage number in CEF cells. For example, MVA-572 was used in Germany during the smallpox eradication program, and MVA-575 was extensively used as a veterinary vaccine. MVA-575 was deposited on Dec. 7, 2000, at the European Collection of Animal Cell Cultures (ECACC) with the deposition number V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells [Blanchard et al. (1998), J Gen Virol 79:1159-1167; Carroll & Moss (1997), Virology 238:198-211; U.S. Pat. No. 5,185,146; Ambrosini et al. (1999), J Neurosci Res 55: 569]. It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic: MVA was further passaged by Bavarian Nordic and is designated MVA-BN. MVA as well as MVA-BN lacks approximately 15% (31 kb from six regions) of the genome compared with ancestral CVA virus. The deletions affect a number of virulence and host range genes, as well as the gene for Type A inclusion bodies. A sample of MVA-BN corresponding to passage 583 was deposited on Aug. 30, 2000 at the European Collection of Cell Cultures (ECACC) under number V00083008.

MVA-BN can attach to and enter human cells where virally-encoded genes are expressed very efficiently. However, assembly and release of progeny virus does not occur. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome [E. Harrer et al. (2005), *Antivir. Ther.* 10(2):285-300; A. Cosma et al. (2003), *Vaccine* 22(1):21-9; M. Di Nicola et al. (2003), *Hum. Gene Ther.* 14(14):1347-1360; M. Di Nicola et al. (2004), *Clin. Cancer Res.*, 10(16):5381-5390].

"Derivatives" or "variants" of MVA refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat [Boukamp et al (1988), J Cell Biol 106: 761-771], the human bone osteosarcoma cell line 143B (ECACC No. 91112502), the human embryo kidney cell line 293 (ECACC No. 85120602), and the human cervix adenocarcinoma cell line HeLa (ATCC No. CCL-2). Additionally, a derivative or variant of MVA-BN has a virus amplification ratio at least two fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699), both incorporated herein by reference.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

In another aspect, an MVA viral strain suitable for generating the recombinant virus may be strain MVA-572, MVA-575 or any similarly attenuated MVA strain. Also suitable may be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see WO 2011/092029).

Definitions

The term "antigenic determinant" refers to any molecule that stimulates a host's immune system to make an antigen-specific immune response, whether a cellular response and/or a humoral antibody response. Antigenic determinants may include proteins, polypeptides, antigenic protein fragments, antigens, and epitopes which still elicit an immune response in a host and form part of an antigen, homologue or variant of proteins, polypeptides, and antigenic protein fragments, antigens and epitopes including, for example, glycosylated proteins, polypeptides, antigenic protein fragments, antigens and epitopes, and nucleotide sequences encoding such molecules. Thus, proteins, polypeptides, antigenic protein fragments, antigens and epitopes are not limited to particular native nucleotide or amino acid sequences but encompass sequences identical to the native sequence as well as modifications to the native sequence, such as deletions, additions, insertions and substitutions.

Preferably, such homologues or variants have at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% identity with the referenced protein, polypeptide, antigenic protein fragment, antigen and epitope at the level of nucleotide or amino acid sequence. The term homologue or variant also encompasses truncated, deleted or otherwise modified nucleotide or protein sequences such as, for example, (1) RSV-F or RSV-G nucleotide sequences encoding soluble forms of the corresponding RSV-F or RSV-G proteins lacking the signal peptide as well as the transmembrane and/or cytoplasmic domains of the full-length RSV-F or RSV-G proteins, (2) RSV-M2 or RSV-N nucleotide sequences encoding deleted, truncated or otherwise mutated versions of the full-length RSV-M2 or RSV-N proteins, (3) soluble forms of the RSV-F or RSV-G proteins lacking the signal peptide as well as the transmembrane and/or cytoplasmic domains of the full-length RSV-F or RSV-G proteins, or (4) deleted, truncated or otherwise mutated versions of the full-length RSV-M2 or RSV-N proteins.

Techniques for determining sequence identity between nucleic acids and amino acids are known in the art. Two or more sequences can be compared by determining their "percent identity." The percent identity of two sequences, whether nucleic acid or amino acid sequences, is the number of exact matches between two aligned sequences divided by the length of the shorter sequences and multiplied by 100.

"Percent (%) amino acid sequence identity" with respect to proteins, polypeptides, antigenic protein fragments, antigens and epitopes described herein is defined as the percentage of amino acid residues in a candidate sequence that are identical with the amino acid residues in the reference sequence (i.e., the protein, polypeptide, antigenic protein fragment, antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

The same applies to "percent (%) nucleotide sequence identity", mutatis mutandis.

For example, an appropriate alignment for nucleic acid sequences is provided by the local homology algorithm of Smith and Waterman, (1981), *Advances in Applied Mathematics* 2:482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), *Nucl. Acids Res.* 14(6):6745-6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://http://blast.ncbi.nlm.nih.gov/.

As used herein, a "heterologous" gene, nucleic acid, antigen, or protein is understood to be a nucleic acid or amino acid sequence which is not present in the wild-type poxviral genome (e.g., MVA). The skilled person understands that a "heterologous gene", when present in a poxvirus such as MVA, is to be incorporated into the poxviral genome in such a way that, following administration of the recombinant poxvirus to a host cell, it is expressed as the corresponding heterologous gene product, i.e., as the "heterologous antigen" and\or "heterologous protein." Expression is normally achieved by operatively linking the heterologous gene to regulatory elements that allow expression in the poxvirus-infected cell. Preferably, the regulatory elements include a natural or synthetic poxviral promoter.

"Sterile immunity" as used herein means protective immunity in the absence of detectable RSV genome when sensitive detection methods, such as RT-qPCR, are applied.

It must be noted that, as used herein, the singular forms "a", "an", and "the", include plural references unless the context clearly indicates otherwise. Thus, for example, reference to "an epitope" includes one or more of epitopes and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), though less preferred, whenever used herein in the context of an aspect or embodiment of the present invention can be substituted with the term "consisting of".

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

RSV Nucleotide Sequences and Proteins

The RSV genes as mentioned herein refer to the genes, or to a homologue or variant of the genes, encoding the corresponding protein in any RSV strain or isolate, even though the exact sequence and/or genomic location of the gene may differ between strains or isolates.

Likewise, the RSV proteins mentioned herein refer to proteins, or to a homologue or variant of the proteins, encoded and expressed by the corresponding protein gene as defined above.

By way of example, as used interchangeably herein, the terms "F protein gene", "F glycoprotein gene", "RSV F protein gene", "RSV F glycoprotein gene" or "F gene" refer to the gene, or to a homologue or variant of the gene, encoding the transmembrane fusion glycoprotein in any RSV strain or isolate, even though the exact sequence and/or genomic location of the F protein gene may differ between strains or isolates. For example, in the A2 strain of RSV, the F(A2) protein gene comprises nucleotides 5601-7499 (endpoints included) as numbered in GenBank Accession Number M11486. The F(A2) protein gene further comprises a protein coding open reading frame (ORF) spanning nucleotides 5614-7338 (endpoints included) as numbered in GenBank Accession No. M11486. The nucleotide sequence of the F protein gene from RSV A2 is set forth in SEQ ID NO:28.

Also interchangeably used herein are the terms "F protein", "F glycoprotein", "RSV F protein", "RSV F glycoprotein", or "F" which refer to the heavily glycosylated transmembrane fusion glycoprotein, or to a homologue or variant of the protein, encoded and expressed by an RSV F protein gene as defined above. The amino acid sequence of the F protein from RSV A2 is set forth in SEQ ID NO:29. The RSV(A2) F protein comprises a signal peptide, an extracellular domain, a transmembrane domain, and a cytoplasmic domain (see, e.g., UniProtKB/Swiss-Prot Accession No. P03420). The signal peptide of RSV A2 F protein consists of amino acids 1-21 of SEQ ID NO:29; the extracellular domain of RSV A2 F protein consists of amino acids 1-529 of SEQ ID NO:29 or amino acids 22-529 of SEQ ID NO:29; the transmembrane domain of RSV A2 F protein consists of amino acids 530-550 of SEQ ID NO:29; and the cytoplasmic domain of RSV A2 F protein consists of amino acids 551-574 of SEQ ID NO:29.

Likewise, also the terms "G protein gene", "G glycoprotein gene", "RSV G protein gene", "RSV G glycoprotein gene" or "G gene" are used interchangeably herein. For example, in the A2 strain of RSV, the G(A2) protein gene comprises nucleotides 4626-5543 (endpoints included) as numbered in GenBank Accession Number M11486. The G(A2) protein gene further comprises a protein coding open reading frame (ORF) spanning nucleotides 4641-5537 (endpoints included) as numbered in GenBank Accession No. M11486. The nucleotide sequence of the G protein gene from RSV A2 is set forth in SEQ ID NO:30.

The terms "G protein", "G glycoprotein", "RSV G protein", "RSV G glycoprotein", or "G" refer to the heavily glycosylated transmembrane attachment glycoprotein, or to a homologue or variant of the protein. The amino acid sequence of the G protein from RSV A2 is set forth in SEQ ID NO:31. RSV A2 G protein comprises an extracellular domain, a transmembrane domain, and a cytoplasmic domain (see, e.g., UniProtKB/Swiss-Prot Accession No. P03423). The extracellular domain of RSV A2 G protein consists of amino acids 67-298 of SEQ ID NO:31; the transmembrane domain of RSV A2 G protein consists of amino acids 38-66 of SEQ ID NO:31; and the cytoplasmic domain of RSV A2 G protein consists of amino acids 1-37 of SEQ ID NO:31.

Interchangeably used herein are also the terms "M2 protein gene", "M2 nucleocapsid protein gene", "RSV M2 protein gene", "RSV M2 matrix protein gene", "RSV M2 nucleocapsid protein gene" or "M2 gene". For example, in the A2 strain of RSV, the M2(A2) protein gene comprises nucleotides 7550-8506 (endpoints included) as numbered in GenBank Accession Number M11486. The M2(A2) protein gene further comprises a protein coding open reading frame (ORF) spanning nucleotides 7559-8143 (endpoints included) as numbered in GenBank Accession No. M11486. The nucleotide sequence of the M2 protein gene from RSV A2 is set forth in SEQ ID NO:32.

Used interchangeably herein are the terms "M2 protein", "M2 nucleocapsid protein", "RSV M2 protein", "RSV M2 nucleocapsid protein", "RSV M2 matrix protein", or "M2". The amino acid sequence of the M2 protein from RSV A2 is set forth in SEQ ID NO:33 (see, e.g., UniProtKB/Swiss-Prot Accession No. P04545).

Also, the terms "N protein gene", "N nucleocapsid protein gene", "RSV N protein gene", "RSV N nucleocapsid protein gene" or "N gene" may be used interchangeably herein. For example, in the A2 strain of RSV, the N(A2) protein gene comprises nucleotides 1081-2277 (endpoints included) as numbered in GenBank Accession Number M11486. The N(A2) protein gene further comprises a protein coding open reading frame (ORF) spanning nucleotides 1096-2271 (endpoints included) as numbered in GenBank Accession No. M11486. The nucleotide sequence of the N protein gene from RSV A2 is set forth in SEQ ID NO:34.

The amino acid sequence of the "N protein", "N nucleocapsid protein", "RSV N protein", "RSV N nucleocapsid protein", or "N", terms which are interchangeably used herein, from RSV A2 is set forth in SEQ ID NO:35 (see, e.g., UniProtKB/Swiss-Prot Accession No. P03418).

Certain Embodiments of the Invention

In certain embodiments, the recombinant MVA expresses at least one heterologous nucleotide sequence encoding an antigenic determinant of an RSV membrane glycoprotein. In certain embodiments, the at least one heterologous nucleotide sequence encoding an antigenic determinant of an RSV membrane glycoprotein encodes an RSV F antigenic determinant. In certain embodiments, the at least one heterologous nucleotide sequence encoding an antigenic determinant of an RSV membrane glycoprotein encodes an RSV G antigenic determinant. In certain embodiments, the RSV F antigenic determinant is derived from RSV strain A2. In certain embodiments, the RSV G antigenic determinant is derived from RSV strain A2.

In certain embodiments, the recombinant MVA comprises two heterologous nucleotide sequences, each encoding an antigenic determinant of an RSV membrane glycoprotein. In certain embodiments, the first antigenic determinant of an RSV membrane glycoprotein is an RSV F antigenic determinant and the second antigenic determinant of an RSV membrane glycoprotein is an RSV G antigenic determinant. In certain embodiments, the RSV F antigenic determinant is derived from RSV strain A2. In certain embodiments, the RSV G antigenic determinant is derived from RSV strain A2. In certain embodiments, both the RSV F antigenic determinant and the RSV G antigenic determinant can be derived from RSV strain A2.

In certain embodiments, the recombinant MVA expresses at least one heterologous nucleotide sequence encoding an antigenic determinant of an RSV membrane glycoprotein and at least one heterologous nucleotide sequence encoding an antigenic determinant of an RSV nucleocapsid protein. In certain embodiments, the at least one heterologous nucleotide sequence encoding an antigenic determinant of an RSV membrane glycoprotein encodes an RSV F antigenic determinant and the at least one heterologous nucleotide sequence encoding an antigenic determinant of an RSV nucleocapsid protein encodes an RSV M2 antigenic determinant. In certain embodiments, the at least one heterologous nucleotide sequence encoding an antigenic determinant of an RSV membrane glycoprotein encodes an RSV F antigenic determinant and the at least one heterologous nucleotide sequence encoding an antigenic determinant of an RSV nucleocapsid protein encodes an RSV N antigenic determinant. In certain embodiments, the at least one heterologous nucleotide sequence encoding an antigenic determinant of an RSV membrane glycoprotein encodes an RSV G antigenic determinant and the at least one heterologous nucleotide sequence encoding an antigenic determinant of an RSV nucleocapsid protein encodes an RSV M2 antigenic determinant. In certain embodiments, the at least one heterologous nucleotide sequence encoding an antigenic determinant of an RSV membrane glycoprotein encodes an RSV G antigenic determinant and the at least one heterologous nucleotide sequence encoding an antigenic determinant of an RSV nucleocapsid protein encodes an RSV N antigenic determinant.

In certain embodiments, the recombinant MVA comprises two heterologous nucleotide sequences, each encoding an antigenic determinant of an RSV membrane glycoprotein. In certain embodiments, the first antigenic determinant of an RSV membrane glycoprotein is an RSV F antigenic determinant and the second antigenic determinant of an RSV membrane glycoprotein is an RSV G antigenic determinant. In certain embodiments, the recombinant MVA comprises two heterologous nucleotide sequences, each encoding an antigenic determinant of an RSV membrane glycoprotein and at least one heterologous nucleotide sequence encoding an antigenic determinant of an RSV nucleocapsid protein. In certain embodiments, the first antigenic determinant of an RSV membrane glycoprotein is an RSV F antigenic determinant, the second antigenic determinant of an RSV membrane glycoprotein is an RSV G antigenic determinant, and the antigenic determinant of an RSV nucleocapsid protein is an RSV M2 antigenic determinant. In certain embodiments, the first antigenic determinant of an RSV membrane glycoprotein is an RSV F antigenic determinant, the second antigenic determinant of an RSV membrane glycoprotein is an RSV G antigenic determinant, and the antigenic determinant of an RSV nucleocapsid protein is an RSV N antigenic determinant. In certain embodiments, both the RSV F antigenic determinant and the RSV G antigenic determinant can be derived from RSV strain A2.

In certain embodiments, the recombinant MVA comprises two heterologous nucleotide sequences, each encoding an antigenic determinant of an RSV membrane glycoprotein and two heterologous nucleotide sequences, each encoding an antigenic determinant of an RSV nucleocapsid protein. In certain embodiments, the first antigenic determinant of an RSV membrane glycoprotein is an RSV F antigenic determinant, the second antigenic determinant of an RSV membrane glycoprotein is an RSV G antigenic determinant, the first antigenic determinant of an RSV nucleocapsid protein is an RSV M2 antigenic determinant, and the second antigenic determinant of an RSV nucleocapsid protein is an RSV N antigenic determinant. In certain embodiments, both the RSV F antigenic determinant and the RSV G antigenic determinant are derived from RSV strain A2.

In certain embodiments, the recombinant MVA comprises three heterologous nucleotide sequences, each encoding an antigenic determinant of an RSV membrane glycoprotein and two heterologous nucleotide sequences, each encoding an antigenic determinant of an RSV nucleocapsid protein. In certain embodiments, the first antigenic determinant of an RSV membrane glycoprotein is an RSV F antigenic determinant and the second antigenic determinant of an RSV membrane glycoprotein is an RSV G antigenic determinant, the first antigenic determinant of an RSV nucleocapsid protein is an RSV M2 antigenic determinant, and the second antigenic determinant of an RSV nucleocapsid protein is an RSV N antigenic determinant. In certain embodiments, both the first antigenic determinant of an RSV membrane glycoprotein and the second antigenic determinant of an RSV membrane glycoprotein are derived from RSV strain A2. In certain embodiments, the third antigenic determinant of an RSV membrane glycoprotein is an RSV F antigenic determinant.

In certain embodiments, the recombinant MVA comprises four heterologous nucleotide sequences, each encoding an antigenic determinant of an RSV membrane glycoprotein and two heterologous nucleotide sequences, each encoding an antigenic determinant of an RSV nucleocapsid protein. In certain embodiments, the first antigenic determinant of an RSV membrane glycoprotein is an RSV F antigenic determinant and the second antigenic determinant of an RSV membrane glycoprotein is an RSV G antigenic determinant, the first antigenic determinant of an RSV nucleocapsid protein is an RSV M2 antigenic determinant, and the second antigenic determinant of an RSV nucleocapsid protein is an RSV N antigenic determinant. In certain embodiments, both the first antigenic determinant of an RSV membrane glycoprotein and the second antigenic determinant of an RSV membrane glycoprotein are derived from RSV strain A2. In certain embodiments, the third antigenic determinant of an RSV membrane glycoprotein is an RSV F antigenic determinant. In certain embodiments, the fourth antigenic determinant of an RSV membrane glycoprotein is an RSV G antigenic determinant.

In certain embodiments, the at least one heterologous nucleotide sequence encoding an antigenic determinant of an RSV membrane glycoprotein encodes an RSV F antigenic determinant. In certain embodiments, the RSV F antigenic determinant is full-length. In certain embodiments, the RSV F antigenic determinant is truncated. In certain embodiments, the RSV F antigenic determinant is a variant RSV F antigenic determinant. In certain embodiments, the full-length, truncated or variant RSV F antigenic determinant is derived from RSV strain A2. In certain embodiments, the full-length RSV(A2) F antigenic determinant comprises the nucleotide sequence of SEQ ID NO:28 encoding the amino acid sequence of SEQ ID NO:29. In certain embodiments, the variant RSV(A2) F antigenic determinant comprises the nucleotide sequence of SEQ ID NO:3 encoding the amino acid sequence of SEQ ID NO:4. In certain embodiments, the truncated RSV(A2) F antigenic determinant lacks the cytoplasmic and transmembrane domains of the full-length RSV(A2) F antigenic determinant. In certain embodiments, the truncated RSV(A2) F antigenic determinant comprises the nucleotide sequence of SEQ ID NO:15 encoding the amino acid sequence of SEQ ID NO:16. In certain embodiments, the full-length, truncated or variant RSV F antigenic determinant is derived from RSV strain ALong. In certain embodiments, the variant RSV(ALong) F antigenic determinant comprises the nucleotide sequence of SEQ ID NO:5 encoding the amino acid sequence of SEQ ID NO:6. In certain embodiments, the truncated RSV(ALong) F antigenic determinant lacks the cytoplasmic and transmembrane domains of the full-length RSV(ALong) F antigenic determinant.

In certain embodiments, the at least one heterologous nucleotide sequence encoding an antigenic determinant of an RSV membrane glycoprotein encodes an RSV G antigenic determinant. In certain embodiments, the RSV G antigenic determinant is full-length. In certain embodiments, the RSV G antigenic determinant is truncated. In certain embodiments, the RSV G antigenic determinant is a variant RSV G antigenic determinant. In certain embodiments, the full-length, truncated or variant RSV G antigenic determinant is derived from RSV strain A2. In certain embodiments, the full-length RSV(A2) G antigenic determinant comprises the nucleotide sequence of SEQ ID NO:1 encoding the amino acid sequence of SEQ ID NO:2. In certain embodiments, the truncated RSV(A2) G antigenic determinant lacks the cytoplasmic and transmembrane domains of the full-length RSV(A2) G antigenic determinant. In certain embodiments, the full-length, truncated or variant RSV G antigenic determinant is derived from RSV strain B. In certain embodiments, the truncated RSV(B) G antigenic determinant lacks the cytoplasmic and transmembrane domains of the full-length RSV(B) G antigenic determinant. In certain embodiments, the truncated RSV(B) G antigenic determinant comprises the nucleotide sequence of SEQ ID NO:7 encoding the amino acid sequence of SEQ ID NO:8.

In certain embodiments, the at least one heterologous nucleotide sequence encoding an antigenic determinant of an RSV nucleocapsid protein encodes an RSV M2 antigenic determinant. In certain embodiments, the RSV M2 antigenic determinant is full-length. In certain embodiments, the RSV M2 antigenic determinant is truncated. In certain embodiments, the RSV M2 antigenic determinant is a variant RSV M2 antigenic determinant. In certain embodiments, the full-length, truncated or variant RSV M2 antigenic determinant is derived from RSV strain A2. In certain embodiments, the RSV(A2) M2 antigenic determinant comprises the nucleotide sequence of SEQ ID NO:32, encoding the amino acid sequence of SEQ ID NO:33.

In certain embodiments, the at least one heterologous nucleotide sequence encoding an antigenic determinant of an RSV nucleocapsid protein encodes an RSV N antigenic determinant. In certain embodiments, the RSV N antigenic determinant is full-length. In certain embodiments, the RSV N antigenic determinant is truncated. In certain embodiments, the RSV N antigenic determinant is a variant RSV N antigenic determinant. In certain embodiments, the full-length, truncated or variant RSV N antigenic determinant is derived from RSV strain A2. In certain embodiments, the RSV(A2) N antigenic determinant comprises the nucleotide sequence of SEQ ID NO:34, encoding the amino acid sequence of SEQ ID NO:35.

In certain embodiments, both the RSV N antigenic determinant and the RSV M2 antigenic determinant are encoded by a single open reading frame and separated by a self-cleaving protease domain. In certain embodiments, the RSV M2 antigenic determinant is full-length. In certain embodiments, the RSV M2 antigenic determinant is truncated. In certain embodiments, the RSV M2 antigenic determinant is a variant RSV M2 antigenic determinant. In certain embodiments, the full-length, truncated or variant RSV M2 antigenic determinant is derived from RSV strain A2. In certain embodiments, the RSV N antigenic determinant is full-length. In certain embodiments, the RSV N antigenic determinant is truncated. In certain embodiments, the RSV N antigenic determinant is a variant RSV N antigenic determinant. In certain embodiments, the full-length, truncated or variant RSV N antigenic determinant is derived from RSV strain A2. In certain embodiments, the self-cleaving protease domain is derived from Foot and Mouth Disease Virus. In certain embodiments, the self-cleaving protease domain is the protease 2A fragment from Foot and Mouth Disease Virus, comprising the nucleotide sequence of SEQ ID NO:11, encoding the amino acid sequence of SEQ ID NO:12. In certain embodiments, the at least one heterologous nucleotide sequence encoding an RSV N antigenic determinant and an RSV M2 antigenic determinant comprises the nucleotide sequence of SEQ ID NO:17, encoding the amino acid sequence of SEQ ID NO:18.

Integration Sites into MVA

In certain embodiments, the heterologous nucleotide sequences encoding one or more antigenic determinants of RSV membrane glycoproteins and one or more antigenic determinants of RSV nucleocapsid proteins are incorporated in a variety of insertion sites in the MVA genome, or in the MVA-BN genome. The heterologous nucleotide sequences encoding one or more antigenic determinants RSV proteins can be inserted into the recombinant MVA as separate transcriptional units or as fusion genes, as depicted in FIG. 1.

In certain embodiments, the heterologous RSV nucleotide sequences are inserted into one or more intergenic regions (IGR) of the MVA. The IGR may be selected from IGR07/08, IGR 44/45, IGR 64/65, IGR 88/89, IGR 136/137, and IGR 148/149, preferably from IGR64/65, IGR88/89, and/or IGR 148/149. The heterologous RSV nucleotide sequences may be, additionally or alternatively, inserted into one or more of the naturally occurring deletion sites I, II, II, IV, V, or VI of the MVA. In certain embodiments, less than 5, 4, 3, or 2 of the integration sites comprise heterologous RSV nucleotide sequences.

The number of insertion sites of MVA comprising heterologous RSV nucleotide sequences can be 1, 2, 3, 4, 5, 6, 7, or more. The recombinant MVA can comprise heterologous RSV nucleotide sequences inserted into 4, 3, 2, or fewer insertion sites, but preferably two insertion sites are used. In certain embodiments, three insertion sites are used. Preferably, the recombinant MVA comprises at least 4, 5, 6, or 7 nucleotide sequences inserted into 2 or 3 insertion sites.

The recombinant MVA viruses provided herein can be generated by routine methods known in the art. Methods to obtain recombinant poxviruses or to insert heterologous nucleotide sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) [J. Sambrook et al., Cold Spring Harbor Laboratory Press (1989)], and techniques for the handling and manipulation of viruses are described in Virology Methods Manual [B. W. J. Mahy et al. (eds.), Academic Press (1996)]. Similarly, techniques and know-how for the handling, manipulation and genetic engineering of MVA are described in Molecular Virology: A Practical Approach [A. J. Davison & R. M. Elliott (Eds.), The Practical Approach Series, IRL Press at Oxford University Press, Oxford, UK (1993) (see, e.g., Chapter 9: Expression of genes by Vaccinia virus vectors)] and Current Protocols in Molecular Biology [John Wiley &

Son, Inc. (1998) (see, e.g., Chapter 16, Section IV: Expression of proteins in mammalian cells using vaccinia viral vector)].

For the generation of the various recombinant MVAs disclosed herein, different methods may be applicable. The nucleotide sequences to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign gene or genes. In case, this gene can be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, coinfect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

Expression of RSV genes

In one embodiment, expression of one, more, or all of the heterologous RSV nucleotide sequences is under the control of one or more poxvirus promoters. In certain embodiments, the poxvirus promoter is a Pr7.5 promoter, a hybrid early/late promoter, a PrS promoter, a synthetic or natural early or late promoter, or a cowpox virus ATI promoter. In certain embodiments, the poxvirus promoter is selected from the group consisting of the PrS promoter (SEQ ID NO:39), the Pr7.5 promoter (SEQ ID NO:40), the PrSynIIm promoter (SEQ ID NO:41), the PrLE1 promoter (SEQ ID NO:42), and the PrH5m promoter (SEQ ID NO:43 [L. S. Wyatt et al. (1996), *Vaccine* 14(15):1451-1458]). In certain embodiments, the poxvirus promoter is the PrS promoter (SEQ ID NO:39). In certain embodiments, the poxvirus promoter is the Pr7.5 promoter (SEQ ID NO:40). In certain embodiments, the poxvirus promoter is the PrSynIIm promoter (SEQ ID NO:41). In certain embodiments, the poxvirus promoter is the PrLE1 promoter (SEQ ID NO:42). In certain embodiments, the poxvirus promoter is the PrH5m promoter (SEQ ID NO:43).

A heterologous RSV nucleotide sequence or sequences can be expressed as a single transcriptional unit. For example, a heterologous RSV nucleotide sequence can be operably linked to a vaccinia virus promoter and/or linked to a vaccinia virus transcriptional terminator. In certain embodiments, one or more heterologous RSV nucleotide sequences are expressed as a fusion protein. The fusion protein can further comprise a recognition site for a peptidase or a heterologous self-cleaving peptide sequence. The heterologous self-cleaving peptide sequence may be the 2A peptidase from Foot and Mouth Disease Virus.

In certain embodiments, the "transcriptional unit" is inserted by itself into an insertion site in the MVA genome, but may also be inserted with other transcriptional unit(s) into an insertion site in the MVA genome. The "transcriptional unit" is not naturally occurring (i.e., it is heterologous, exogenous or foreign) in the MVA genome and is capable of transcription in infected cells.

Preferably, the recombinant MVA comprises 1, 2, 3, 4, 5, or more transcriptional units inserted into the MVA genome. In certain embodiments, the recombinant MVA stably expresses RSV proteins encoded by 1, 2, 3, 4, 5, or more transcriptional units. In certain embodiments, the recombinant MVA comprises 2, 3, 4, 5, or more transcriptional units inserted into the MVA genome at 1, 2, 3, or more insertion sites in the MVA genome.

RSV Vaccines and Pharmaceutical Compositions

Since the recombinant MVA viruses, including MVA-BN, described herein are highly replication restricted and, thus, highly attenuated, they are ideal candidates for the treatment of a wide range of mammals including humans and even immune-compromised humans. Hence, provided herein are the recombinant MVAs according to the present invention for use as active pharmaceutical substances as well as pharmaceutical compositions and vaccines, all intended for inducing an immune response in a living animal body, including a human.

For this, the recombinant MVA, vaccine or pharmaceutical composition can be formulated in solution in a concentration range of $10^4$ to $10^9$ TCID$_{50}$/ml, $10^5$ to $5 \times 10^8$ TCID$_{50}$/ml, $10^6$ to $10^8$ TCID$_{50}$/ml, or $10^7$ to $10^8$ TCID$_{50}$/ml. A preferred dose for humans comprises between $10^6$ to $10^9$ TCID$_{50}$, including a dose of $10^6$ TCID$_{50}$, $10^7$ TCID$_{50}$, $10^8$ TCID$_{50}$ or $5\times10^8$ TCID$_{50}$.

The pharmaceutical compositions provided herein may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the recombinant MVA viruses provided herein can be converted into a physiologically acceptable form. This can be done based on experience in the preparation of poxvirus vaccines used for vaccination against smallpox as described by H. Stickl et al., *Dtsch. med. Wschr.* 99:2386-2392 (1974).

For example, purified viruses can be stored at $-80°$ C. with a titer of $5\times10^8$ TCID$_{50}$/ml formulated in about 10 mM Tris, 140 mM NaCl pH 7.7. For the preparation of vaccine shots, e.g., $10^2$-$10^8$ or $10^2$-$10^9$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. The glass ampoule is then sealed and can be stored between $4°$ C. and room temperature for several months. However, as long as no need exists, the ampoule is stored preferably at temperatures below $-20°$ C.

For vaccination or therapy, the lyophilisate can be dissolved in an aqueous solution, preferably physiological saline or Tris buffer, and administered either systemically or locally, i.e., parenteral, subcutaneous, intravenous, intramuscular, intranasal, or any other path of administration known to the skilled practitioner. The mode of administration, the dose and the number of administrations can be optimized by those skilled in the art in a known manner. However, most commonly a patient is vaccinated with a second shot about one month to six weeks after the first vaccination shot.

Kits Comprising Recombinant MVA Viruses

Also provided herein are kits comprising any one or more of the recombinant MVAs described herein. The kit can comprise one or multiple containers or vials of the recombinant MVA, together with instructions for the administration of the recombinant MVA to a subject at risk of RSV infection. In certain embodiments, the subject is a human. The instructions may indicate that the recombinant MVA is administered to the subject in a single dose, or in multiple (i.e., 2, 3, 4, etc.) doses. In certain embodiments, the instructions indicate that the recombinant MVA virus is administered in a first (priming) and second (boosting) administration to naïve or non-naïve subjects.

Further provided is a kit comprising the recombinant MVA virus in a first vial or container for a first administration (priming) and in a second vial or container for a second administration (boosting). The kit may also comprise the recombinant MVA in a third, fourth or further vial or container for a third, fourth or further administration (boosting).

Methods and Uses of Recombinant MVA Viruses

Also provided herein are methods of immunizing a subject animal, as well as recombinant MVAs for use in methods of immunizing a subject animal and use of the recombinant MVAs provided herein in the preparation of a medicament or vaccine for immunizing a subject animal. In certain embodiments, the animal is a mammal. In certain embodiments, the mammal is a rat, rabbit, pig, mouse, or human, and the methods comprise administering a dose of any one or more of the recombinant MVAs provided herein to the subject.

The subject is preferably a human and may be an adult, wherein the adult may be immune-compromised. In certain embodiments, the adult is over the age of 50, 55, 60, 65, 70, 75, 80, or 85 years. In other embodiments, the subject's age is less than 5 years, less than 3 years, less than 2 years, less than 15 months, less than 12 months, less than 9 months, less than 6, or less than 3 months. The subject's age may also range from 0-3 months, 3-6 months, 6-9 months, 9-12 months, 1-2 years, or 2-5 years.

In certain embodiments, any of the recombinant MVAs provided herein are administered to the subject at a dose of $10^6$ to $10^9$ TCID$_{50}$, at a dose of $10^6$ to $5\times10^8$ TCID$_{50}$, or $10^7$ to $10^8$ TCID$_{50}$. The recombinant MVAs provided herein may also be administered to the subject at a dose of $10^6$, $10^7$ TCID$_{50}$, $10^8$, or $5\times10^8$ TCID$_{50}$. In certain embodiments, any of the recombinant MVAs provided herein are administered to a human subject at a dose of $10^7$ TCID$_{50}$, $10^8$, or $5\times10^8$ TCID$_{50}$.

The recombinant MVAs provided herein are administered to the subject in a single dose, or in multiple (i.e., 2, 3, 4, etc.) doses. In certain embodiments, the recombinant MVAs are administered in a first (priming) and second (boosting) administration. In certain embodiments, the first dose comprises $10^7$ to $10^8$ TCID$_{50}$ of recombinant MVA virus and the second dose comprises $10^7$ to $10^8$ TCID$_{50}$ of recombinant MVA virus.

The recombinant MVAs can be administered systemically or locally, parenterally, subcutaneously, intravenously, intramuscularly, or intranasally, preferably subcutaneously or intranasally. The recombinant MVAs can also be administered by any other path of administration known to the skilled practitioner In another aspect, provided herein are methods of diagnosing RSV infection and methods of determining whether a subject is at risk of recurrent RSV infection, which may be a severe threat, particularly for newborn infants, children between 1 and 6 years old, and/or the elderly.

The present inventors have found that current methods of diagnosing an RSV infection may provide incorrect results. For example, an immunoassay detecting antibodies against RSV or a viral plaque assay may not necessarily accurately identify individuals at risk of a recurrent infection. Indeed, the present inventors observed that even though a sample taken from an individual may return a negative result in a viral plaque assay [see, e.g., W. Olszewska et al., 2004.], such results can sometimes be false negatives, since more sensitive methods sometimes demonstrate that infectious RSV particles are still present. In fact, methods such as quantitative real time-polymerase chain reaction (qRT-PCR) are required to confirm whether a subject may actually be infected with RSV, is at risk of recurrent infection, or indeed, whether a vaccinated subject has acquired sterile immunity to RSV. This determination may be critical, because reinfection following vaccination sometimes causes enhanced disease, occasionally resulting in death.

Accordingly, in certain embodiments, provided herein are methods of determining whether a subject is at risk of recurrent RSV infection, comprising quantitatively determining whether a sample obtained from the subject contains RSV genomes, wherein the presence of RSV genomes indicates the likelihood of a recurrent infection with RSV. In certain embodiments, the quantitative determination of whether a sample obtained from a subject contains RSV genomes is performed by qRT-PCR.

As used herein, the term "sample" refers to any biological sample obtained from an individual, cell line, tissue culture, or other source containing polynucleotides and polypeptides or portions thereof. Biological samples include body fluids (such as, for example, blood, serum, plasma, urine, synovial fluid, spinal fluid, bronchoalveolar lavage (BAL)) and body tissues found and/or suspected to contain RSV, including clinical samples obtained, for example, from subjects participating in a clinical trial or other experimental study. Methods for obtaining tissue biopsies and body fluids from mammals are well-known in the art. In certain embodiments, the biological sample includes RSV nucleic acids.

As used interchangeably herein, the terms "RT-qPCR" or "qRT-PCR" refer to a method known as "quantitative real time polymerase chain reaction." In some cases, this method may also be referred to as kinetic polymerase chain reaction (KPCR).

In certain embodiments, provided herein are methods of determining whether a subject has acquired sterile immunity against RSV, comprising quantitatively determining whether a sample obtained from the subject contains RSV genomes, wherein the presence of RSV genomes indicates that the subject has not acquired sterile immunity against RSV. Also provided herein are methods of immunizing a subject that has not acquired sterile immunity against RSV, comprising intranasally administering any one of the recombinant MVAs described herein to the subject. Additionally or alternatively, any one of the recombinant MVAs described herein is provided for use in methods of immunizing a subject that has not acquired sterile immunity against RSV, the method comprising intranasally administering any one of the recombinant MVAs described herein to the subject. Provided herein is also the use of any of the recombinant MVAs described herein in the preparation of a medicament and/or vaccine for immunizing a subject that has not acquired sterile immunity against RSV, wherein the medicament or vaccine is administered intranasally.

In certain embodiments, provided herein are methods of inducing sterile immunity against RSV in a subject that has not acquired sterile immunity against RSV, comprising intranasally administering any of the recombinant MVAs described herein to the subject. Also provided herein is any one of the recombinant MVAs described herein for use in methods of inducing sterile immunity against RSV in a subject that has not acquired sterile immunity against RSV, the methods comprising intranasally administering any one of the recombinant MVAs described herein to the subject. Additionally or alternatively, provided herein is the use of any of the recombinant MVAs described herein in the preparation of a medicament and/or vaccine for inducing sterile immunity against RSV in a subject that has not acquired sterile immunity against RSV, wherein the medicament or vaccine is administered intranasally.

Certain embodiments of the present invention also include the following items:

1. A recombinant modified vaccinia virus Ankara (MVA) comprising a nucleotide sequence encoding an antigenic determinant of at least one respiratory syncytial virus (RSV) membrane glycoprotein for treating or preventing an RSV infection by intranasal administration, wherein an intramuscular administration is excluded.
2. Use of a recombinant modified vaccinia virus Ankara (MVA) comprising a nucleotide sequence encoding an antigenic determinant of at least one respiratory syncytial virus (RSV) membrane glycoprotein for the preparation of a pharmaceutical composition and/or vaccine, wherein the pharmaceutical composition and/or vaccine is administered intranasally and wherein an intramuscular administration is excluded.
3. A method of immunizing a subject, including a human, against RSV infection, comprising intranasally administering a recombinant modified vaccinia virus Ankara (MVA) comprising a nucleotide sequence encoding at least one antigenic determinant of a respiratory syncytial virus (RSV) membrane glycoprotein to the subject, including the human, wherein an intramuscular administration is excluded.
4. The recombinant MVA of item 1, the use of item 2 and/or the method of item 3 comprising solely intranasal administration.
5. The recombinant MVA of item 1, the use of item 2 and/or the method of item 3 comprising subcutaneous administration.
6. The recombinant MVA of any one of items 1 or 4 to 5, the use of any one of items 2, 4 or 5 and/or the method of any one of items 3 to 5, wherein the recombinant MVA further comprises a nucleotide sequence encoding an antigenic determinant of an RSV nucleocapsid protein.
7. A recombinant modified vaccinia virus Ankara (MVA) comprising at least one nucleotide sequence encoding an antigenic determinant of a respiratory syncytial virus (RSV) membrane glycoprotein and at least one nucleotide sequence encoding an RSV nucleocapsid antigenic determinant.
8. The recombinant MVA, the use and/or method of any one of items 1 to 7, wherein the nucleotide sequence encoding an antigenic determinant of the RSV membrane glycoprotein encodes an RSV F antigenic determinant.
9. The recombinant MVA, the use and/or method of any one of items 1 to 8 further comprising at least one nucleotide sequence encoding an antigenic determinant of an RSV F membrane glycoprotein.
10. The recombinant MVA, the use and/or method of any one of items 1 to 9, wherein the nucleotide sequence encoding an antigenic determinant of the RSV membrane glycoprotein encodes a full length RSV F membrane glycoprotein.
11. The recombinant MVA, the use and/or method of any one of items 8 to 10, wherein the nucleotide sequence encoding an antigenic determinant of the RSV F membrane glycoprotein is derived from RSV strain A, preferably from A2 and/or $A_{long}$.
12. The recombinant MVA, the use and/or method of any one of items 8 to 11, wherein the nucleotide sequence encoding an antigenic determinant of the RSV F membrane glycoprotein comprises a nucleotide sequence encoding the amino acid sequence of SEQ ID NO:4.
13. The recombinant MVA, the use and/or method of any one of items 8 to 12, wherein the nucleotide sequence sequence encoding an antigenic determinant of an RSV F membrane glycoprotein comprises the nucleotide sequence SEQ ID NO:3.
14. The recombinant MVA, the use and/or method of any one of items 1 to 13, wherein the nucleotide sequence encoding an antigenic determinant of the RSV membrane glycoprotein encodes a truncated RSV F membrane glycoprotein.
15. The recombinant MVA, the use and/or method of item 14, wherein the nucleotide sequence encoding the truncated RSV F membrane glycoprotein is derived from RSV strain A, preferably from $A_{long}$.
16. The recombinant MVA, the use and/or method of item 14 or 15, wherein the truncated RSV F membrane glycoprotein lacks the transmembrane domain.
17. The recombinant MVA, the use and/or method of any one of items 14 to 16, wherein the truncated RSV F membrane glycoprotein lacks the cytoplasmic domain.
18. The recombinant MVA, the use and/or method of any one of items 8 to 17, wherein the nucleotide sequence encoding an antigenic determinant of the RSV F membrane glycoprotein comprises a nucleotide sequence encoding the amino acid sequence of SEQ ID NO:6.
19. The recombinant MVA, the use and/or method of any one of items 8 to 18, wherein the nucleotide sequence encoding an antigenic determinant of the RSV F membrane glycoprotein comprises the nucleotide sequence of SEQ ID NO:5.
20. The recombinant MVA, the use and/or method of any of the preceding items, wherein the nucleotide sequence encoding an antigenic determinant of the RSV membrane glycoprotein encodes an antigenic determinant of the RSV G membrane glycoprotein.
21. The recombinant MVA, the use and/or method of any one of items 1 to 20 further comprising at least one nucleotide sequence encoding an antigenic determinant of an RSV G membrane glycoprotein.
22. The recombinant MVA, the use and/or method of any one of item 1 to 21, wherein the nucleotide sequence encoding an antigenic determinant of the RSV membrane glycoprotein encodes a full length RSV G membrane glycoprotein.
23. The recombinant MVA, the use and/or method of any one of items 20 to 22, wherein the nucleotide sequence encoding an antigenic determinant of the RSV G membrane glycoprotein is derived from RSV strain A, preferably from strain A2, and/or B.
24. The recombinant MVA, the use and/or method of any one of items 20 to 23, wherein the nucleotide sequence encoding an antigenic determinant of the RSV G membrane glycoprotein comprises a nucleotide sequence encoding the amino acid sequence of SEQ ID NO:2.
25. The recombinant MVA, the use and/or method of any one of items 20 to 24, wherein the nucleotide sequence encoding an antigenic determinant of the RSV G membrane glycoprotein comprises the nucleotide sequence SEQ ID NO:1.
26. The recombinant MVA, the use and/or method of any one of items 1 to 25 wherein the nucleotide sequence encoding an antigenic determinant of the RSV membrane glycoprotein encodes a truncated RSV G membrane glycoprotein.
27. The recombinant MVA, the use and/or method of item 26, wherein the nucleotide sequence encoding an antigenic determinant of a truncated RSV G membrane glycoprotein is derived from RSV strain B.
28. The recombinant MVA, the use and/or method of item 26 or 27, wherein the truncated RSV G membrane glycoprotein lacks the transmembrane domain.
29. The recombinant MVA, the use and/or method of any one of items 26 to 28, wherein the truncated RSV G membrane glycoprotein lacks the cytoplasmic domain.
30. The recombinant MVA, the use and/or method of any one of items 20 to 29, wherein the nucleotide sequence encoding an antigenic determinant of the RSV G membrane glycoprotein comprises a nucleotide sequence encoding the amino acid sequence of SEQ ID NO:8.
31. The recombinant MVA, the use and/or method of any one of items 20 to 30, wherein the nucleotide sequence encoding an antigenic determinant of the RSV G membrane glycoprotein comprises the nucleotide sequence of SEQ ID NO:7.
32. The recombinant MVA, the use and/or method of any one of items 6 to 31, wherein the nucleotide sequence encoding an antigenic determinant of an RSV nucleocapsid protein encodes an antigenic determinant of the RSV N nucleocapsid protein.
33. The recombinant MVA, the use and/or method of any of one of items 6 to 32, wherein the nucleotide sequence encoding an antigenic determinant of an RSV nucleocapsid protein encodes an antigenic determinant of an RSV M2 matrix protein.
34. The recombinant MVA, the use and/or method of any one of items 6 to 33, wherein the nucleotide sequence encoding an antigenic determinant of an RSV nucleocapsid protein encodes a full length protein.
35. The recombinant MVA, the use and/or method of any one of items 32 to 34, wherein the nucleotide sequence encoding an antigenic determinant of the RSV N nucleocapsid protein is derived from RSV strain A, preferably strain A2.
36. The recombinant MVA, the use and/or method of any one of items 32 to 35, wherein the nucleotide sequence encoding an antigenic determinant of an RSV nucleocapsid protein encodes antigenic determinants of both the RSV N nucleocapsid and RSV M2 matrix proteins.
37. The recombinant MVA, the use and/or method of item 36, wherein both the antigenic determinants of the RSV N nucleocapsid and of the RSV M2 matrix proteins are encoded by a single open reading frame.
38. The recombinant MVA, the use and/or method of item 36 or 37, wherein the antigenic determinants of the RSV N nucleocapsid and of the RSV M2 matrix proteins are separated by a self-cleaving protease domain.
39. The recombinant MVA, the use and/or method of item 38, wherein the self-cleaving protease domain sequence is derived from Foot and Mouth Disease Virus.
40. The recombinant MVA, the use and/or method of item 38 or 39, wherein the self-cleaving protease domain sequence is the protease 2A fragment sequence.
41. The recombinant MVA, the use and/or method of any one items 38 to 40, wherein the self-cleaving protease domain sequence comprises a nucleotide sequence encoding the amino acid sequence of SEQ ID NO:12.
42. The recombinant MVA, the use and/or method of any one of items 38 to 41, wherein the self-cleaving protease domain comprises the nucleotide sequence of SEQ ID NO:11.
43. The recombinant MVA, the use and/or method of any one of items 37 to 42, wherein the single open reading frame comprises a nucleotide sequence encoding the amino acid sequence of SEQ ID NO:18.
44. The recombinant MVA, the use and/or method of any one of items 37 to 43, wherein the single open reading frame comprises the nucleotide sequence of SEQ ID NO:17.
45. The recombinant MVA, the use and/or method of any of the preceding items comprising one nucleotide sequence encoding an antigenic determinant of an RSV membrane glycoprotein and one nucleotide sequence encoding an antigenic determinant of an RSV nucleocapsid protein.
46. The recombinant MVA, the use and/or method of item 45 comprising antigenic determinants of the RSV F membrane glycoprotein and of the RSV N nucleocapsid protein.
47. The recombinant MVA, the use and/or method of item 45 comprising antigenic determinants of the RSV F membrane glycoprotein and of the RSV M2 matrix protein.
48. The recombinant MVA, the use and/or method of item 45 comprising antigenic determinants of the RSV G membrane glycoprotein and of the RSV N nucleocapsid protein.
49. The recombinant MVA, the use and/or method of item 45 comprising antigenic determinants of the RSV G membrane glycoprotein and of the RSV M2 matrix protein.
50. The recombinant MVA, the use and/or method of any one of items 1 to 44 comprising two nucleotide sequences encoding an antigenic determinant of an RSV membrane glycoprotein and one nucleotide sequence encoding an antigenic determinant of an RSV nucleocapsid protein.
51. The recombinant MVA, the use and/or method of item 50 comprising antigenic determinants of the RSV F and/or of the G membrane glycoproteins and of the RSV N nucleocapsid protein.
52. The recombinant MVA, the use and/or method of item 50 comprising antigenic determinants of the RSV F and/or of the G membrane glycoproteins and of the RSV M2 matrix protein.
53. The recombinant MVA, the use and/or method of any one of items 1 to 44 comprising two nucleotide sequences encoding antigenic determinants of an RSV membrane glycoprotein and two nucleotide sequences encoding antigenic determinants of an RSV nucleocapsid protein.
54. The recombinant MVA, the use and/or method of item 53 comprising nucleotide sequences encoding antigenic determinants of an RSV F and/or of a G membrane glycoprotein and antigenic determinants of an RSV N nucleocapsid and/or of an M2 matrix protein.
55. The recombinant MVA, the use and/or method of any one of items 1 to 44 comprising three nucleotide sequences encoding an antigenic determinant of an RSV membrane glycoprotein and two nucleotide sequences encoding antigenic determinants of an RSV nucleocapsid protein.
56. The recombinant MVA, the use and/or method of item 55 comprising antigenic determinants of two RSV F membrane glycoproteins and/or of one RSV G membrane glycoprotein and an antigenic determinant of the RSV N nucleocapsid protein and/or of the RSV M2 matrix protein.
57. The recombinant MVA, the use and/or method of item 55 comprising antigenic determinants of two RSV G membrane glycoproteins and/or of one RSV F membrane glycoprotein and an antigenic determinant of the RSV N nucleocapsid protein and/or of the RSV M2 matrix protein.
58. The recombinant MVA, the use and/or method of any one of items 1 to 44 comprising four nucleotide sequences encoding antigenic determinants of RSV membrane glycoproteins and one nucleotide sequence encoding an antigenic determinant of an RSV nucleocapsid protein.
59. The recombinant MVA, the use and/or method of item 58 comprising antigenic determinants of two RSV F membrane glycoproteins and/or two RSV G membrane glycoproteins and an antigenic determinant of the RSV N nucleocapsid protein or of the RSV M2 matrix protein.
60. The recombinant MVA, the use and/or method of any one of items 1 to 44 comprising four nucleotide sequences encoding antigenic determinants of RSV membrane glycoproteins and two nucleotide sequences encoding antigenic determinants of RSV nucleocapsid proteins.
61. The recombinant MVA, the use and/or method of item 60 comprising antigenic determinants of two RSV F membrane glycoproteins and/or of two RSV G membrane glycoproteins and antigenic determinants of the RSV N nucleocapsid protein and/or of the RSV M2 matrix proteins.
62. The recombinant MVA, the use and/or method of any one of items 1 to 61, wherein the MVA used for generating the recombinant MVA is MVA-BN or a derivative thereof.
63. The recombinant MVA of any one of items 1 or 4 to 62 for use as an active pharmaceutical substance.
64. A pharmaceutical composition and/or vaccine comprising the recombinant MVA of any one of items 1 or 4 to 63 and, optionally, a pharmaceutically acceptable carrier and/or diluent.
65. Use of the recombinant MVA of any one of items 1 or 4 to 63 for the preparation of a pharmaceutical composition and/or vaccine.
66. The recombinant MVA of any one of items 6 to 63, the pharmaceutical composition and/or vaccine of item 64 and/or the use of any one of items 2, 4 to 6, 8 to 62 or 65 for treating or preventing an RSV infection.
67. A method of immunizing a subject, including a human, against RSV infection, comprising administering the recombinant MVA of any one of items 1, 4 to 63 or 66 and/or the pharmaceutical composition and/or vaccine according to item 64 or 66 to the subject, including the human.
68. The recombinant MVA of any one of items 1, 4 to 63 or 66, the pharmaceutical composition and/or vaccine of item 64 or 66, the use of any one of items 2, 4 to 6, 8 to 62, 65 or 66 and/or the method of any one of items 3 to 6, 8 to 62 or 67, wherein the recombinant MVA is or is to be administered in a dose of between $10^7$-$10^9$ $TCID_{50}$.
69. The recombinant MVA, the pharmaceutical composition and/or vaccine, the use and/or the method of any one of items 5 to 68, wherein the recombinant MVA is or is to be administered intranasally and/or subcutaneously.
70. The recombinant MVA, the pharmaceutical composition and/or vaccine, the use and/or the method of any one of items 1 to 69, wherein the recombinant MVA is or is to be administered in a single or multiple doses to an immunologically naïve or an immunologically experienced subject, including a human.
71. The recombinant MVA, the pharmaceutical composition and/or vaccine, the use and/or the method of any one of items 1 to 70 for administering to a subject, including the human, with more than 2 years of age.
72. The recombinant MVA, the pharmaceutical composition and/or vaccine, the use and/or the method of any one of items 1 to 70 for administering to a subject, including the human, with less than 2 years of age.
73. A kit comprising one or multiple vials of the recombinant MVA of any one of items 1, 4 to 63, 66 or 68 to 72 and instructions for the administration of the virus to a subject at risk of RSV infection.
74. A kit comprising the recombinant MVA according to any one of items 1, 4 to 63, 66 or 68 to 72 and/or the kit according to item 73, comprising the recombinant MVA in a first vial or container for a first administration (priming) and in a second vial or container for a second administration (boosting).

75. The kit according to item 73 or 74, comprising the recombinant MVA in a third, fourth or further vial or container for a third, fourth or further administration (boosting).

76. A cell comprising the recombinant MVA according to any one of items 1, 4 to 63 or 66.

77. A method of generating a recombinant MVA according to any one of items 1, 4 to 63, 66 or 68 to 72, comprising the steps of:
(a) infecting a host cell with an MVA virus,
(b) transfecting the infected cell with a recombinant vector comprising a nucleotide sequence encoding an RSV antigenic determinant, said nucleotide sequence further comprising a genomic MVA virus sequence capable of directing the integration of the nucleotide sequence into the MVA virus genome,
(c) identifying, isolating and, optionally, purifying the generated recombinant MVA virus.

78. A recombinant MVA generated according to the method of item 77.

79. A method for producing a recombinant MVA according to any one items 1, 4 to 63, 66 or 68 to 72 and/or for producing an antigenic determinant expressed from the genome of said recombinant MVA comprising the steps of:
(a) infecting a host cell with the recombinant MVA of any one of items 1, 4 to 63, 66 or of items 68 to 72, or transfecting the cell with the recombinant DNA of the recombinant MVA,
(b) cultivating the infected or transfected cell,
(c) isolating the MVA and/or antigenic determinant from said cell.

80. A recombinant MVA and/or antigenic determinant obtainable by the method of item 79.

81. A method for determining whether a subject is at risk of recurrent RSV infection, comprising determining by means of RT-qPCR whether in a sample obtained from the subject RSV is present, whereby the presence of RSV indicates the presence of a recurrent RSV infection.

82. A method for determining whether a subject has acquired sterile immunity against RSV, comprising determining by means of RT-qPCR whether in a sample obtained from the subject RSV is present, whereby the presence of RSV indicates that the subject has not acquired sterile immunity against RSV.

83. A method of immunizing a subject diagnosed by the method of item 82 to not have acquired sterile immunity against RSV, comprising intranasally administering the recombinant MVA of any one of items 1, 4 to 63, 66, 68 to 72, 78 or 80 and/or the pharmaceutical composition and/or vaccine of any one of items 64, 66 or 68 to 72 to the subject.

84. The recombinant MVA of any one of items 1, 4 to 63, 66, 68 to 72, 78 or 80 and/or the pharmaceutical composition and/or vaccine of any one of items 64, 66 or 68 to 72 for use in a method of immunizing a subject diagnosed by the method of item 82 to not have acquired sterile immunity against RSV, said method comprising intranasally administering said recombinant MVA to the subject.

85. Use of the recombinant MVA of any one of items 1, 4 to 63, 66, 68 to 72, 78 or 80 for the preparation of a pharmaceutical composition and/or vaccine for immunizing a subject diagnosed by the method of item 82 to not have acquired sterile immunity against RSV, wherein the pharmaceutical composition and/or vaccine is for intranasal administration.

86. A method of inducing sterile immunity in a subject diagnosed by the method of item 82 to not have acquired sterile immunity against RSV, comprising intranasally administering the recombinant MVA of any one of items 1, 4 to 63, 66, 68 to 72, 78 or 80 and/or the pharmaceutical composition and/or vaccine of any one of items 64, 66 or 68 to 72 to the subject.

87. The recombinant MVA of any one of items 1, 4 to 63, 66, 68 to 72, 78 or 80 and/or the pharmaceutical composition and/or vaccine of any one of items 64, 66 or 68 to 72 for use in a method of inducing sterile immunity in a subject diagnosed by the method of item 82 to not have acquired sterile immunity against RSV, said method comprising intranasally administering said recombinant MVA to the subject.

88. Use of the recombinant MVA of any one of items 1, 4 to 63, 66, 68 to 72, 78 or 80 for the preparation of a pharmaceutical composition and/or vaccine for inducing sterile immunity in a subject diagnosed by the method of item 82 to not have acquired sterile immunity against RSV, wherein the pharmaceutical composition or vaccine is for intranasal administration.

It is to be understood that both the foregoing general and detailed description are exemplary and explanatory only and do not restrict or limit the invention as claimed. The accompanying drawings, which are incorporated in and constitute a part of this specification, illustrate various embodiments of the invention and together with the description, serve to explain the principles of the invention.

BRIEF DESCRIPTION OF THE SEQUENCES

Figure 1:
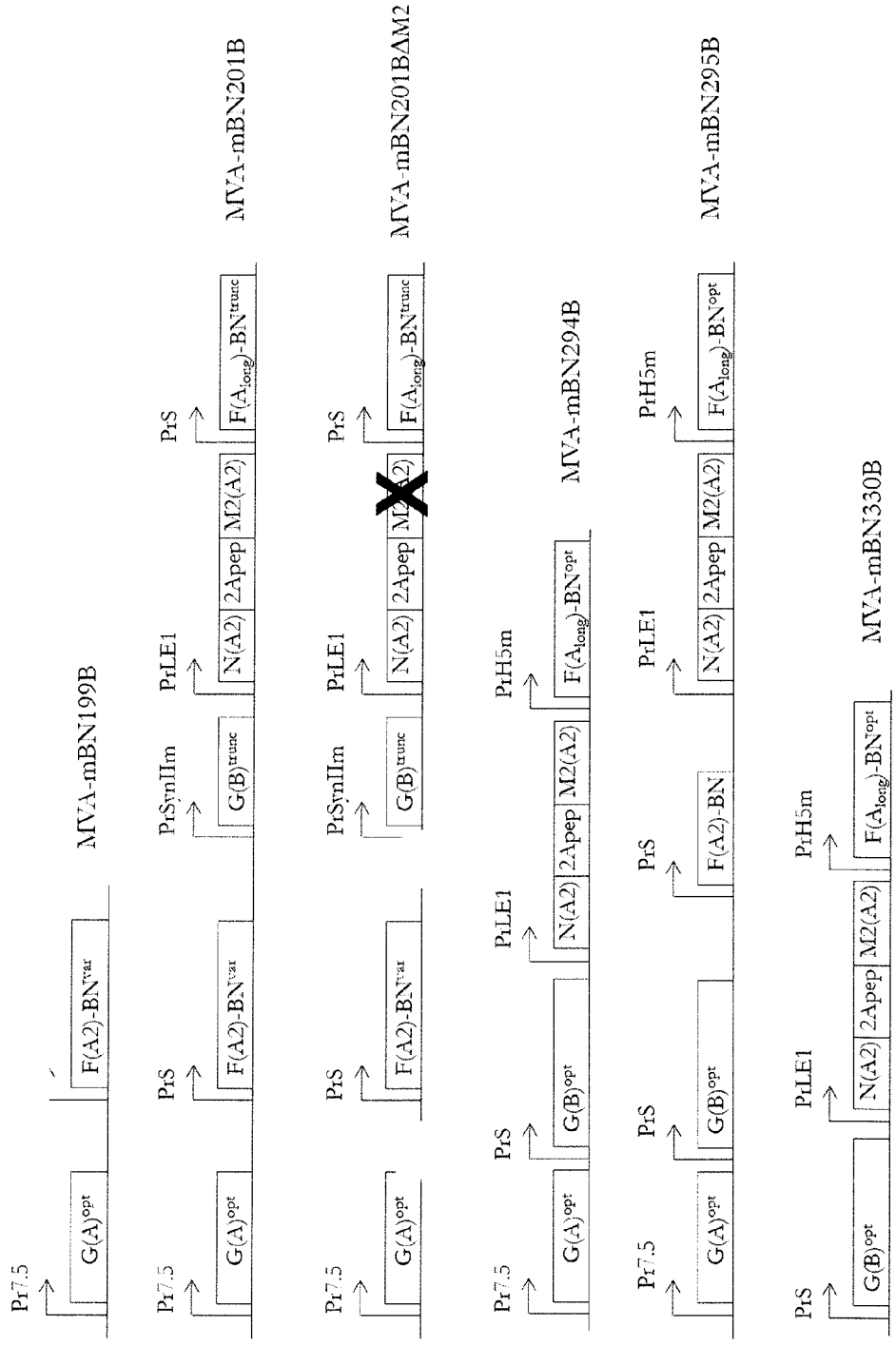
FIG. 1 shows the heterologous RSV genes used in the tested recombinant MVA-constructs, MVA-mBN199B, MVA-mBN201B, MVA-mBN201BΔM2, MVA-mBN294B, MVA-mBN295B and MVA-mBN330B.

SEQ ID NO:1 is a DNA sequence encoding full-length G protein from human RSV (hRSV) strain A2 (GenBank Accession No. M11486).

SEQ ID NO:2 is the amino acid sequence of full-length G protein from hRSV strain A2 (GenBank Accession No. M11486).

SEQ ID NO:3 is a DNA sequence encoding full-length F protein (BN variant) from hRSV strain A2.

SEQ ID NO:4 is the amino acid sequence of full-length F protein (BN variant) from hRSV strain A2.

SEQ ID NO:5 is a DNA sequence encoding full-length F protein (BN variant) from hRSV strain ALong.

SEQ ID NO:6 is the amino acid sequence encoding full-length F protein (BN variant) from hRSV strain ALong.

SEQ ID NO:7 is a DNA sequence encoding truncated G protein lacking the transmembrane and cytoplasmic domains from hRSV strain B (GenBank Accession No. P20896).

SEQ ID NO:8 is the amino acid sequence of truncated G protein lacking the transmembrane and cytoplasmic domains from hRSV strain B (GenBank Accession No. P20896).

SEQ ID NO:9 is a DNA sequence encoding N protein lacking a stop codon from hRSV strain A2 (Genbank Accession No. M11486).

SEQ ID NO:10 is the amino acid sequence of N protein lacking a stop codon from hRSV strain A2 (Genbank Accession No. M11486).

SEQ ID NO:11 is a DNA sequence encoding a fragment of protease 2A from Foot and Mouth Disease Virus lacking both start and stop codons.

SEQ ID NO:12 is the amino acid sequence of a fragment of protease 2A from Foot and Mouth Disease Virus lacking both start and stop codons.

SEQ ID NO:13 is a DNA sequence encoding full-length M2 protein lacking a start codon from hRSV strain A2 (GenBank Accession No. M11486).

SEQ ID NO:14 is the amino acid sequence encoding full-length M2 protein lacking a start codon from hRSV strain A2 (GenBank Accession No. M11486).

SEQ ID NO:15 is a DNA sequence encoding truncated F protein lacking the transmembrane and cytoplasmic domains (BN variant) from hRSV strain A2 (GenBank Accession No. M11486).

SEQ ID NO:16 is the amino acid sequence of truncated F protein lacking the transmembrane and cytoplasmic domains (BN variant) from hRSV strain A2 (GenBank Accession No. M11486).

SEQ ID NO:17 is a DNA sequence encoding N protein lacking a stop codon hRSV strain A2 (Genbank Accession No. M11486)+a DNA sequence encoding protease 2A fragment from Foot and Mouth Disease Virus, lacking both a start codon and a stop codon+a DNA sequence encoding full-length M2 protein lacking a start codon from hRSV strain A2 (GenBank Accession No. M11486).

SEQ ID NO:18 is the amino acid sequence of N protein from hRSV strain A2 (Genbank Accession No. M11486)+the amino acid sequence of protease 2A fragment from Foot and Mouth Disease Virus, lacking a start codon+the amino acid sequence of full-length M2 protein lacking a start codon from hRSV strain A2 (GenBank Accession No. M11486).

SEQ ID NO:19 is the amino acid sequence of RSV-1 peptide derived from RSV F protein.

SEQ ID NO:20 is the amino acid sequence of RSV-2 peptide derived from RSV F protein.

SEQ ID NO:21 is the amino acid sequence of RSV-3 peptide derived from RSV F protein.

SEQ ID NO:22 is the amino acid sequence of RSV-4 peptide derived from RSV G protein.

SEQ ID NO:23 is the amino acid sequence of RSV-5 peptide derived from RSV G protein.

SEQ ID NO:24 is the amino acid sequence of RSV-6 peptide derived from RSV G protein.

SEQ ID NO:25 is the amino acid sequence of RSV-7 peptide derived from RSV G protein.

SEQ ID NO:26 is the amino acid sequence of RSV-8 peptide derived from RSV G protein.

SEQ ID NO:27 is the amino acid sequence of RSV-9 peptide derived from RSV M2 protein.

SEQ ID NO:28 is a DNA sequence encoding full-length F protein from hRSV strain A2.

SEQ ID NO:29 is the amino acid sequence of full-length F protein from hRSV strain A2.

SEQ ID NO:30 is a DNA sequence encoding full-length G protein from hRSV strain A2.

SEQ ID NO:31 is the amino acid sequence of full-length G protein from hRSV strain A2.

SEQ ID NO:32 is a DNA sequence encoding full-length M2 protein from hRSV strain A2.

SEQ ID NO:33 is the amino acid sequence of full-length M2 protein from hRSV strain A2.

SEQ ID NO:34 is a DNA sequence encoding full-length N protein from hRSV strain A2.

SEQ ID NO:35 is the amino acid sequence of full-length N protein from hRSV strain A2.

SEQ ID NO:36 is Primer 1 used in RT-qPCR.

SEQ ID NO:37 is Primer 2 used in RT-qPCR.

SEQ ID NO:38 is Probe 6 used in RT-qPCR.

SEQ ID NO:39 is the nucleotide sequence of the PrS promoter.

SEQ ID NO:40 is the nucleotide sequence of the Pr7.5 promoter.

SEQ ID NO:41 is the nucleotide sequence of the PrSyn1lm promoter.

SEQ ID NO:42 is the nucleotide sequence of the PrLE1 promoter.

SEQ ID NO:43 is the nucleotide sequence of the PrH5m promoter.

EXAMPLES

Example 1

Construction of Recombinant MVAs

Generation of recombinant MVA was done by insertion of the RSV coding sequences together with the indicated promoters (FIG. 1) into the MVA genome via homologous recombination in CEF cells using a selection marker to select for recombinant MVA. The use of intergenic regions (IGRs) as insertion sites is described in WO 03/097845. In order to delete the selection marker, a second step of homologous recombination was employed.

MVA-BN® virus was used as starting material for the generation of the recombinant MVA-mBN199B containing the genes for RSV-A2-G and RSV-F-A2_BN in IGR88/89. The PreMaster material of MVA-mBN199 was used as starting material for the generation of MVA-mBN201B described below.

Insertions into IGR88/89 (MVA-mBN199B):

The coding sequence for RSV-A2-G is based on the naturally occurring sequence of the RSV-A2-strain glycoprotein G. The coding sequence of the fusion protein RSV-F-A2 BN is also based on the RSV-A2 strain but was modified by Bavarian Nordic. Both inserted genes were synthesized by Geneart with human adapted codon usage and used for cloning of a recombination plasmid. The protein sequence of RSV-A2-G shows 100% identity to GenBank sequence P03423.1. The protein sequence of RSV-F-A2 BN shows only 99% identity to GenBank sequence P03420.1 due to one single amino acid exchange (P to A) on position 103.

Insertions into IGR148/149 (MVA-mBN201B):

The coding sequences for RSV-N-A2 and RSV-M2-A2 are based on the naturally occurring sequences of the respective RSV-A2-strain glycoproteins. Both genes are connected by a 2A self-cleaving peptide sequence [M. D. Ryan et al. (1991), *J. Gen. Virol.* 72(Pt 11):2727-2732] that allows the expression of two separate native proteins under the control of a single promoter. The coding sequences for RSV-G(B) and RSV-F A long BN were truncated to remove the trans-membrane domains so that the expressed proteins can be secreted. All inserted genes were synthesized by Geneart with optimized codon usage and used for cloning of the recombination plasmid. The protein sequences of RSV-N-A2 and RSV-M2-A2 show 100% identity to GenBank sequence P03418.1 and P04545.1, respectively. The protein sequence of RSV-G(B) truncated shows 100% identity to GenBank sequence P20896.1. The coding sequence of RSV-F A long BN truncated was designed to contain the first 526 amino acids of the RSV-F protein as described by R. P. Du et al. (1994) *Biotechnology* (*N Y*) 12(8):813-818.

Deletion Mutant in M2(A2) of MVA-mBN210BΔM2:

MVA-mBN210BΔM2 includes a deletion mutation in the $12^{th}$ codon of the M2(A2) gene not allowing a functional M2 to be expressed. This deletion causes the addition of the two amino acids threonine and alanine to the first 11 amino acids of M2 (A2) followed by a transcriptional stop (UGA stop codon).

Example 2

Immunogenicity and Efficacy of Recombinant MVA Vaccines Expressing RSV F Protein, RSV G Protein, RSV N Protein, and RSV M2 Protein Vaccine candidate MVA-mBN199B encodes the glycoprotein (G) and the fusion (F) protein of RSV, while MVA-mBN201BΔM2 and MVA-mBN201B express truncated versions of F and G in addition to full-length F and G proteins, the nucleocapsid protein (N) and in case of MVA-mBN201B also the matrix protein (M2) of RSV (see FIG. 1). The objective of these experiments was to analyze the immunogenicity and protective efficacy of MVA-mBN201BΔM2 and MVA-mBN201B compared to MVA-mBN199B after two or three immunizations via the subcutaneous (s.c.) or intranasal (i.n.) routes of administration.

The efficacy of these constructs was tested using an RSV(A2) challenge model in BALB/c mice. Two immunizations with MVA-mBN199B or MVA-mBN201B offered partial protection as judged by real time quantitative polymerase chain reaction (RT-qPCR) when applied subcutaneously and an almost complete protection when applied by the intranasal route. The protection offered by MVA-mBN201B was better than that offered by MVA-mBN199B. There was no difference in the humoral immune responses induced by the two constructs, although major differences were observed in the T-cell responses. MVA-mBN199B induced a good RSV F-specific cellular response, whereas a strong M2-specific T-cell response with MVA-mBN201B was observed, as well as a more pronounced G-specific response compared to MVA-mBN199B. As the IgG and T-cell responses induced after subcutaneous and intranasal immunization were similar, the almost complete sterile immunity obtained by intranasal immunizations likely correlates with the induction and secretion of RSV-specific IgA at the mucosal infection site. For MVA-mBN201BΔM2, the lack of M2-specific T-cells responses correlated with a reduced protection compared to MVA-mBN201B and resulted in a similar protection than MVA-mBN199B.

Study Design

Mice were treated subcutaneously (s.c.) or intranasally (i.n.) with $1\times10^8$ $TCID_{50}$ MVA-mBN199B (Groups 3, 4 and 5), $1\times10^8$ $TCID_{50}$ MVA-mBN201B (Groups 6, 7 and 8), or $1\times10^8$ $TCID_{50}$ MVA-mBN201BΔM2 (Group 9). Mice were treated either two times (Groups 3, 4, 6, 7 and 9) or three times (Groups 5 and 8) according to Table 1. The two control groups were treated (s.c.) twice with TBS (Group 1) or i.n. with RSV (Group 2) according to Table 7. Blood was collected on the day before immunization or challenge as well as on the day of sacrifice. RSV-specific IgG titres were determined by Enzyme-Linked Immunosorbent Assay (ELISA). On Day 48, half of the mice were sacrificed. Their spleens were removed and prepared for the analysis of RSV-specific T-cell responses by Enzyme-Linked Immunosorbent Spot (ELISPOT). On Day 49, the remaining mice were challenged (i.n.) with $10^6$ pfu RSV A2. Appearance and body weight were monitored daily starting on the day of challenge. Four days post challenge, mice were sacrificed by injection of an elevated dose of Ketamine-Xylazine and end-bled. After lung lavage, the lungs were removed and RSV load was analyzed by plaque assay and by RT-qPCR.

TABLE 1

Experimental Design

| Group | Group Size | Cage | Administration of Test or Reference Items: Injections | Schedule (Day)% | Route | Dose per Injection | Bleed and ELISPOT (Day)% | Challenge (Day)%, # |
|---|---|---|---|---|---|---|---|---|
| 1 | 5 | A | TBS | 14 and 35 | s.c. | n.a. | 13, 34, 48 & 53 | 49 |
| | 5 | B | | | | | 13, 34 and 48& | — |
| 2 | 5 | C | RSV | 14 and 35 | i.n. | $10^6$ pfu | 13, 34, 48 and 53 | 49 |
| | 5 | D | | | | | 13, 34 and 48& | — |
| 3 | 5 | E | MVA- | 14 and 35 | s.c. | $1\times10^8$ | 13, 34, 48 and 53 | 49 |
| | 5 | F | mBN199B | | | $TCID_{50}$ | 13, 34 and 48& | — |
| 4 | 5 | G | MVA- | 14 and 35 | i.n. | $1\times10^8$ | 13, 34, 48 and 53 | 49 |
| | 5 | H | mBN199B | | | $TCID_{50}$ | 13, 34 and 48& | — |
| 5 | 5 | J | MVA- | 0, 21 and 35 | s.c. | $1\times10^8$ | −1, 20 34, 48 and 53 | 49 |
| | 5 | K | mBN199B | | | $TCID_{50}$ | −1, 20 34 and 48& | — |
| 6 | 5 | L | MVA- | 14 and 35 | s.c. | $1\times10^8$ | 13, 34, 48 and 53 | 49 |
| | 5 | M | mBN201B | | | $TCID_{50}$ | 13, 34 and 48& | — |
| 7 | 5 | N | MVA- | 14 and 35 | i.n. | $1\times10^8$ | 13, 34, 48 and 53 | 49 |
| | 5 | P | mBN201B | | | $TCID_{50}$ | 13, 34 and 48& | — |
| 8 | 5 | Q | MVA- | 0, 21 and 35 | s.c. | $1\times10^8$ | −1, 20 34, 48 and 53 | 49 |
| | 5 | R | mBN201B | | | $TCID_{50}$ | −1, 20 34 and 48& | — |

TABLE 1-continued Experimental Design

| Group | Group Size | Cage | Injections | Administration of Test or Reference Items | | | | Bleed and ELISPOT (Day)% | Challenge (Day)%, # |
| --- | --- | --- | --- | --- | --- | --- | --- | --- | --- |
| | | | | Schedule (Day)% | | Route | Dose per Injection | | |
| 9 | 5 | W | MVA-mBN201BΔM2 | 14 and 35 | | s.c. | $1 \times 10^8$ TCID$_{50}$ | 13, 34, 48 and 53 | 49 |

%Relative to the first immunization.
Mice were challenged by the intranasal route with $10^6$ pfu of RSV A2. Four days after challenge, mice were bled and sacrificed under anesthesia. BAL fluid and lungs were sampled.
&On Day 48, these mice were sacrificed and spleens were analyzed by ELISPOT.

Study Schedule. The schedule of the in-life phase is summarized in Table 2.

TABLE 2

Study schedule of the In-life Phase

| Day** | Procedures |
| --- | --- |
| −16 | Arrival and import in animal facility of 85 BALB/c mice, cage card allocation and allocation of 5 mice per cage |
| −1 | Ear clipping, inclusion/exclusion examination of all mice |
| −1 | Pre-bleed of mice from cages J, K, Q and R (facial vein puncture right side) |
| 0 | 1st administration of mice from cages J, K, Q and R |
| 13 | pre-bleed of all mice except mice from cages J, K, Q and R (facial vein puncture right side) |
| 14 | 1st administration of all mice except mice from cages J, K, Q and R |
| 20 | Bleed of mice from cages J, K, Q and R (facial vein puncture left side) |
| 21 | 2nd administration of mice from cages J, K, Q and R |
| 34 | Bleed of all mice (retro-bulbar vein puncture left eye) |
| 35 | 2nd administration of all mice except mice from cages J, K, Q and R 3rd administration of mice from cages J, K, Q and R |
| 48 | Bleed of all mice (retro-bulbar vein puncture right eye) Final bleed for cages B, D, F, H, K, M, P and R |
| 48 | Spleens of mice from cages B, D, F, H, K, M, P and R will be removed for analysis by ELISPOT |
| 49 | Challenge of all remaining mice |
| 49 to 53 | Appearance and body weight measurement daily |
| 53 | Final bleed, sacrifice & sampling of BAL & lung of remaining mice |

**Relative to the day of the 1$^{st}$ immunization.

Material and Methods

Experimental Animals. Eighty-five female BALB/cJ Rj (H-2d) mice at the age of seven weeks were obtained from Janvier (Route des Chênes Secs, F-53940 Le Genest-Saint-Isle, France). All mice were specific pathogen free.

Housing. The study was performed in room 117 of the animal facility at Bavarian Nordic-Martinsried. This unit was provided with filtered air at a temperature of 20-24° C. and a relative humidity between 40% and 70%. The room was artificially illuminated on a cycle of 14 hours of light and 10 hours of darkness. The study acclimatization period was 15 days. The animals were housed in transparent SealSafe™-cages (H Temp [polysulfon] cage Type II L—Euro standard), with a floor area of 530 cm². The cages were covered with an H-Temp SealSafe™ lid. The cages were placed in a TECNIPLAST-IVC SealSafe™ system with a SLIMLine™ circulation unit providing every single cage separately with HEPA-filtered air. Animal bedding was changed once a week.

Diet and Water. Mice were provided with free access to irradiated maintenance diet (SSNIFF R/M-H, irradiated, V1534-727) and water (autoclaved at 121° C. for 20 minutes).

Pre-Treatment Procedures: Identification of Animals. To individually mark animals within each cage, ear punching was done according to standard procedures.

Inclusion/Exclusion Examination. Inclusion/exclusion examination was done according to standard procedures.

Blood Sampling for Pre-bleed. Blood samples of approximately 150 µl were obtained by facial vein puncture according to standard procedures. Blood samples were transferred to the laboratory for further processing according to standard procedures.

Treatment Procedures: Preparation and administration of Test Items 1 to 3 and Reference Item. Preparation and administration of test and reference items was performed in a class II microbiological safety cabinet (HERAsafe®/class II type H, Kendro) according to standard procedures. Briefly, for s.c. administration, recombinant MVAs were diluted in TBS to obtain a working solution with a concentration of $2 \times 10^8$ TCID$_{50}$/ml. $1 \times 10^8$ TCID$_{50}$ in 500 µl was injected s.c. according to standard procedures. For i.n. administration, recombinant MVAs were diluted in TBS to obtain a working solution with a concentration of $2 \times 10^9$ TCID$_{50}$/ml. 50 µl of the diluted viruses was administered in one nostril of anesthetized (Xylazine/Ketamine) mice according to standard procedures. 500 µl TBS was administered s.c. according to standard procedures.

Preparation and Administration of Test Item 4/Challenge Virus. The RSV stock vial was thawed and used as quickly as possible due to virus instability (maximal 15 minutes on ice). Virus was kept on ice at all times and used immediately to challenge anaesthetized (Xylazine/Ketamine) mice with 100 µl of the neat virus solution by the intranasal route according to standard procedures.

Post-Treatment Procedures:

Body Weight. Body weights were monitored on a daily basis from the day of challenge until sacrifice according to standard procedures.

Blood Sampling. Blood samples (approximately 150 µl) were obtained by retro-bulbar or facial venous puncture (for details see Table 1 and Table 2) according to standard procedures. Blood samples were transferred to the laboratory for further processing according to standard procedures.

Euthanasia. Euthanasia of half of the mice was performed on Day 48 by cervical dislocation. On Day 53, the remaining mice received a double dose of Ketamine-Xylazine by intra-peritoneal injection and euthanasia was done by cutting the aorta within the peritoneal cavity.

Spleen Removal. Spleens were removed aseptically. They were placed into tubes filled with medium according to standard procedures. These tubes had been imported into the animal facility and were then exported according to standard procedures.

Lung Lavage and Lung Removal. Bronchoalveolar lavage (BAL) fluid was collected by flushing the lungs 4 times with 1 ml of PBS. The lungs were then removed and snap-frozen in two halves in liquid nitrogen for subsequent plaque assay and RNA extraction.

Analysis: Blood Sample Processing and Storage of Sera. Following transfer to the laboratory, the blood samples were processed to serum according to standard procedures. After preparation the sera were stored at −20° C. (±5° C.) until required for analysis.

Analysis of RSV-Specific Antibody Titres from Serum Samples. The total RSV-specific IgG ELISA titres were determined from all serum samples using a modified ELISA kit (Serion ELISA classic, Catalog No. ESR113G): Instead of the Alkaline Phosphatase-conjugated anti-human IgG antibody supplied with the kit, an Alkaline Phosphatase-conjugated goat anti-mouse IgG (Serotec cat: 103004) was used as the secondary antibody.

The RSV-F/G-specific IgG ELISA titers were determined from all serum samples and BAL fluid using a modified ELISA kit (IBL-Hamburg Ref. RE56881). Instead of the POD-conjugated anti-human IgG antibody supplied with the kit, an HRP-conjugated sheep anti-mouse IgG (ref. BN-687-95/96, Serotec cat: AAC10P) was used as the secondary antibody.

Except for groups 4 and 7, The RSV-F-specific IgG ELISA titers were determined from serum samples of Day 48 using a modified ELISA kit (IBL-Hamburg Ref. RE56881 reagents and RSV (F-protein) IgG microtiter strips Ref. RE56692). Instead of the POD-conjugated anti-human IgG antibody supplied within the kit, an HRP-conjugated sheep anti-mouse IgG (ref. BN-687-95/96 Serotec cat: AAC10P) was used as the secondary antibody.

The RSV-specific IgA ELISA titers in sera and BAL fluid were determined from Day 48 and Day 53 samples, respectively, using a modified ELISA kit (IBL-Hamburg Ref. RE56881): Instead of the POD-conjugated anti-human IgG antibody supplied within the kit, an HRP-conjugated sheep anti-mouse IgA (ref. BN-687-95/96 Serotec cat: STAR137P) was used as the secondary antibody.

Analysis of RSV-Specific Cellular Immune Responses from Splenocytes. The RSV F-, RSV G- and RSV M2-specific cellular responses were determined two weeks after the last administration by re-stimulation of splenocytes with specific peptides as described elsewhere (see, e.g., S. M. Varga et al. (2000); S. Johnstone et al. (2004); S. Jiang et al., (2002); and A. B. Kulkarni et al., J. Virol. 67(7):4086-4092 (1993)) and detection of IFNγ release from the splenocytes by ELISPOT assay.

ELISPOT Assay Method. The Mouse IFN-Gamma-Kit (BD Biosciences, Catalog No. 551083) was used for the ELISPOT assay. The assay was performed according to the manufacturer's instructions. Briefly, plates were coated with the capture antibody the day prior to splenocyte isolation. After isolation, cells were transferred to the ELISPOT plates and stimulated with different peptides (see Table 3) for 20 hours at 37° C. IFNγ production was detected using the detection antibody. Plates were developed using the BD™ ELISPOT AEC Substrate Set (BD Biosciences, Catalog No. 551951) according to the manufacturer's instructions.

ELISPOT Stimulation Plan. All conditions were tested in duplicate. RSV-1, RSV-2, RSV-3, RSV-4, and RSV-5 peptides (see Table 3) were used at a final concentration of 5 μg/ml (1 μg/well) to stimulate $5\times10^5$ and $2.5\times10^5$ splenocytes per well. MVA (immunization control) was used at a Multiplicity of Infection (MOI) of 10 to stimulate $5\times10^5$ and $2.5\times10^5$ splenocytes per well and Concanavalin A (ConA [positive control]) was used at a final concentration of 0.5 μg/ml to stimulate $2.5\times10^5$ splenocytes. As a negative control, $5\times10^5$ splenocytes were cultured in medium only (RPMI-1640 supplemented with Glutamax, penicillin, streptomycin, 10% Fetal Calf Serum and $10^5$M β-mercaptoethanol.

TABLE 3

RSV-Specific Stimulation

| Peptide Name | Specificity | Peptide Sequence |
|---|---|---|
| RSV-1 | F | TYMLTNSELL (SEQ ID NO: 19) |
| RSV-2 | F | KYKNAVTEL (SEQ ID NO: 20) |
| RSV-3 | F | ELQLLMQSTPAANNR (SEQ ID NO: 21) |
| RSV-4 | G | WAICKRIPNKKPG (SEQ ID NO: 22) |
| RSV-5 | M2 | SYIGSINNI (SEQ ID NO: 27) |

Analysis of BAL Fluid and Lungs. Cellular characterization of the BAL was not possible, due to staining issues. The RSV load in the lung samples was determined by RSV plaque assay and by RT-qPCR.

RSV plaque assay. One half each of the snap-frozen lungs was homogenized in 1 ml cold medium using a French Press (Dulbecco's Modified Eagle Medium supplemented with 7% Fetal Calf Serum). After a brief centrifugation, two tubes of each supernatant were titrated in two-fold serial dilutions onto Vero cell monolayers grown in 48-well flat-bottomed plates. Six days later, the monolayers were washed and fixed with 1% Formaldehyde. After 24 hours, the monolayers were stained with 0.04% Neutral Red and plaques were counted.

RSV RT-qPCR. 100 μl of the homogenized lung tissue was removed immediately and RNA was isolated using the RNeasy® Mini Kit from Qiagen (Catalog No. 74104). The reverse transcription reaction was performed using the High Capacity RNA-to-cDNA Kit from Applied Biosystems (Catalog No. 4387406). PCR specific for the RSV L gene was performed with the following parameters in a thermal cycler: (1) 50° C. for 2 minutes; (2) 95° C. for 10 minutes; (3) 45 cycles of (15 seconds at 95° C., 1 minute at 60° C.) using the Universal PCR Master Mix from Applied Biosystems (Catalog No. 4352042) and a mixture of three primers: (1) primer 1 (5'-GAA CTC AGT GTA GGT AGA ATG TTT GCA-3'; SEQ ID NO:36); (2) primer 2 (5'-TTC AGC TAT CAT TTT CTC TGC CAA T-3'; SEQ ID NO:37); and (3) probe 6 (5'-TTT GAA CCT GTC TGA ACA TTC CCG GTT-3'; (SEQ ID NO:38). Copy number was determined from a standard curve of pMISC202 plasmid vector containing a fragment of the RSV L gene. Similar reactions for murine beta-actin were used as internal controls for input cDNA using a VIC/MGB-labeled probe from Applied Biosystems (Catalog No. 4351315).

Study Documentation. An in-life phase flow chart was prepared to collect all information during the individual steps of the in-life phase. In addition, mouse- or cage-specific information was recorded on the corresponding cage card. Cage cards are not considered as study raw data but a requirement from the Government of Upper Bavaria.

An analysis phase flow chart was prepared to collect all information during the individual steps of the analysis phase. Assays were documented in assay-specific test records or Laboratory Note Books; cross-references were documented in the analysis phase flow chart. All assay documentation including raw data was reviewed according to standard procedures. In addition, sample tracking sheets for serum samples were prepared according to standard procedures.

Data Processing. The raw data were transferred into the corresponding Excel files for further analysis according to standard procedures.

ELISA. Mean values of the OD and standard errors of the mean were calculated using Excel.

ELISPOT. ELISPOT plates were read with a CTL reader according to the manufacturer's instructions. The number of spot forming cells (SFC) was determined for each well and transferred into an Excel file for further evaluation. From the incubation with $5 \times 10^5$ and $2.5 \times 10^5$ cells per well, the number of spots per $1 \times 10^6$ splenocytes was calculated for each well. The mean for the negative control was calculated and was subtracted from each individual value prior to the calculation of the mean value per mouse to obtain the Stimulation Index (SI) value (peptide-specific frequency of IFN-γ releasing splenocytes) per mouse.

For the peptide stimulations, SI was obtained from the wells with $5 \times 10^5$ and $2.5 \times 10^5$ cells, except when the spots were too numerous to count or for the RSV immunized animals. In those cases only the concentration $2.5 \times 10^5$ was used. For MVA-BN stimulation, SI was obtained from the wells with $5 \times 10^5$, except when the spots were too numerous to count. In that case the concentration $2.5 \times 10^5$ was used. Following determination of the SI for individual animals, the mean of SI (SFC per $1 \times 10^6$ splenocytes) and standard error of the mean (SEM) was calculated per group.

Body weight changes. Individual body weight values (in grams) prior to RSV challenge were taken as baseline values. With these baseline values, individual animal body weight changes (in %), as well as mean body weight changes of the groups were calculated for each monitored time point post challenge using Microsoft Excel.

RSV plaque assay. The numbers of plaques were counted in the well with the three highest countable dilutions of virus. The average number of plaques adjusted by the dilution factor was then multiplied by 10 to obtain the titer of the solution in pfu/ml and finally multiplied by 2 to obtain the titer per lung.

RSV RT-qPCR. PCR amplifications were measured in real time using the ABI 7500 from Applied Biosystems (Catalog No. 4351107) and analyzed using the System Software supplied by Applied Biosystems. All values were compared to the L gene standard and were normalized to the murine beta-actin determination for each sample.

Results

Figure 2:
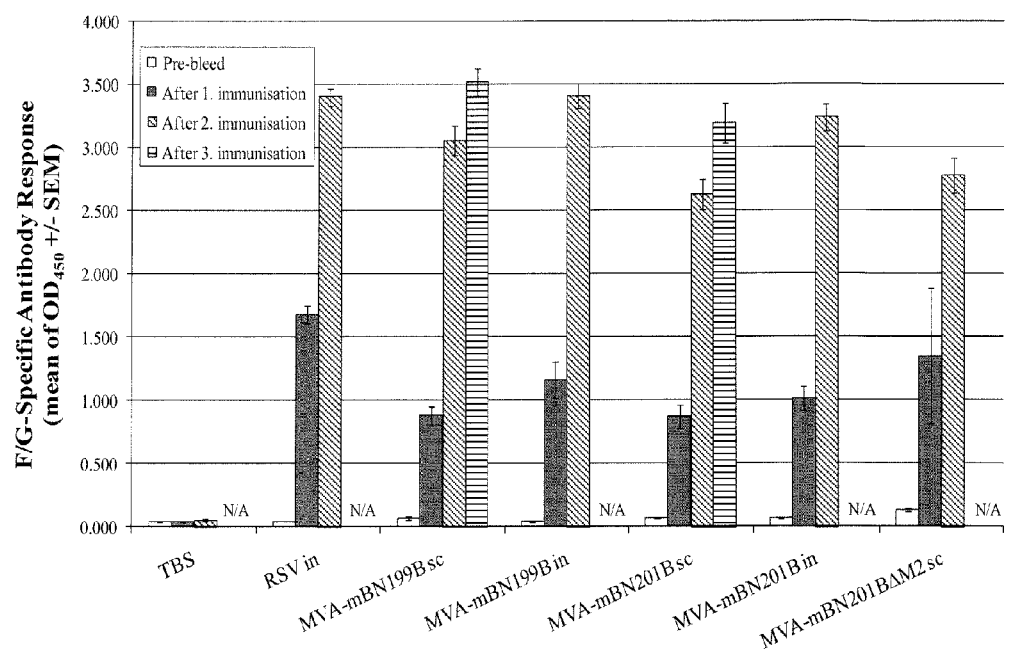
FIG. 2 shows serum RSV-specific IgG responses measured by IBL Hamburg-based ELISA. Mice were immunized (s.c. or i.n.) two or three times with TBS or $1 \times 10^8$ TCID$_{50}$ of either MVA-mBN199B, MVA-mBN201B or MVA-mBN201BΔM2. Control mice were immunized twice i.n. with $10^6$ pfu RSV. Sera were diluted 1/100 and analyzed using an RSV-specific IgG ELISA based on the IBL Hamburg kit using plates coated with RSV F and G proteins.
Figure 3:
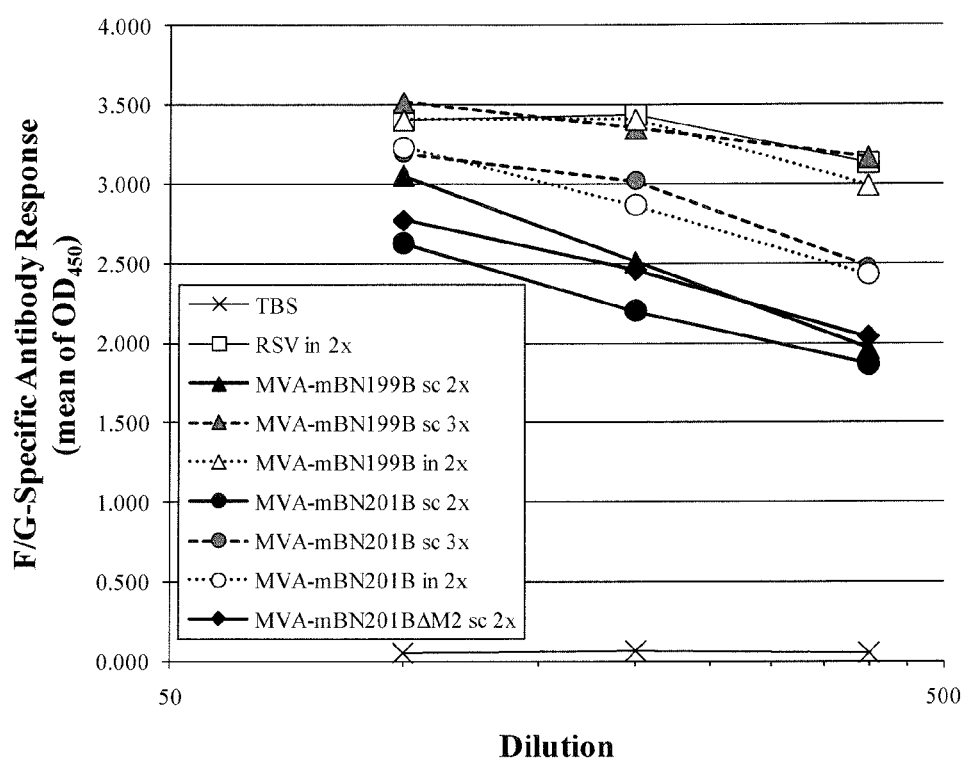
FIG. 3 shows serum RSV-specific IgG responses measured by IBL Hamburg-based ELISA after serial dilution. Mice were immunized two or three times (s.c. or i.n.) with TBS or $1 \times 10^8$ TCID$_{50}$ of MVA-mBN199B, MVA-mBN201B or MVA-mBN201BΔM2. Control mice were immunized twice i.n. with $10^6$ pfu RSV. Sera were diluted (1/100, 1/200 and 1/400) and analyzed using an RSV-specific IgG ELISA based on the IBL Hamburg kit using plates coated with RSV F and G proteins.
Figure 4:
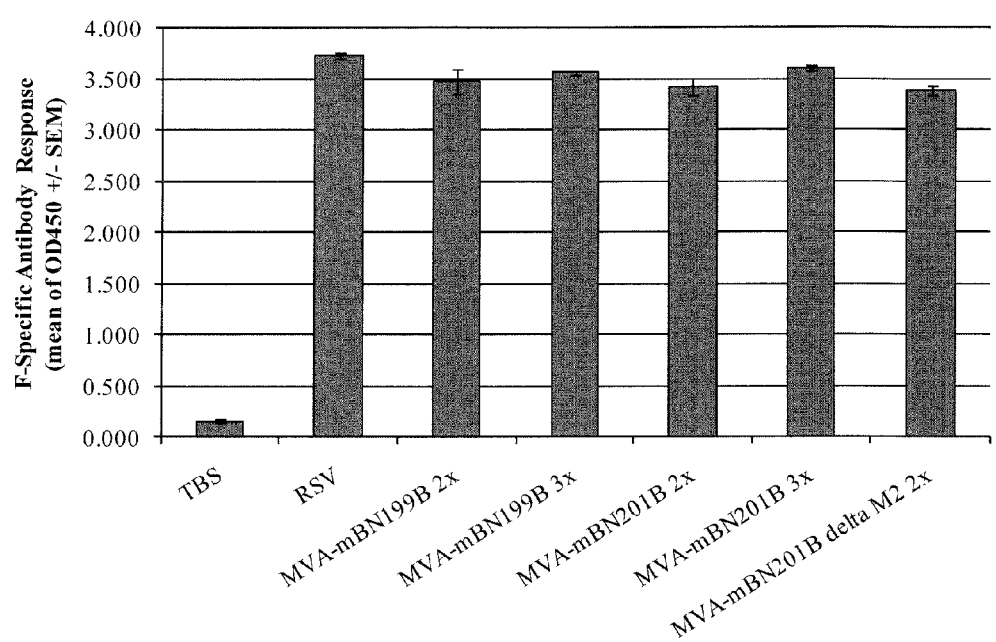
FIG. 4 shows serum RSV-specific IgG responses measured by IBL Hamburg-based ELISA using plates coated only with the F protein. Mice were immunized s.c. two or three times with TBS or $1 \times 10^8$ TCID$_{50}$ of MVA-mBN199B, MVA-mBN201B or MVA-mBN201BΔM2. Control mice were immunized twice i.n. with $10^6$ pfu RSV. Sera were diluted 1/100 and analyzed using an RSV-specific IgG ELISA based on the IBL Hamburg kit using plates coated with RSV F protein only.

Analysis of the Humoral Immune Response: Analysis of RSV-Specific IgG Antibody Response from Serum Samples. Sera were first analyzed with an ELISA based on the IBL-Hamburg kit using plates coated only with recombinant RSV F and G proteins (FIG. 2 and FIG. 3). As shown in FIG. 2, similar RSV-specific IgG responses (ODs ranging between 0.870 and 1.347) were observed with all three constructs (MVA-mBN199B, MVA-mBN201BΔM2 and MVA-mBN201B) after a single immunization and independent of the route used for immunization (s.c. or i.n.). While the second immunization resulted in a 2.0- to nearly 3.5-fold increase in the antibody response (ODs ranging between 2.627 to 3.407), the third s.c. injection had only a minor effect on the B-cell response, producing an increase of approximately 0.500 OD units compared to ODs after the second immunization. Similar results were obtained with an ELISA based on the IBL Hamburg kit using plates coated only with recombinant RSV F protein (FIG. 4).

After serial dilution of sera (1/100, 1/200 and 1/400) RSV F- and RSV G-specific ELISA results showed that MVA-mBN199B, MVA-mBN201BΔM2 and MVA-mBN201B induced similar RSV F- and RSV G-specific IgG responses despite the additional expression of a truncated RSV F protein and a truncated RSV G protein by MVA-mBN201BΔM2 and MVA-mBN201B (FIG. 3). After two s.c. immunizations with the constructs, the B-cell response was still lower compared to the immunization with RSV alone (positive control). To reach the level of antibody response induced by two i.n. applications of RSV required a third s.c. immunization with the MVA-mBNconstructs. In contrast, 2 i.n. immunizations with MVA-mBN199B and MVA-mBN201B induced similar B-cell responses as two immunizations with RSV alone or 3 s.c. immunizations with MVA-mBN199B, MVA-mBN201BΔM2 and MVA-mBN201B, when analyzed with ELISA based on the IBL Hamburg kit (FIG. 3).

Figure 5:
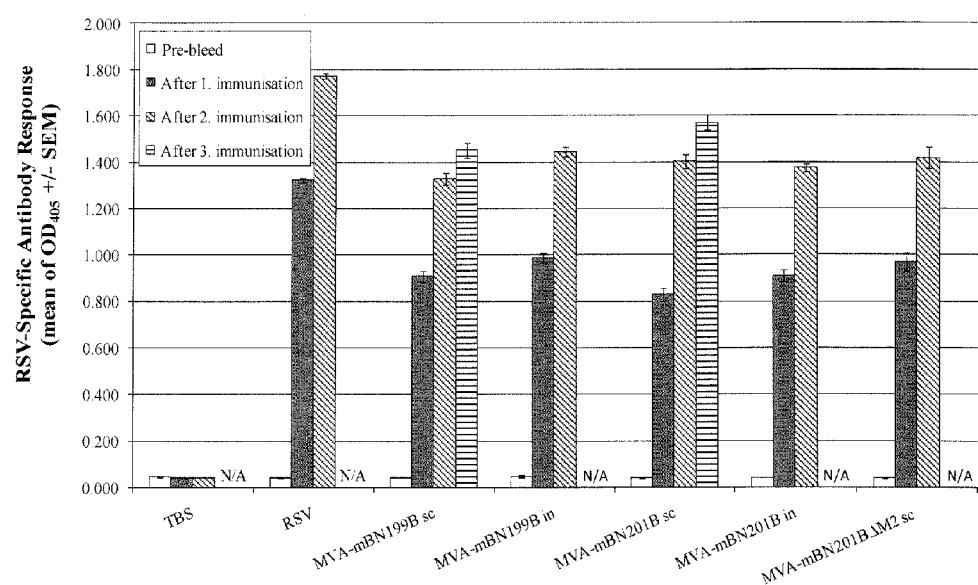
FIG. 5 shows serum RSV-specific IgG responses measured by Serion-based ELISA. Mice were immunized two or three times (s.c. or i.n.) with TBS or $1 \times 10^8$ TCID$_{50}$ of either MVA-mBN199B, MVA-mBN201B or MVA-mBN201BΔM2. Control mice were immunized twice i.n. with $10^6$ pfu RSV. Sera were diluted (1/100) and analyzed using an RSV-specific IgG ELISA based on the Serion kit using plates coated with an RSV lysate.

When sera were analyzed again by ELISA based on the Serion kit using plates coated with an RSV lysate, again no differences between MVA-mBN199B, MVA-mBN201BΔM2 and MVA-mBN201B were found. No differences between 2 and 3 immunizations, or between the s.c. and i.n. routes of administration were observed either. In addition, the responses were all lower than the antibody response induced by 2 i.n. applications of RSV (FIG. 5).

Figure 6:
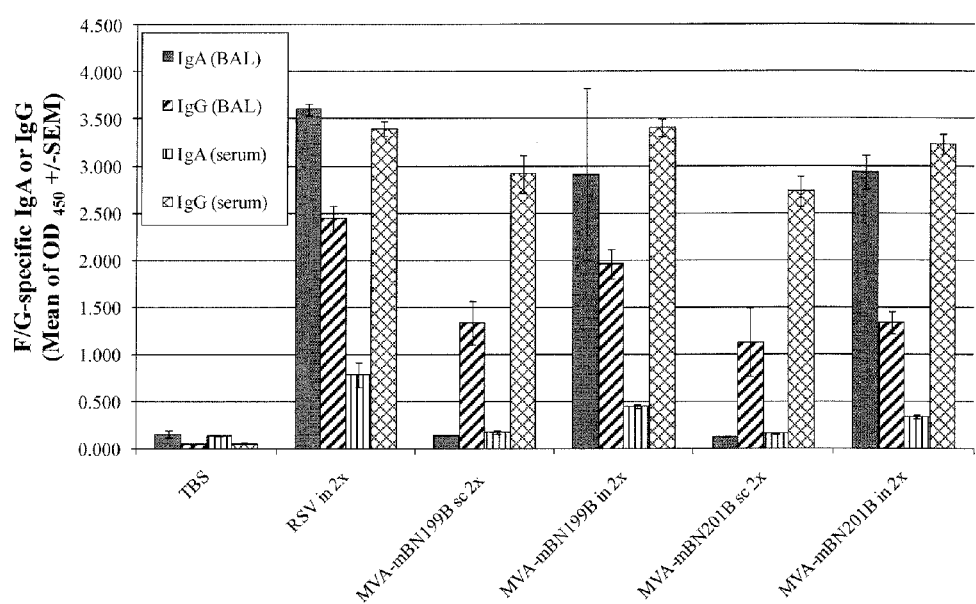
FIG. 6 shows RSV-specific IgA versus IgG responses measured by IBL Hamburg-based ELISA in bronchoalveolar lavage (BAL) fluid and sera. Mice were immunized two or three times (s.c. or i.n.) with TBS or $1\times10^8$ $TCID_{50}$ of MVA-mBN199B, MVA-mBN201B or MVA-mBN201BΔM2. Control mice were immunized twice i.n. with $10^6$ pfu RSV. Sera and BAL fluid were diluted (1/100) and analyzed using an RSV-specific IgG or IgA ELISA based on the IBL Hamburg kit using plates coated with RSV F and G proteins.

Analysis of RSV-Specific IgA Antibody Responses. RSV F- and RSV G-specific IgA (based on the IBL Hamburg kit) was measured in BAL fluid 4 days post-challenge (Day 53). In addition, also BAL and sera for RSV F- and RSV G-specific IgG by ELISA were analyzed. Results were compared to the results obtained in sera just before challenge (Day 48) and are shown in FIG. 6.

As expected, IgA responses were detected only after i.n. application with RSV, MVA-mBN199B and MVA-mBN201B. Although IgG could also be detected in the BAL, IgA was detected at a higher level after i.n. application. Serum levels of IgA were much lower than IgG levels independent of the route of application.

Figure 7:
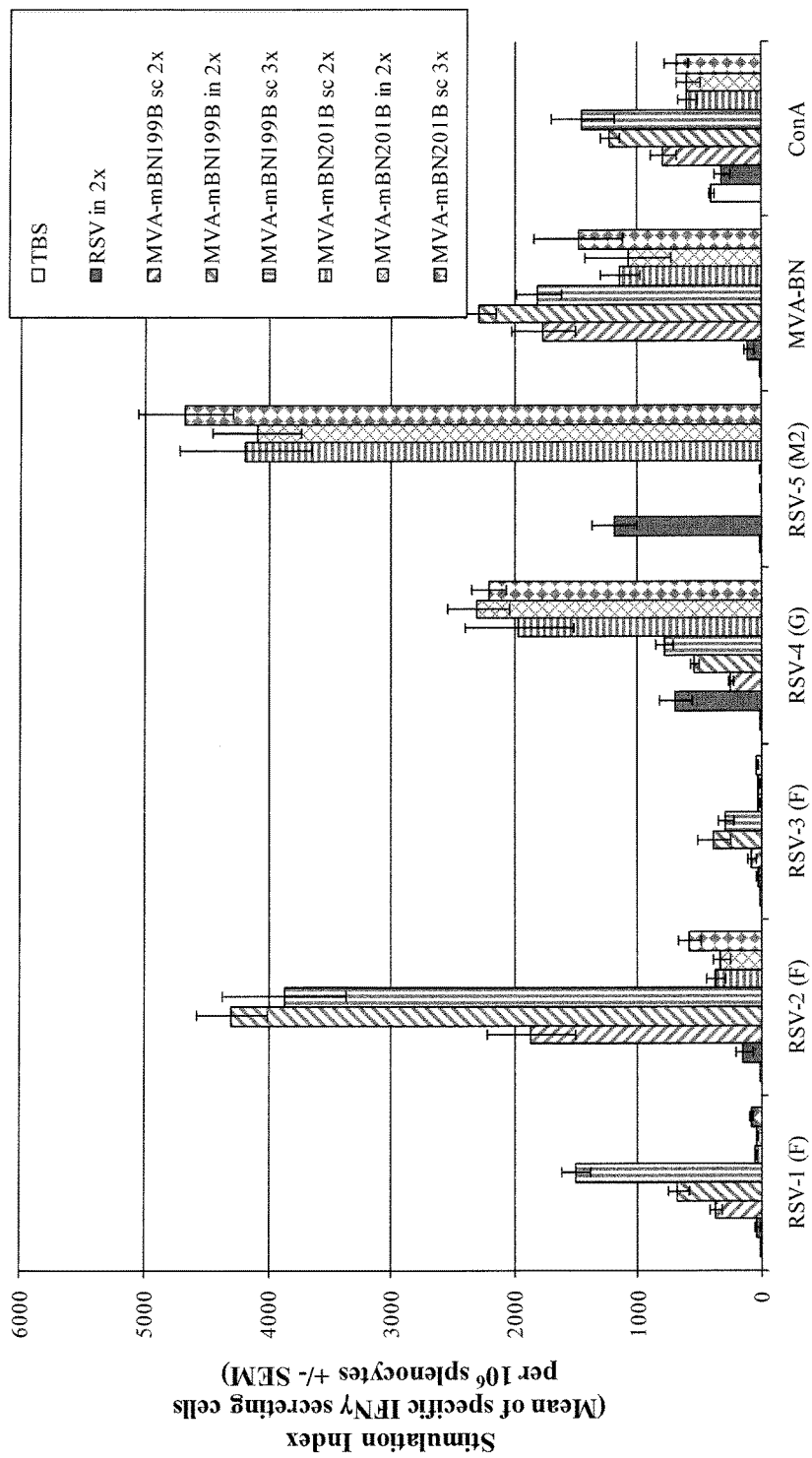
FIG. 7 shows RSV F-, RSV G- and RSV M2-specific T-cell responses measured by ELISPOT. Mice were immunized two or three times (s.c. or i.n.) with TBS or $1\times10^8$ $TCID_{50}$ of either MVA-mBN199B, MVA-mBN201B or MVA-mBN201BΔM2. Control mice were immunized twice i.n. with $10^6$ pfu RSV. Spleens were isolated on Day 48 and splenocytes were restimulated with three different RSV F-specific peptides (RSV-1 (SEQ ID NO:19), RSV-2 (SEQ ID NO:20) and RSV-3 (SEQ ID NO:21), one RSV G-specific peptide (RSV-4 (SEQ ID NO:22)), one RSV M2-specific peptide (RSV-9 (SEQ ID NO:27)) or MVA-BN. IFNγ-secreting cells were detected by ELISPOT. The stimulation index was calculated as explained in the Examples.

Analysis of RSV-Specific Cellular Immune Responses. T-cell responses were analyzed in the spleen by ELISPOT two weeks after the last immunization (FIG. 7). MVA-mBN199B administered by the i.n. or s.c. route induced a strong RSV-F specific T-cell response. This immune response was mainly directed against the RSV-F-specific peptide RSV-2, which is immunodominant in the absence of RSV-M2. The response was around 2000 spots per $10^6$ splenocytes after the $2^{nd}$ s.c. immunization, and around 4000 after the $3^{rd}$ s.c. injection or $2^{nd}$ intranasal application. Similar to the response to RSV intranasal applications, a low G-specific response to peptide RSV-4 was detected after immunization with MVA-mBN199B (approximately 500 spots per $10^6$ splenocytes) and as expected, MVA-mBN199B did not induce M2-specific T-cells. The M2 peptide is the immuno-dominant peptide of RSV in mice. Consequently, RSV intranasal immunizations induced a good M2-specific T-cell response above 1000 spots per $10^6$ splenocytes and almost no F-specific T-cell response.

Like MVA-mBN199B, MVA-mBN201B induced a strong T-cell response, but it was dominated by M2 (above 4000 spots per $10^6$ splenocytes independent of the number of doses administered or the route of administration). Even the G-specific response induced by MVA-mBN201B was at least 3-fold higher than the G-specific response induced by MVA-mBN199B or RSV. In contrast to MVA-mBN199B, the F-specific response induced by MVA-mBN201B was much lower, with less than 600 spots per $10^6$ splenocytes for the RSV-2 peptide.

RSV Challenge with RSV A2 Strain. Mice were challenged intranasally with $10^6$ pfu of RSV(A2) two weeks after the last immunization. Body weight was monitored daily. Four days post challenge, mice were sacrificed. After lung lavage with 1 ml PBS, lungs were removed and the RSV load in lung was determined by plaque assay and RT-qPCR conducted as described above.

Figure 8:
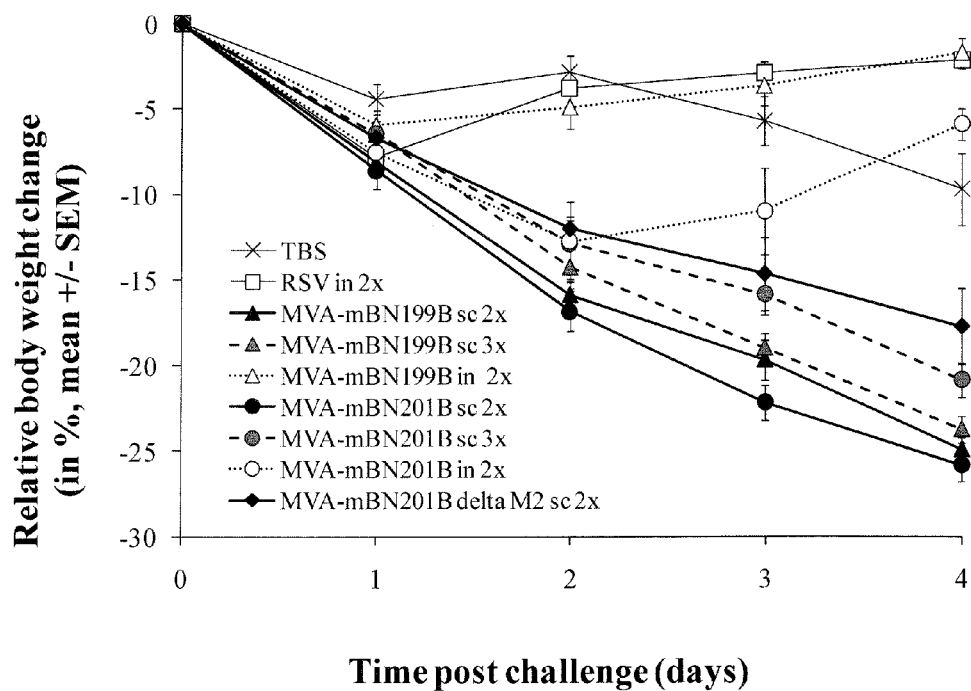
FIG. 8 shows relative body weight loss after challenged with RSV(A2). Mice were immunized two or three times (s.c. or i.n.) with TBS or $1\times10^8$ $TCID_{50}$ of MVA-mBN199B, MVA-mBN201B or MVA-mBN201BΔM2. Control mice were immunized twice i.n. with $10^6$ pfu RSV. Mice were then challenged with $10^6$ pfu RSV(A2) on Day 49. Weight was measured daily from the day of challenge. The weight on the day of challenge was used as baseline to calculate percentage of relative body weight change.
Figure 10:
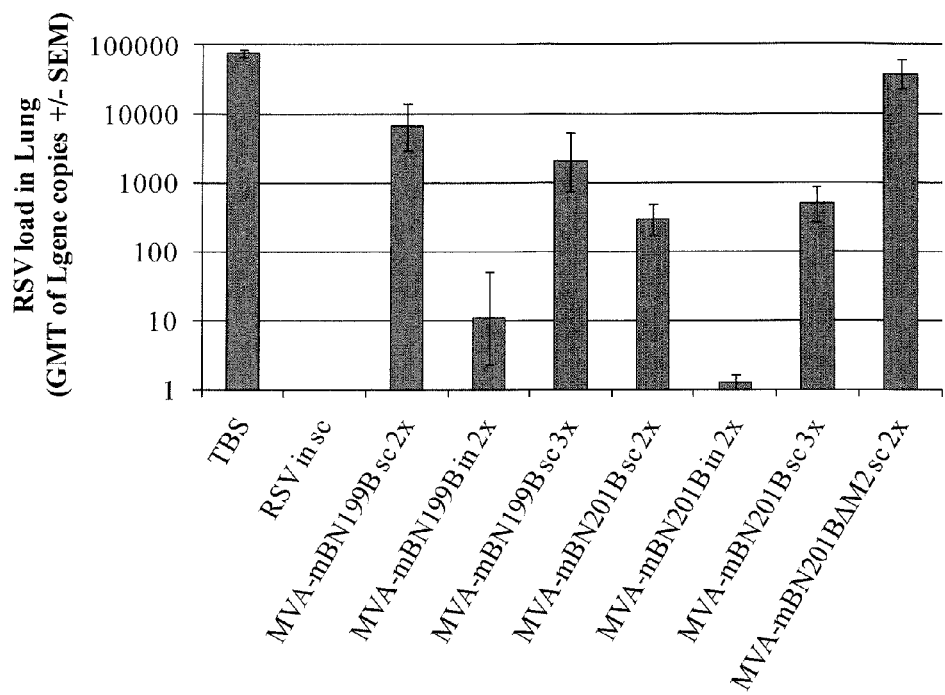
FIG. 10 shows RSV load in lung measured by RT-qPCR. Mice were immunized two or three times (s.c. or i.n.) with TBS or $1\times10^8$ $TCID_{50}$ of MVA-mBN199B, MVA-mBN201B or MVA-mBN201BΔM2. Control mice were immunized twice i.n. with $10^6$ pfu RSV. Mice were then challenged with $10^6$ pfu RSV A2 on Day 49. Lungs were isolated 4 days later and the RSV load (estimated based on the number of L gene copies observed) was determined by RT-qPCR.

Body weight changes. All mice lost weight one day post-challenge, most probably due to anesthesia or the i.n. challenge itself (FIG. 8). TBS-treated mice started to significantly lose weight 4 days post-RSV challenge. In contrast, mice that received RSV intranasally for the third time did not show body weight loss. All mice immunized s.c. with MVA-mBN199B, MVA-mBN201B or MVA-mBN201BΔM2 lost about 20% weight 4 days post challenge. Such weight loss was described earlier by Olszewska et al. (Vaccine 23:215 (2004)). However our RT-qPCR results (FIG. 10) show that it correlates to a better protection and earlier elimination of RSV from lung via the vaccine-primed CTL response compared to the normal clearance of primary RSV infection. When applied i.n., MVA-mBN201B immunized mice had a similar weight loss than s.c. immunized mice 2 days post-challenge, but had recovered 4 days post-challenge due to the low RSV load in lungs compared to the s.c. route (FIG. 10). Like the RSV-immunized group, mice immunized i.n. with MVA-mBN199B showed no weight loss.

Figure 9:
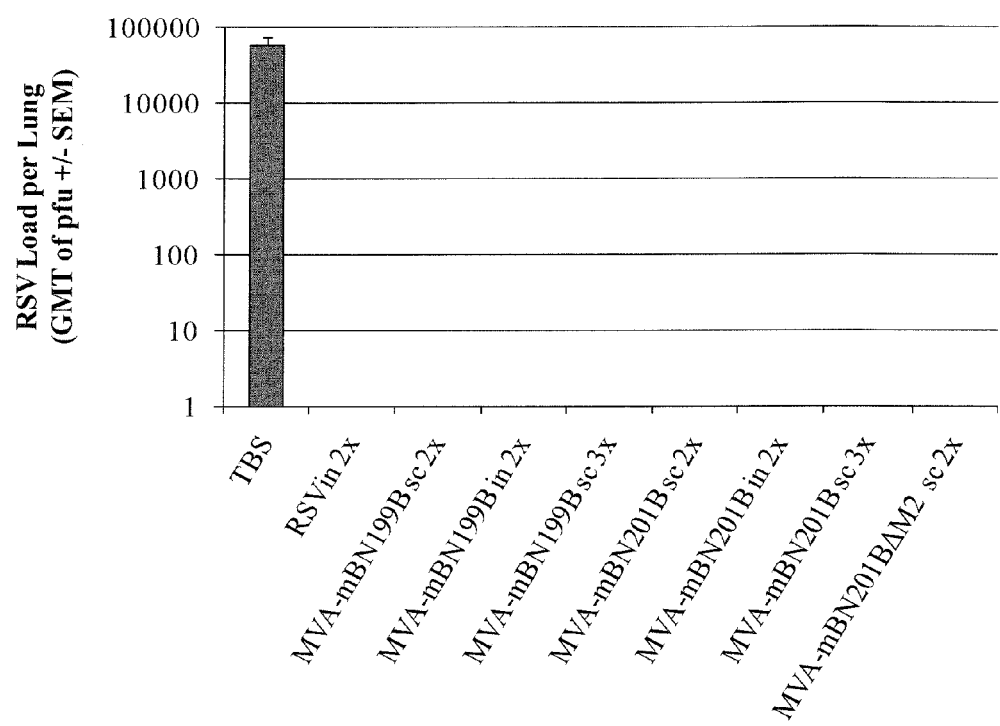
FIG. 9 shows RSV load in lungs measured by plaque assay. Mice were immunized two or three times (s.c. or i.n.) with TBS or $1\times10^8$ $TCID_{50}$ of MVA-mBN199B, MVA-mBN201B or MVA-mBN201BΔM2. Control mice were immunized twice i.n. with $10^6$ pfu RSV. Mice were then challenged with $10^6$ pfu RSV(A2) on Day 49. Lungs were isolated 4 days later and the RSV load (pfu per lung) was determined by plaque assay.

RSV Load Measured by Plaque Assay. Four days post challenge an average of 57671 pfu per lung for the non-immunized mice was detected (FIG. 9). As in the RSV-immunized control group, no RSV A2 plaques were detected in the lungs of animals immunized with MVA-mBN199B, MVA-mBN201B or MVA-mBN201BΔM2 after 2 s.c. or i.n. applications.

RSV Load Measured by Quantitative Real-Time PCR. The RSV load in lung was also analyzed by RT-qPCR (FIG. 10). While RSV was not detected by plaque assay in any of the vaccinated mice, RSV genomes were still detectable in mice immunized three times with MVA-mBN199B. After 3 immunizations with MVA-mBN199B, the RSV load was 38 times lower compared to the TBS control group. RSV genomes were also detectable after three immunizations with MVA-mBN201B but the load was 158 times lower compared to the TBS control group. There was no major difference between mice immunized two or three times. Interestingly, the decrease in the RSV load observed with MVA-mBN201B was not observed after vaccination with MVA-mBN201BΔM2 which was in absence of M2 equivalent to MVA-mBN199B.

Nearly complete protection comparable that obtained in the group treated with RSV was observed after i.n. immunization with MVA-mBN201B, although a few copies of the L gene were still detectable in one mouse out of five. Intranasal immunization with MVA-mBN199B also induced a strong decrease in the RSV load, but the L gene was still detected at a low level in three mice out of four.

Discussion and Conclusions

Although MVA-mBN201B expresses truncated versions of RSV F and G proteins in addition to the full-length RSV F and G proteins also included in the MVA-mBN199B construct, MVA-mBN201B induced a humoral immune response of similar magnitude. Both constructs induced an antibody response directed mostly against the RSV F protein as judged by similarly good responses measured in the RSV F-only ELISA compared to the RSV F and G ELISA. The antibody level following two i.n. applications was higher than after two s.c. applications. A third s.c. application was required to reach the antibody response level induced by two i.n. applications. In contrast, no major differences were observed in the T-cell responses induced using the s.c. versus i.n. routes, or using 2 versus 3 s.c. applications. However, MVA-mBN199B induced a good RSV F-specific cellular response, whereas a strong M2-specific T-cell response with MVA-mBN201B was observed. The RSV G-specific response induced by MVA-mBN201B was also more pronounced compared to MVA-mBN199B. The pattern of T-cell response induced by MVA-mBN201B was similar to the T-cell response induced by RSV immunization, albeit much higher.

Independent of the routes or the number of applications, both constructs protected mice from challenge with RSV (A2), and no replicating virus could be recovered from the lungs. However, as previously observed, s.c. immunizations with MVA-mBN199B or MVA-mBN201B did not result in sterile immunity (i.e., immunity which persists even after the targeted infectious agent is cleared from the body). The genomic RSV load (measured by levels of the viral RNA polymerase (L) gene) in the lungs of mice immunized by s.c. application of MVA-mBN199B or MVA-mBN201B was significantly reduced but still detectable by quantitative RT-PCR, and a third s.c. immunization had no beneficial impact on viral load despite its increase in RSV-specific IgG levels. The reduction in RSV L protein expression was a little more pronounced after vaccination with MVA-mBN201B compared to MVA-mBN199B, which might be due to the increased M2-specific CD8+ T-cell response, as the RSV genomic load was higher in animals vaccinated with MVA-mBN201BΔM2 than for animals vaccinated with MVA-mBN201B, like MVA-mBN199B.

Sterile immunity was almost obtained after two i.n. applications of MVA-mBN199B or MVA-mBN201B. This observation correlated with the induction and secretion of RSV-specific IgA at the mucosal infection site.

Example 3

Safety of Recombinant MVA Vaccines Expressing RSV F Protein, RSV G Protein, RSV N Protein, and RSV M2 Protein, Compared to FI-RSV Vaccine candidate MVA-mBN199B encodes the glycoprotein (G) and the fusion (F) protein of RSV, while MVA-mBN201B express truncated versions of F and G in addition to full-length proteins, the nucleocapsid protein (N) and the matrix protein (M2) of RSV (see FIG. 1). The objective of these experiments was to analyze the safety of MVA-mBN199B and MVA-mBN201B compared to FI-RSV after two immunizations via the subcutaneous (s.c.) or intranasal (i.n.) routes of administration.

The safety of these constructs was tested using an RSV (A2) challenge model in BALB/c mice. Two immunizations with MVA-mBN199B or MVA-mBN201B did not induced increased IL4 and IL5 secretion in BAL following RSV(A2) challenge, compared to FI-RSV.

Study Design

Mice were treated twice three weeks apart subcutaneously (s.c.) or intranasally (i.n.) with $1\times10^8$ TCID$_{50}$ MVA-mBN199B (Groups 3 and 4), $1\times10^8$ TCID$_{50}$ MVA-mBN201B (Groups 5 and 6) according to Table x. The three control groups were treated (s.c.) twice with TBS (Group 1) or i.n. with RSV (Group 2) or i.m. with 30 µg FI-RSV(Group 7), according to Table x. On Day 35, mice were challenged (i.n.) with $10^6$ pfu RSV A2. Four days post challenge, mice were sacrificed by injection of an elevated dose of Ketamine-Xylazine and end-bled. After lung lavage, IL4 and IL5 level were analyzed in BAL by ELISA.

TABLE 4

Experimental Design

Administration of Test or Reference Items

| Group | Group Size | Injections | Schedule (Day)% | Route | Dose per Injection | Challenge (Day)%, # |
|---|---|---|---|---|---|---|
| 1 | 5 | TBS | 0 and 21 | s.c. | n.a. | 35 |
| 2 | 5 | RSV | | i.n. | $10^6$ pfu | |
| 3 | 5 | MVA-mBN199B | | s.c. | $1 \times 10^8$ $TCID_{50}$ | |
| 4 | 5 | | | i.n. | $1 \times 10^8$ $TCID_{50}$ | |
| 5 | 5 | MVA-mBN201B | | s.c. | $1 \times 10^8$ $TCID_{50}$ | |
| 6 | 5 | | | i.n. | $1 \times 10^8$ $TCID_{50}$ | |
| 7 | 5 | FI-RSV | | i.m. | 30 µg | |

%Relative to the first immunization.
Mice were challenged by the intranasal route with $10^6$ pfu of RSV A2. Four days after challenge, mice were bled and sacrificed under anesthesia. BAL fluid were sampled.

Study Schedule. The schedule of the in-life phase is summarized in Table y.

TABLE 5

Study schedule of the In-life Phase

| Day** | Procedures |
|---|---|
| −9 | Arrival and import in animal facility of BALB/c mice, cage card allocation and allocation of 5 mice per cage |
| −1 | Ear clipping, inclusion/exclusion examination of all mice |
| 0 | $1^{st}$ administration of mice |
| 21 | $2^{nd}$ administration of mice |
| 35 | RSV(A2) Challenge |
| 39 | Final bleed, sacrifice & sampling of BAL |

**Relative to the day of the $1^{st}$ immunization.

Material and Methods

Experimental Animals. female BALB/cJ Rj (H-2d) mice at the age of seven weeks were obtained from Janvier (Route des Chênes Secs, F-53940 Le Genest-Saint-Isle, France). All mice were specific pathogen free.

Housing. The study was performed in room 117 of the animal facility at Bavarian Nordic-Martinsried. This unit was provided with filtered air at a temperature of 20-24° C. and a relative humidity between 40% and 70%. The room was artificially illuminated on a cycle of 14 hours of light and 10 hours of darkness. The study acclimatization period was 15 days. The animals were housed in transparent SealSafe™-cages (H Temp [polysulfon] cage Type II L—Euro standard), with a floor area of 530 $cm^2$. The cages were covered with an H-Temp SealSafe™ lid. The cages were placed in a TECNIPLAST-IVC SealSafe™ system with a SLIMLine™ circulation unit providing every single cage separately with HEPA-filtered air. Animal bedding was changed once a week.

Diet and water. Mice were provided with free access to irradiated maintenance diet (SSNIFF R/M-H, irradiated, V1534-727) and water (autoclaved at 121° C. for 20 minutes).

Pre-Treatment Procedures: Identification of Animals. To individually mark animals within each cage, ear punching was done according to standard procedures.

Inclusion/Exclusion Examination. Inclusion/exclusion examination was done according to standard procedures.

Blood Sampling for Pre-bleed. Blood samples of approximately 150 µl were obtained by facial vein puncture according to standard procedures. Blood samples were transferred to the laboratory for further processing according to standard procedures.

Treatment Procedures: Preparation and administration of Test Items and Reference Item. Preparation and administration of test and reference items was performed in a class II microbiological safety cabinet (HERAsafe®/class II type H, Kendro) according to standard procedures. Briefly, for s.c. administration, recombinant MVAs were diluted in TBS to obtain a working solution with a concentration of $2 \times 10^8$ $TCID_{50}$/ml. $1 \times 10^8$ $TCID_{50}$ in 500 µl was injected s.c. according to standard procedures. For i.n. administration, recombinant MVAs were diluted in TBS to obtain a working solution with a concentration of $2 \times 10^9$ $TCID_{50}$/ml. 50 µl of the diluted viruses was administered in one nostril of anesthetized (Xylazine/Ketamine) mice according to standard procedures. 500 µl TBS was administered s.c. according to standard procedures.

Preparation and Administration of RSV(A2) Virus. The RSV stock vial was thawed and used as quickly as possible due to virus instability (maximal 15 minutes on ice). Virus was kept on ice at all times and used immediately to challenge anaesthetized (Xylazine/Ketamine) mice with 100 µl of the neat virus solution by the intranasal route according to standard procedures.

Preparation and Administration of FI-RSV. 30 µg FI-RSV in 40 µl was injected intramuscularly.

Euthanasia. On Day 35, the remaining mice received a double dose of Ketamine-Xylazine by intra-peritoneal injection and euthanasia was done by cutting the aorta within the peritoneal cavity.

Lung Lavage. Bronchoalveolar lavage (BAL) fluid was collected by flushing the lungs 4 times with 1 ml of PBS.

Analysis

IL-4 and IL-5 levels were measured in bronchoalveolar lavage (BAL) supernatant using commercially available ELISA kits (mIL4 PLATINUM ELISA from eBIOSCIENCE Cat No BMS613 and READY-SET-GO MIL-5 ELISA from eBIOSCIENCE Cat No 88-7054-22).

Study Documentation. An in-life phase flow chart was prepared to collect all information during the individual steps of the in-life phase. In addition, mouse- or cage-specific information was recorded on the corresponding cage card. Cage cards are not considered as study raw data but a requirement from the Government of Upper Bavaria.

An analysis phase flow chart was prepared to collect all information during the individual steps of the analysis phase. Assays were documented in assay-specific test records or Laboratory Note Books; cross-references were documented in the analysis phase flow chart. All assay documentation including raw data was reviewed according to standard procedures. In addition, sample tracking sheets for serum samples were prepared according to standard procedures.

Data Processing. The raw data were transferred into the corresponding Excel files for further analysis according to standard procedures.

ELISA. Cytokine concentrations were determined from the standard curve of the respective ELISA kits.

Results

Figure 11:
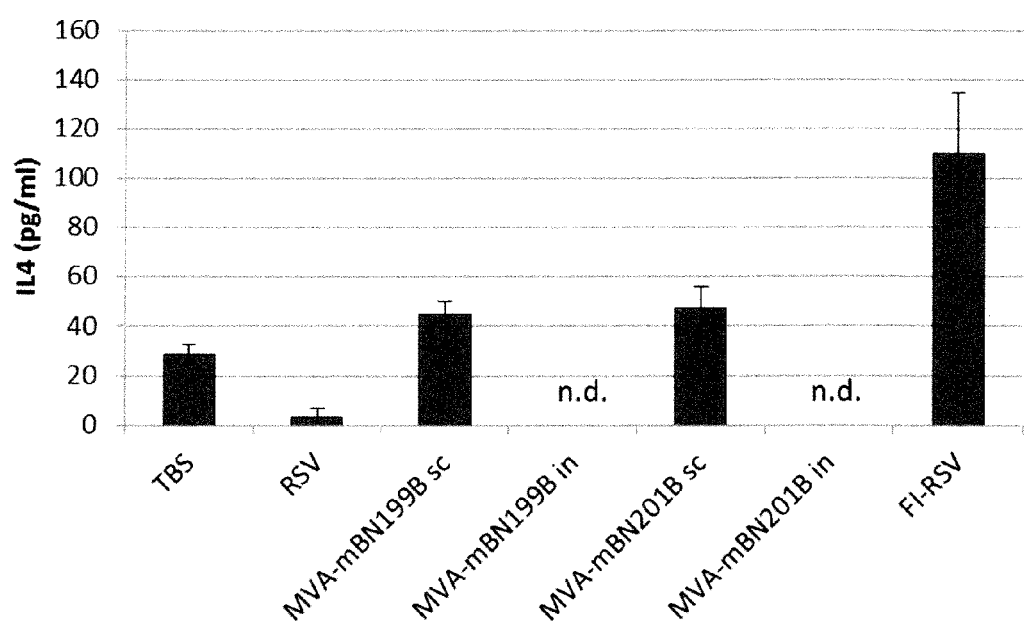
FIG. 11 shows IL4 level in bronchoalveolar lavage (BAL) 4 days post RSV(A2) challenge measured by ELISA. Mice were immunized two times (s.c. or i.n.) with TBS or $1\times10^8$ $TCID_{50}$ of MVA-mBN199B or MVA-mBN201B. Control mice were immunized twice i.n. with $10^6$ pfu RSV. Mice were then challenged with $10^6$ pfu RSV A2. Lungs were washed with 1 ml PBS 4 days later and the IL4 level in BAL was determined by ELISA. (n.d.=not detectable)
Figure 12:
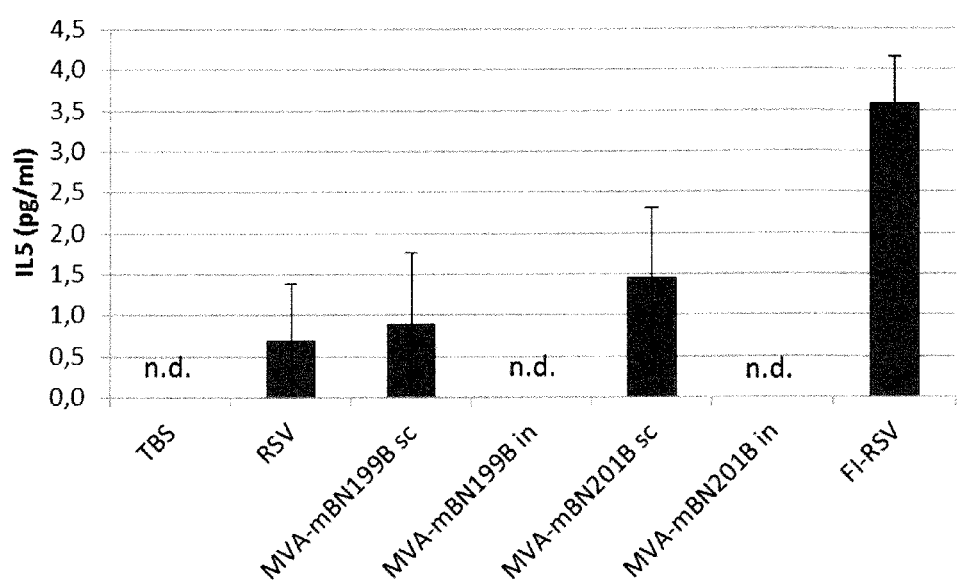
FIG. 12 shows IL5 level in bronchoalveolar lavage (BAL) 4 days post RSV(A2) challenge measured by ELISA. Mice were immunized two times (s.c. or i.n.) with TBS or $1\times10^8$ $TCID_{50}$ of MVA-mBN199B or MVA-mBN201B. Control mice were immunized twice i.n. with $10^6$ pfu RSV. Mice were then challenged with $10^6$ pfu RSV A2. Lungs were washed with 1 ml PBS 4 days later and the IL5 level in BAL was determined by ELISA. (n.d.=not detectable)

An increase of IL-4 (FIG. 11) and IL-5 (FIG. 12) production like that observed with FI-RSV was not observed for MVA-mBN199B or MVA-mBN201B. Both cytokines were below the detection level when mice were immunized i.n. with MVA-mBN199B or MVA-mBN201B.

Discussion and Conclusions

Both MVA-mBN199B and MVA-mBN201B do not induce enhanced disease compared to FI-RSV as assessed by $T_H2$ response.

Example 4

Comparison of Immunogenicity Efficacy and Safety of Different Recombinant MVA Vaccines Expressing RSV F Protein, RSV G Protein, RSV N Protein, and RSV M2 Proteins Vaccine candidate MVA-mBN199B encodes the glycoprotein (G) and the fusion (F) protein of RSV, MVA-mBN201B expresses truncated versions of F and G in addition to full-length proteins, the nucleocapsid protein (N) and the matrix protein (M2) of RSV and MVA-mBN294B expresses one F and and 2 G full-length proteins, the nucleocapsid protein (N) and the matrix protein (M2) of RSV (see FIG. 1). MVA-mBN294A is in an intermediate product in the cloning MVA-mBN294B which still has one cloning cassette in. This cloning cassette does not impact either transgene expression or the immunogenic properties of the transgenic proteins. The objective of this experiment was to analyze the Immunogenicity, efficacy and safety of MVA-mBN294A compared to MVA-mBN199B and MVA-mBN201B after two immunizations via the subcutaneous (s.c.) route of administration.

The immunogenicity efficacy and safety of these constructs was tested using an RSV(A2) challenge model in BALB/c mice. We confirmed that despite the changes in MVA-mBN294A (equivalent to MVA-mBN294B) compared to MVA-mBN201B, it induced similar B- and T-cell responses and offered similar protection. This experiment showed that any constructs (MVA-mBN201B or MVA-mBN294A) expressing at least one antigenic determinant of an RSV membrane glycoprotein (F or G) and at least one antigenic determinant of an RSV nucleocapsid protein (N or M2) induces better protection than a construct expressing only antigenic determinants of RSV membrane glycoproteins (MVA-mBN199B)

Study Design

Mice were vaccinated (s.c.) with $1 \times 10^8$ $TCID_{50}$ MVA-mBN294A, MVA-mBN199B or MVA-mBN201B in a prime-boost schedule (Day 0 and 21) according to Table 6. The control groups were treated twice subcutaneously with TBS or with RSV-A2 according to Table 6. Formalin Inactivated (FI)-RSV was injected intramuscularly (i.m.) either once or twice according to Table 6.

Blood was collected one day prior to each immunization and prior to challenge, as well as on the day of sacrifice. For 5 animals of groups 1 to 5 on Day 34, RSV-specific IgG titers and RSV-specific neutralizing antibody titers were determined by ELISA and PRNT respectively.

On Day 34, some mice (Table 6) were sacrificed by injection of a lethal dose of ketamine-xylazine and final bleed. Spleens were removed and prepared for the analysis of RSV-specific T cell responses by ELISPOT.

On Day 35, the remaining mice (Table 6) were challenged with $10^6$ pfu RSV-A2. Four days post-challenge, mice were sacrificed by injection of a lethal dose of ketamine-xylazine and final bleed. After lung lavage, the lungs were removed and RSV load was analyzed by plaque assay and RT-qPCR. Cellular infiltration and cytokines level in Bonchoalveolar lavage (BAL) fluids were analyzed.

TABLE 6

Experimental Design

| | | | Administration of Test or Reference Items | | | | |
|---|---|---|---|---|---|---|---|
| Group | Group Size | Injections | Schedule for Injections (Day)[1] | Route | Dose per Injection | Bleed (Day)[1] | Challenge (Day)[1,2] |
| 1 | 10 | TBS | 0 and 21 | s.c. | — | −1, 20, 34 and 39 | 35 |
| | 5 | | | | | −1, 20 and 34[&] | — |
| 2 | 10 | RSV | | i.n. | $10^6$ pfu | −1, 20, 34 and 39 | 35 |
| | 5 | | | | | −1, 20 and 34[&] | — |
| 3 | 10 | MVA-mBN199B | | s.c. | $1 \times 10^8$ $TCID_{50}$ | −1, 20, 34 and 39 | 35 |
| | 5 | | | | | −1, 20 and 34[&] | — |
| 4 | 10 | MVA-mBN201B | | | | −1, 20, 34 and 39 | 35 |
| | 5 | | | | | −1, 20 and 34[&] | — |
| 5 | 10 | MVA-mBN294A | | | | −1, 20, 34 and 39 | 35 |
| | 5 | | | | | −1, 20, and 34[&] | — |
| 6 | 10 | FI-RSV | | i.m. | 50 µl | −1, 20, 34 and 39 | 35 |
| | 5 | | | | | −1, 20, and 34[&] | — |
| 7 | 5 | FI-RSV | 0 | i.m. | 50 µl | −1, 20, 34 and 39 | 35 |

[1] relative to the first immunization
[2] Mice will be challenged by the intranasal route with $10^6$ pfu of RSV-A2. Four days after challenge, mice will be bled, sacrificed under anesthesia and BAL and lungs will be sampled
[&] on Day 34, these mice will be sacrificed and spleens will be analyzed by ELISPOT Study Schedule. The schedule of the in-life phase is summarized in Table 7.

TABLE 7

Study schedule of the Part 1 of the In-life Phase

| Day[1] | Procedures |
|---|---|
| −9 | Arrival and import in animal facility of BALB/c mice, cage card allocation and allocation of 5 mice per cage |
| −1 | Ear clipping, inclusion/exclusion examination of all mice |
| −1 | Pre-bleed of all mice (facial vein puncture right side) |
| 0 | $1^{st}$ administration |
| 20 | Bleed of all mice (facial vein puncture left side) |
| 21 | $2^{nd}$ administration |
| 34 | Final bleed, sacrifice and sampling of spleen for cages B, D, F, H, K and M |

TABLE 7-continued

Study schedule of the Part 1 of the In-life Phase

| Day[1] | Procedures |
|---|---|
| 34 | Bleed of all remaining mice (retro-bulbar vein puncture right eye) |
| 35 | Challenge of all remaining mice |
| 35 to 39 | Appearance and body weight measurement daily |
| 39 | Final bleed, sacrifice and sampling of BAL and lung of mice |

[1]relative to the day of the 1st immunization

Material and Methods

Experimental Animals. female BALB/cJ Rj (H-2d) mice at the age of seven weeks were obtained from Janvier (Route des Chênes Secs, F-53940 Le Genest-Saint-Isle, France). All mice were specific pathogen free.

Housing. The study was performed in room 117 of the animal facility at Bavarian Nordic-Martinsried. This unit was provided with filtered air at a temperature of 20-24° C. and a relative humidity between 40% and 70%. The room was artificially illuminated on a cycle of 14 hours of light and 10 hours of darkness. The study acclimatization period was 15 days. The animals were housed in transparent SealSafe™-cages (H Temp [polysulfon] cage Type II L—Euro standard), with a floor area of 530 cm². The cages were covered with an H-Temp SealSafe™ lid. The cages were placed in a TECNIPLAST-IVC SealSafe™ system with a SLIMLine™ circulation unit providing every single cage separately with HEPA-filtered air. Animal bedding was changed once a week.

Diet and water. Mice were provided with free access to irradiated maintenance diet (SSNIFF R/M-H, irradiated, V1534-727) and water (autoclaved at 121° C. for 20 minutes).

Pre-Treatment Procedures:

Identification of Animals. To individually mark animals within each cage, ear punching was done according to standard procedures.

Inclusion/Exclusion Examination. Inclusion/exclusion examination was done according to standard procedures.

Blood Sampling for Pre-bleed. Blood samples of approximately 150 µl were obtained by facial vein puncture according to standard procedures. Blood samples were transferred to the laboratory for further processing according to standard procedures.

Treatment Procedures: Preparation and administration of Test Items and Reference Item. Preparation and administration of test and reference items was performed in a class II microbiological safety cabinet (HERAsafe®/class II type H, Kendro) according to standard procedures. Briefly, for s.c. administration, recombinant MVAs were diluted in TBS to obtain a working solution with a concentration of $2 \times 10^8$ $TCID_{50}$/ml. $1 \times 10^8$ $TCID_{50}$ in 500 µl was injected s.c. according to standard procedures. 500 µl TBS was administered s.c. according to standard procedures.

Preparation and Administration of RSV(A2) Virus. The RSV stock vial was thawed and used as quickly as possible due to virus instability (maximal 15 minutes on ice). Virus was kept on ice at all times and used immediately to challenge anaesthetized (Xylazine/Ketamine) mice with 100 µl of the neat virus solution by the intranasal route according to standard procedures.

Preparation and Administration of FI-RSV: 50 µl of FI-RSV was applied i.m.

Post-Treatment Procedures:

Blood Sampling. Blood samples (approximately 150 µl) were obtained by retro-bulbar or facial venous puncture (for details see Table 7) according to standard procedures. Blood samples were transferred to the laboratory for further processing according to standard procedures.

Euthanasia. Mice received a double dose of Ketamine-Xylazine by intra-peritoneal injection and euthanasia was done by cutting the aorta within the peritoneal cavity.

Spleen Removal. Spleens were removed aseptically. They were placed into tubes filled with medium according to standard procedures. These tubes had been imported into the animal facility and were then exported according to standard procedures.

Lung Lavage and Lung Removal. Bronchoalveolar lavage (BAL) fluid was collected by flushing the lungs 4 times with 1 ml of PBS. The lungs were then removed and snap-frozen in two halves in liquid nitrogen for subsequent plaque assay and RNA extraction.

Analysis:

Blood Sample Processing and Storage of Sera. Following transfer to the laboratory, the blood samples were processed to serum according to standard procedures. After preparation the sera were stored at −20° C. (±5° C.) until required for analysis.

Analysis of RSV-Specific Antibody Titres from Serum Samples. The total RSV-specific IgG ELISA titres were determined from all serum samples using a modified ELISA kit (Serion ELISA classic, Catalog No. ESR113G): Instead of the Alkaline Phosphatase-conjugated anti-human IgG antibody supplied with the kit, an Alkaline Phosphatase-conjugated goat anti-mouse IgG (Serotec cat: 103004) was used as the secondary antibody.

Analysis of RSV-Specific Neutralizing Antibody Titres from Serum Samples. Briefly, 2-fold serial dilutions of the test sera were prepared and a defined number of RSV plaque forming units (pfu) were added to the serum dilution. After 185 min incubation at 36° C. (±2° C.) and 5% $CO_2$ (±1%). It was added to pre-seeded plates containing Vero cells. Two days later plates were fixed, immuno-stained with a mixture of RSV-specific antibodies and plaques were counted.

Analysis of RSV-Specific Cellular Immune Responses from Splenocytes. The RSV F- and RSV M2-specific cellular responses were determined two weeks after the last administration by re-stimulation of splenocytes with specific peptides as described elsewhere and detection of IFNγ release from the splenocytes by ELISPOT assay.

ELISPOT Assay Method. The Mouse IFN-Gamma-Kit (BD Biosciences, Catalog No. 551083) was used for the ELISPOT assay. The assay was performed according to the manufacturer's instructions. Briefly, plates were coated with the capture antibody the day prior to splenocyte isolation. After isolation, cells were transferred to the ELISPOT plates and stimulated with different peptides (see Table 3) for 20 hours at 37° C. IFNγ production was detected using the detection antibody. Plates were developed using the BD™ ELISPOT AEC Substrate Set (BD Biosciences, Catalog No. 551951) according to the manufacturer's instructions.

ELISPOT Stimulation Plan. All conditions were tested in duplicate. RSV-2 and RSV-5 peptides (see Table 8) were used at a final concentration of 5 µg/ml (1 µg/well) to stimulate $5 \times 10^5$ and $2.5 \times 10^5$ splenocytes per well. MVA (immunization control) was used at a Multiplicity of Infection (MOI) of 10 to stimulate $5 \times 10^5$ and $2.5 \times 10^5$ splenocytes per well and Concanavalin A (ConA [positive control]) was used at a final concentration of 0.5 µg/ml to stimulate $2.5 \times 10^5$ splenocytes. As a negative control, $5 \times 10^5$ splenocytes were cultured in medium only (RPMI-1640 supplemented with Glutamax, penicillin, streptomycin, 10% Fetal Calf Serum and $10^5$ M β-mercaptoethanol.

TABLE 8

RSV-Specific Stimulation

| Peptide Name | Specificity | Peptide Sequence |
|---|---|---|
| RSV-2 | F | KYKNAVTEL (SEQ ID NO: 20) |
| RSV-5 | M2 | SYIGSINNI (SEQ ID NO: 27) |

Analysis of BAL Fluid:

Two slides were prepared by cytospin centrifugation (800 rpm, 5 minutes) of 100 µl of BAL fluid. Slides were dried overnight and then stained. Slides were analyzed by microscopy to determine the percentage of eosinophils and neutrophils. The rest of the BAL was then be centrifuged (12,000 rpm 5 minutes). After preparation, the BAL supernatants were stored at −20° C. (±5° C.) until analysis. IL-4 and IL-5 levels were measured in bronchoalveolar lavage (BAL) supernatant using commercially available ELISA kits (mIL4 PLATINUM ELISA from eBIOSCIENCE Cat No BMS613 and READY-SET-GO MIL-5 ELISA from eBIOSCIENCE Cat No 88-7054-22).

Analysis of RSV Load in the Lung

The RSV load in the lung samples was determined by RSV plaque assay and by RT-qPCR.

RSV Plaque Assay. One half each of the snap-frozen lungs was homogenized in 1 ml cold medium using a French Press (Dulbecco's Modified Eagle Medium supplemented with 7% Fetal Calf Serum). After a brief centrifugation, two tubes of each supernatant were titrated in two-fold serial dilutions onto Vero cell monolayers grown in 48-well flat-bottomed plates. Six days later, the monolayers were washed and fixed with 1% Formaldehyde. After 24 hours, the monolayers were stained with 0.04% Neutral Red and plaques were counted.

RSV RT-qPCR. 100 µl of the homogenized lung tissue was removed immediately and RNA was isolated using the RNeasy® Mini Kit from Qiagen (Catalog No. 74104). The reverse transcription reaction was performed using the High Capacity RNA-to-cDNA Kit from Applied Biosystems (Catalog No. 4387406). PCR specific for the RSV L gene was performed with the following parameters in a thermal cycler: (1) 50° C. for 2 minutes; (2) 95° C. for 10 minutes; (3) 45 cycles of (15 seconds at 95° C., 1 minute at 60° C.) using the Universal PCR Master Mix from Applied Biosystems (Catalog No. 4352042) and a mixture of three primers: (1) primer 1 (5'-GAA CTC AGT GTA GGT AGA ATG TTT GCA-3'; SEQ ID NO:36); (2) primer 2 (5'-TTC AGC TAT CAT TTT CTC TGC CAA T-3'; SEQ ID NO:37); and (3) probe 6 (5'-TTT GAA CCT GTC TGA ACA TTC CCG GTT-3'; (SEQ ID NO:38). Copy number was determined from a standard curve of pMISC202 plasmid vector containing a fragment of the RSV L gene. Similar reactions for murine beta-actin were used as internal controls for input cDNA using a VIC/MGB-labeled probe from Applied Biosystems (Catalog No. 4351315).

Study Documentation.

An in-life phase flow chart was prepared to collect all information during the individual steps of the in-life phase. In addition, mouse- or cage-specific information was recorded on the corresponding cage card. Cage cards are not considered as study raw data but a requirement from the Government of Upper Bavaria.

An analysis phase flow chart was prepared to collect all information during the individual steps of the analysis phase. Assays were documented in assay-specific test records or Laboratory Note Books; cross-references were documented in the analysis phase flow chart. All assay documentation including raw data was reviewed according to standard procedures. In addition, sample tracking sheets for serum samples were prepared according to standard procedures.

Data Processing. The raw data were transferred into the corresponding Excel files for further analysis according to standard procedures.

ELISA. Mean values of the OD and standard errors of the mean were calculated using Excel.

PRNT. Plaques were transfer to a macro to calculate a PRNT titer according to standard procedures.

ELISPOT. ELISPOT plates were read with a CTL reader according to the manufacturer's instructions. The number of spot forming cells (SFC) was determined for each well and transferred into an Excel file for further evaluation. From the incubation with $5 \times 10^5$ and $2.5 \times 10^5$ cells per well, the number of spots per $1 \times 10^6$ splenocytes was calculated for each well. The mean for the negative control was calculated and was subtracted from each individual value prior to the calculation of the mean value per mouse to obtain the Stimulation Index (SI) value (peptide-specific frequency of IFN-γ releasing splenocytes) per mouse.

For the peptide stimulations, SI was obtained from the wells with $5 \times 10^5$ and $2.5 \times 10^5$ cells, except when the spots were too numerous to count or for the RSV immunized animals. In those cases only the concentration $2.5 \times 10^5$ was used. For MVA-BN stimulation, SI was obtained from the wells with $5 \times 10^5$, except when the spots were too numerous to count. In that case the concentration $2.5 \times 10^5$ was used. Following determination of the SI for individual animals, the mean of SI (SFC per $1 \times 10^6$ splenocytes) and standard error of the mean (SEM) was calculated per group.

RSV plaque assay. The numbers of plaques were counted in the well with the three highest countable dilutions of virus. The average number of plaques adjusted by the dilution factor was then multiplied by 10 to obtain the titer of the solution in pfu/ml and finally multiplied by 2 to obtain the titer per lung.

RSV RT-qPCR. PCR amplifications were measured in real time using the ABI 7500 from Applied Biosystems (Catalog No. 4351107) and analyzed using the System Software supplied by Applied Biosystems. All values were compared to the L gene standard and were normalized to the murine beta-actin determination for each sample.

Cytokines ELISA. Cytokine concentrations were determined from the standard curve of the respective ELISA kits.

Results

Figure 13:
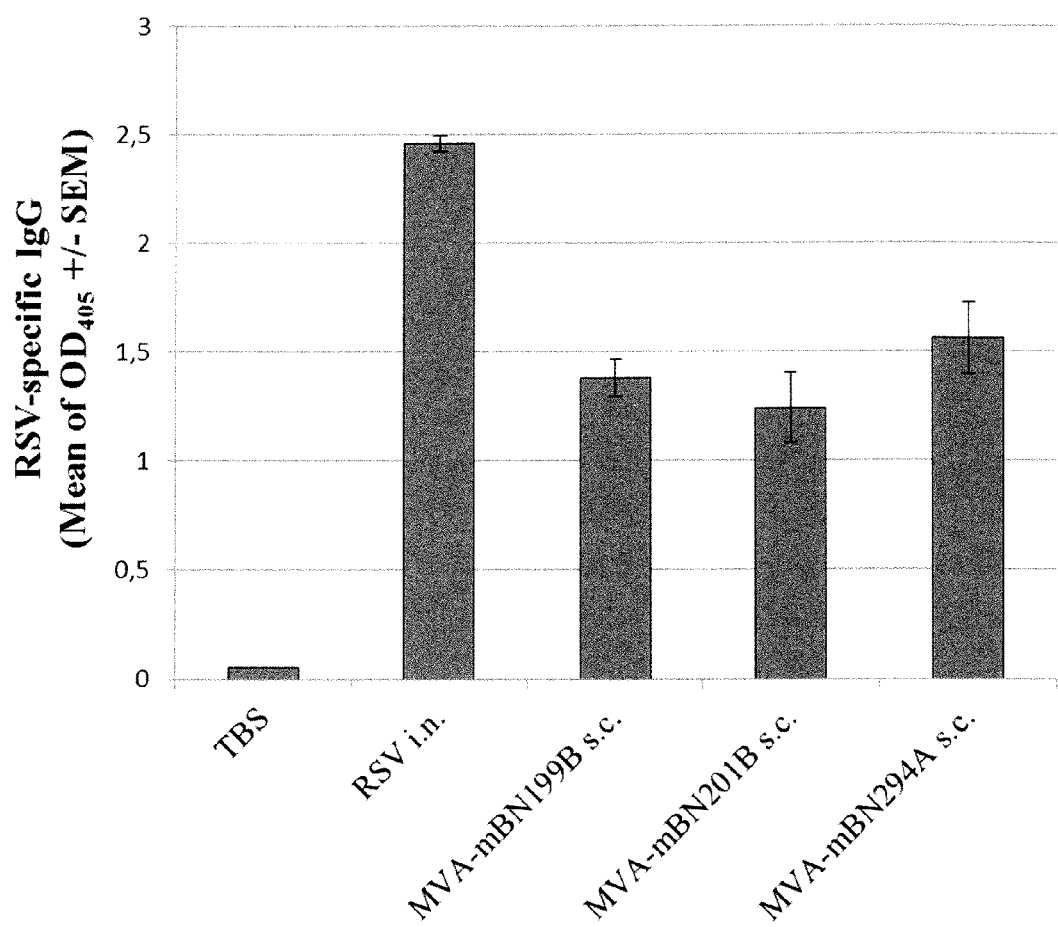
FIG. 13 shows serum RSV-specific IgG responses measured by Serion-based ELISA. Mice were immunized s.c. twice 3 weeks apart with TBS or $1\times10^8$ $TCID_{50}$ of either MVA-mBN199B, MVA-mBN201B or MVA-mBN294A. Control mice were immunized twice i.n. with $10^6$ pfu RSV. Sera of 5 mice per group obtained 2 weeks after the last immunization were diluted and analyzed using an RSV-specific IgG ELISA based on the Serion kit using plates coated with an RSV lysate.
Figure 14:
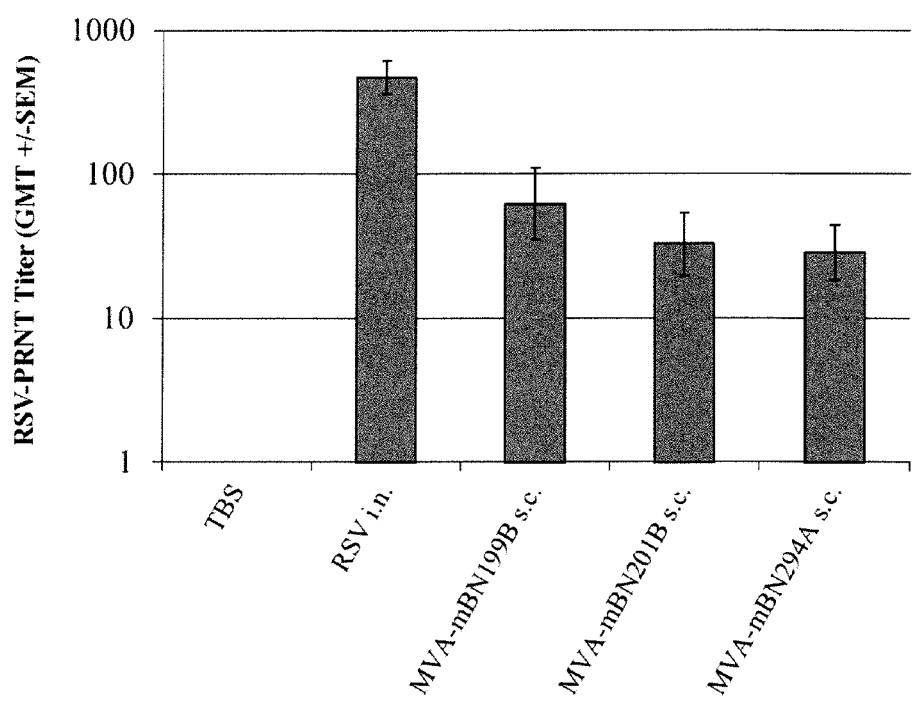
FIG. 14 shows serum RSV-specific neutralizing antibody responses measured by PRNT. Mice were immunized s.c. twice 3 weeks apart with TBS or $1\times10^8$ $TCID_{50}$ of either MVA-mBN199B, MVA-mBN201B or MVA-mBN294A. Control mice were immunized twice i.n. with $10^6$ pfu RSV. Sera of 5 mice per group obtained 2 weeks after the last immunization analyzed by PRNT.

Analysis of the Humoral Immune Response:

For both RSV-specific IgG (ELISA, FIG. 13) and RSV-specific neutralizing antibody responses (PRNT, FIG. 14) we did not observe any differences between the three constructs (MVA-mBN199B, MVA-mBN201B and MVA-mBN294A)

Figure 15:
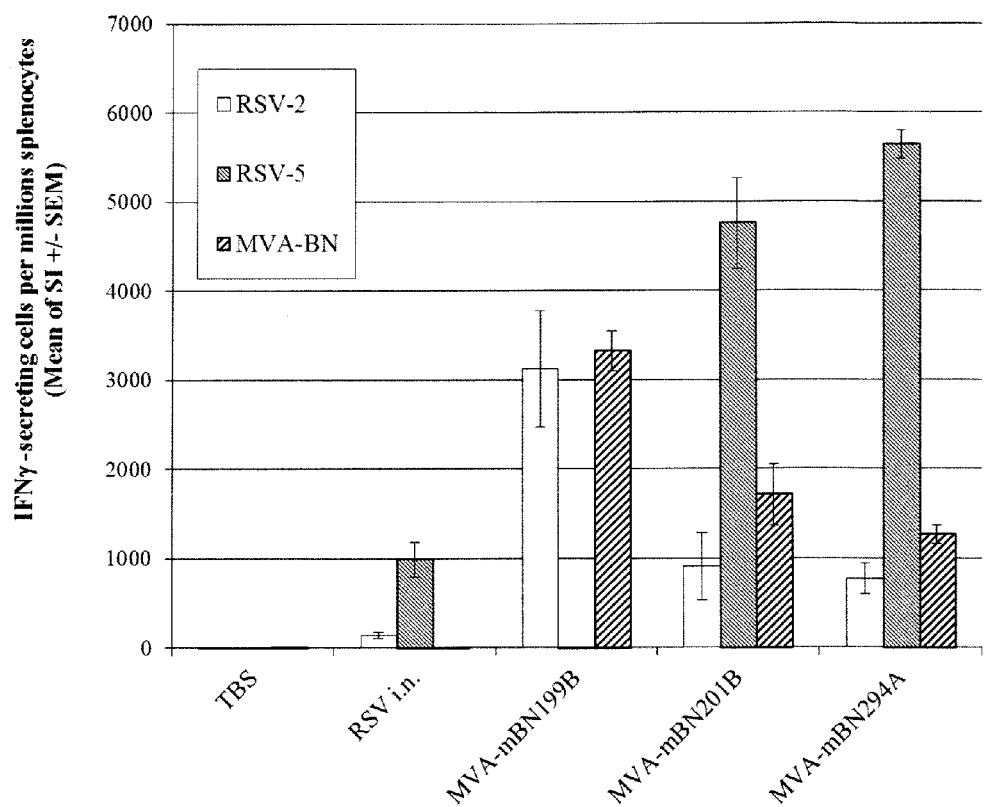
FIG. 15 shows RSV F- and RSV M2-specific T-cell responses measured by ELISPOT. Mice were immunized s.c. twice 3 weeks apart with TBS or $1\times10^8$ $TCID_{50}$ of either MVA-mBN199B, MVA-mBN201B or MVA-mBN294A. Control mice were immunized twice i.n. with $10^6$ pfu RSV. Spleens were isolated on Day 34 and splenocytes were restimulated with one RSV F-specific peptides (RSV-2 (SEQ ID NO:20), one RSV M2-specific peptide (RSV-9 (SEQ ID NO:27)) or MVA-BN. IFNγ-secreting cells were detected by ELISPOT. The stimulation index was calculated as explained in the Examples.

Analysis of the Cellular Immune Response:

As expected, MVA-mBN294A had a similar T-cell response pattern than MVA-mBN201B (FIG. 15), inducing both F and M2 specific responses dominated by the M2 T-cell response. In contrast, MVA-mBN199B only induced a F-specific response but at a higher level than MVA-mBN201B and MVA-mBN294A.

Analysis of the RSV Load in the Lungs:

RSV Challenge with RSV A2 Strain. Mice were challenged intranasally with $10^6$ pfu of RSV(A2) two weeks after the last immunization. Four days post-challenge, mice were sacrificed. After lung lavage with 1 ml PBS, lungs were removed and the RSV load in lung was determined by plaque assay and RT-qPCR conducted as described above.

Figure 16:
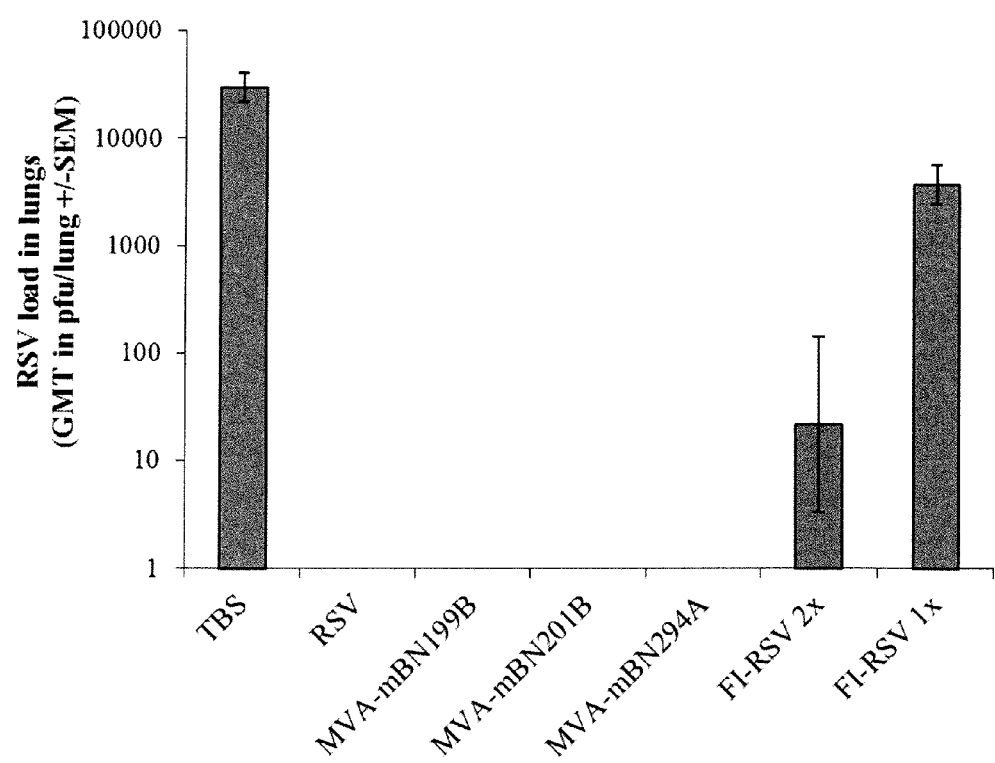
FIG. 16 shows RSV load in lungs measured by plaque assay. Mice were immunized s.c. twice 3 weeks apart with TBS or $1\times10^8$ $TCID_{50}$ of either MVA-mBN199B, MVA-mBN201B or MVA-mBN294A. Control mice were immunized twice i.n. with $10^6$ pfu RSV or i.m. with 50 μl FI-RSV. Mice were then challenged with $10^6$ pfu RSV(A2) on Day 49. Lungs were isolated 4 days later and the RSV load (pfu per lung) was determined by plaque assay.

RSV Load Measured by Plaque Assay. Four days post challenge an average of 29842 pfu per lung for the non-immunized mice was detected (FIG. 16). As in the RSV-immunized control group, no RSV A2 plaques were detected in the lungs of animals immunized with MVA-mBN199B, MVA-mBN201B or MVA-mBN294A after 2 s.c. applications.

Figure 17:
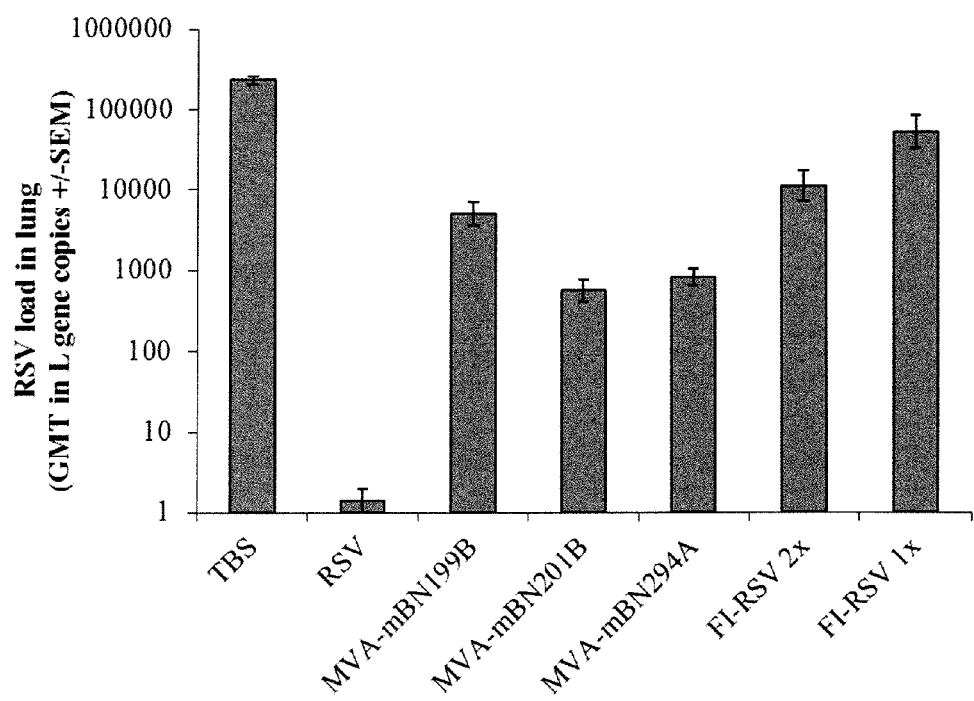
FIG. 17 shows RSV load in lung measured by RT-qPCR. Mice were immunized s.c. twice 3 weeks apart with TBS or $1\times10^8$ $TCID_{50}$ of either MVA-mBN199B, MVA-mBN201B or MVA-mBN294A. Control mice were immunized twice i.n. with $10^6$ pfu RSV or i.m. with 50 μl FI-RSV. Mice were then challenged with $10^6$ pfu RSV A2 on Day 49. Lungs were isolated 4 days later and the RSV load (estimated based on the number of L gene copies observed) was determined by RT-qPCR.
Figure 18:
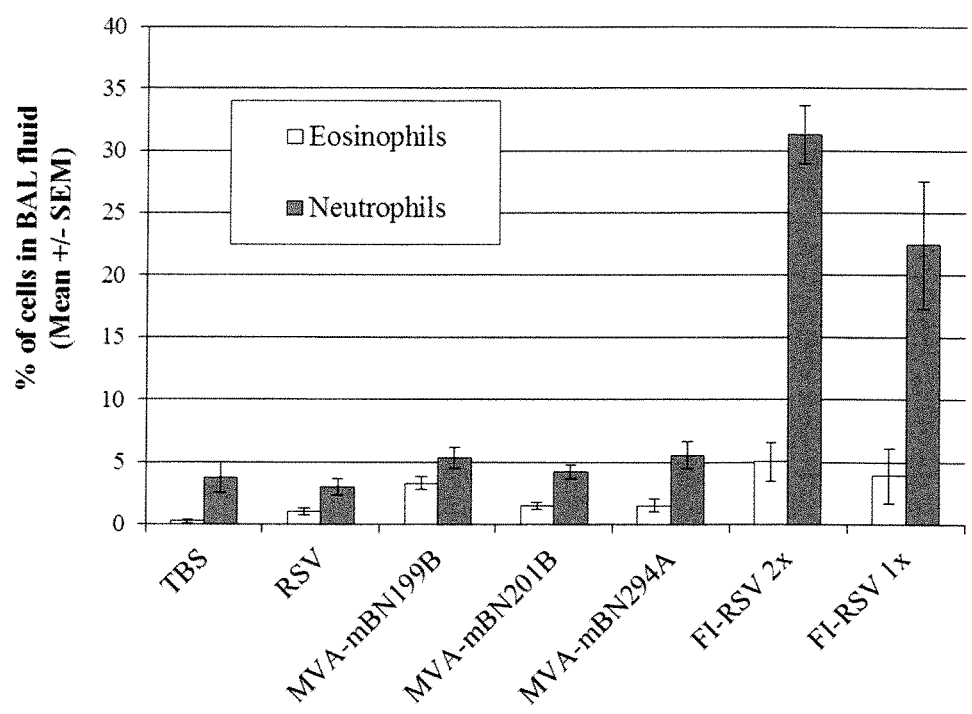
FIG. 18 shows eosinophil and neutrophil infiltrations in bronchoalveolar lavage (BAL) fluids 4 days post RSV(A2) challenge. Mice were immunized s.c. twice 3 weeks apart with TBS or $1\times108$ TCID50 of either MVA-mBN199B, MVA-mBN201B or MVA-mBN294A. Control mice were immunized twice i.n. with $10^6$ pfu RSV or i.m. with 50 μl FI-RSV. Mice were then challenged with $10^6$ pfu RSV A2. Lungs were washed with 1 ml PBS 4 days later and the percentage of eosinophil and neutrophil in BAL fluid was determined.

RSV Load Measured by Quantitative Real-Time PCR. The RSV load in lung was also analyzed by RT-qPCR (FIG. 17). While RSV was not detected by plaque assay in any of the vaccinated mice, RSV genomes were still detectable in mice immunized s.c. twice with MVA-mBN199B, MVA-mBN201B or MVA-mBN294A. For MVA-mBN199B, the RSV load was 45 times lower compared to the TBS control group. RSV genomes were also detectable for MVA-mBN201B and MVA-mBN294A but the load was strongly reduced compared to MVA-mBN199B, 416 times and 281 times lower compared to the TBS control group, respectively.

Analysis of the Enhanced Disease Signs

In contrast to the batch of FI-RSV used in the experiments described in Example 3, the new batch used in this study did not show any increase of IL-4 or IL-5 production. However we were able with this batch to detect eosinophil and neutrophil infiltrations in the BAL fluid which is the main hallmark of enhanced diseases for FI-RSV. No signs of enhanced diseases were detectable for MVA-mBN199B, MVA-mBN201B, and MVA-mBN294A

DISCUSSION AND CONCLUSIONS

Despite the differences between MVA-mBN294A (equivalent to MVA-mBN294B) and MVA-mBN201B, both induced similar B- and T-cell responses and offer similar protection without inducing enhanced disease. Both constructs induced a better protection than MVA-mBN199B which expressed only antigenic determinants of membrane glycoproteins (F and G).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A recombinant modified vaccinia virus Ankara (MVA) comprising:
   a) a nucleotide sequence encoding an antigenic determinant of a respiratory syncytial virus (RSV) membrane glycoprotein F comprising a nucleotide sequence encoding SEQ ID NO: 6;
   b) a nucleotide sequence encoding an antigenic determinant of a RSV M2 matrix protein; and
   c) a nucleotide sequence encoding an antigenic determinant of a RSV N nucleocapsid protein;
   wherein both the antigenic determinant of the RSV N nucleocapsid and of the RSV M2 matrix protein are encoded by a single open reading frame separated by a self-cleavage protease domain.

2. The recombinant MVA of claim 1, wherein the self-cleaving protease domain is the protease 2A fragment sequence derived from Foot and Mouth Disease Virus.

3. The recombinant MVA of claim 2, wherein the single open reading frame comprises a nucleotide sequence encoding the amino acid sequence of SEQ ID NO: 18.

4. The recombinant MVA of claim 3, wherein the single open reading frame comprises the nucleotide sequence of SEQ ID NO: 17.

5. The recombinant MVA of claim 1 further comprising at least one nucleotide sequence encoding an antigenic determinant of an RSV G membrane glycoprotein.

6. The recombinant MVA of claim 5, wherein the nucleotide sequence encoding an antigenic determinant of the RSV G membrane glycoprotein is from an RSV strain A, strain A2, or strain B.

7. The recombinant MVA of claim 6, wherein the nucleotide sequence encoding an antigenic determinant of the RSV G membrane glycoprotein is from an RSV strain A2 or B.

8. The recombinant MVA of claim 7, wherein the nucleotide sequence encoding an antigenic determinant of the RSV G membrane glycoprotein comprises a nucleotide sequence encoding the amino acid sequence of SEQ ID NO: 2.

9. The recombinant MVA of claim 8, wherein the nucleotide sequence encoding an antigenic determinant of the RSV G membrane glycoprotein comprises the nucleotide sequence of SEQ ID NO: 1.

10. The recombinant MVA of claim 9, further comprising an antigenic determinant of a second RSV G membrane glycoprotein.

11. A pharmaceutical composition or vaccine comprising the recombinant MVA of claim 1.

12. The recombinant MVA of claim 10, wherein the nucleotide sequence encoding the antigenic determinant of the second RSV G membrane glycoprotein comprises a nucleotide sequence encoding the amino acid of SEQ ID NO: 8.

13. The recombinant MVA of claim 12, wherein the nucleotide sequence encoding the antigenic determinant of the second RSV G membrane glycoprotein comprises SEQ ID NO: 7.

14. The recombinant MVA of claim 1, wherein both the antigenic determinant of an RSV N nucleocapsid protein and the RSV M2 matrix protein encoded by a single open reading frame separated by a self-cleavage protease domain comprising a nucleotide sequence encoding SEQ ID NO: 10, SEQ ID NO: 12, and SEQ ID No: 14 without the methionine start codon.

15. A recombinant modified vaccinia virus Ankara (MVA) comprising a) at least one nucleotide sequence encoding an antigenic determinant of a respiratory syncytial virus (RSV) membrane glycoprotein F comprising a nucleotide sequence encoding SEQ ID NO:6; b) at least one nucleotide sequence encoding an antigenic determinant of an RSV M2 matrix protein; c) a nucleotide sequence encoding an antigenic determinant of an RSV N nucleocapsid protein, wherein both the antigenic determinant of the RSV N nucleocapsid and of the RSV M2 matrix protein are encoded by a single open reading frame separated by a self-cleavage protease domain; and d) a first and second nucleic acid encoding a first and second RSV G membrane glycoprotein.

16. The recombinant MVA of claim 15, wherein both the antigenic determinant of an RSV N nucleocapsid protein and the RSV M2 matrix protein encoded by a single open reading frame separated by a self-cleavage protease domain comprising a nucleotide sequence encoding SEQ ID NO: 10, SEQ ID NO: 12, and SEQ ID No: 14 without the methionine start codon.

17. The recombinant MVA of claim 16, wherein the first and second nucleic acid encoding a first and second RSV G membrane glycoprotein comprise a nucleic acid encoding SEQ ID NO: 2 and SEQ ID NO: 8, respectively.

18. The recombinant MVA of claim 16, wherein the first and second nucleic acid encoding a first and second RSV G membrane glycoprotein comprise SEQ ID NO:1 and SEQ ID NO: 7, respectively.

* * * * *

SEQUENCE LISTING

```
<160> NUMBER OF SEQ ID NOS: 43

<210> SEQ ID NO 1
<211> LENGTH: 897
<212> TYPE: DNA
<213> ORGANISM: Human Respiratory Syncytial Virus (hRSV), strain A2

<400> SEQUENCE: 1
atgagcaaga acaaggacca gcggaccgcc aagaccctgg aacggacctg ggacaccctg      60
aaccatctgc tgttcatcag tagctgcctg tacaagctga acctgaagtc cgtggcccag     120
atcaccctga gcatcctggc catgatcatc agcaccagcc tgatcattgc cgccatcatc     180
tttatcgcca gcgccaacca caaagtgacc cccaccacag ccatcatcca ggacgccacc     240
tcccagatca agaacaccac ccccacctac ctgacccaga accctcagct gggcatcagc     300
cccagcaacc ccagcgagat caccagccag atcacaacca tcctggcctc caccacccct     360
ggcgtgaagt ccaccctgca gagcaccacc gtgaaaacca agaataccac caccacacag     420
acccagccca gcaagcccac caccaagcag agacagaaca agccccctc caagcccaac     480 aacgacttcc acttcgaggt gttcaacttc gtgcccctgca gcatctgcag caacaacccc     540
acctgttggg ccatctgcaa gcggatcccc aacaagaagc ccggcaagaa aaccacaacc     600
aagcctacca agaagcctac cctgaaaacc accaagaagg accccaagcc ccagaccacc     660
aagagcaaag aggtgccaac caccaagccc accgaggaac ccaccatcaa caccaccaag     720
accaacatca tcaccaccct gctgacctcc aacaccaccg gcaaccccga gctgacaagc     780
cagatggaaa ccttccacag caccagcagc gagggcaacc ctagccctag ccaggtgtcc     840
accacctccg agtacccag ccagcctagc agccccccca cacccccag acagtga         897

<210> SEQ ID NO 2
<211> LENGTH: 298
<212> TYPE: PRT
<213> ORGANISM: hRSV strain A2
```

<400> SEQUENCE: 2

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
130                 135                 140

Lys Pro Thr Thr Lys Gln Arg Gln Asn Lys Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295

<210> SEQ ID NO 3
<211> LENGTH: 1725
<212> TYPE: DNA
<213> ORGANISM: hRSV strain A2

<400> SEQUENCE: 3
atggaactgc tgatcctgaa ggccaacgcc atcaccacaa tcctgaccgc cgtgaccttc     60
tgcttcgcca gcggccagaa catcaccgag gaattctacc agagcacctg tagcgccgtg    120
agcaagggct acctgagcgc cctgagaacc ggctggtaca cctccgtgat caccatcgag    180
ctgtccaaca tcaaagaaaa caagtgcaac ggcaccgacg ccaaagtgaa gctgatcaag    240
caggaactgg acaagtacaa gaacgccgtg accgaactcc agctcctcat gcagtccacc    300
cctgccacca caaccgggc cagaagagaa ctgccccggt ttatgaacta cacactgaac    360

```
aacgccaaaa agaccaatgt cactctgagc aagaagcgga agcggcggtt cctgggcttt      420
ctgctgggcg tgggcagcgc cattgccagc ggcgtggccg tgtccaaggt gctgcacctg      480
gaaggcgaag tgaacaagat caagagtgcc ctgctctcca caaacaaggc cgtggtgtcc      540
ctgagcaacg gcgtgagcgt gctgaccagc aaggtcctgg atctgaagaa ctacatcgac      600
aagcagctcc tgcccatcgt gaacaagcag agctgcagca tcagcaacat cgagactgtc      660
atcgagttcc agcagaagaa caaccggctg ctggaaatca cccgggagtt cagcgtgaac      720
gcaggcgtga ccaccccgt gtccacctac atgctgacca cagcgagct gctgtccctg       780 atcaatgaca tgcccatcac caacgatcag aagaaactca tgagcaacaa cgtgcagatc      840
gtgcggcagc agagttacag tatcatgagc atcatcaaag aagaggtgct ggcctacgtg      900
gtgcagctgc ccctgtacgg cgtgatcgac acccccctgct ggaagctgca caccagcccc    960
ctgtgcacca ccaacacaaa agagggcagt aacatctgcc tgacccggac cgacagaggc     1020
tggtactgcg acaacgccgg cagcgtgtca ttctttccac aggccgagac atgcaaggtg     1080
cagagcaacc gggtgttctg cgacaccatg aacagcctga ccctgcccct cgaagtcaac     1140
ctgtgcaacg tggacatctt caaccccaag tacgactgca agatcatgac ttccaagacc     1200
gacgtgtcca gcagcgtgat tacctccctg ggcgccatcg tgtcctgcta cggcaagacc     1260
aagtgcaccg ccagcaacaa gaatagagga atcatcaaga ccttcagcaa cggctgcgac     1320
tacgtgtcca ataagggcat ggacaccgtg tccgtgggca cacactgta ctacgtgaat     1380 aagcaggaag gcaagagcct gtacgtgaag ggcgagccca tcatcaactt ctacgacccc     1440
ctggtgttcc ccagcgacga gttcgacgcc agtatcagcc aggtcaacga gaagatcaac     1500
cagagcctgg ccttcatcag aaagagcgac gaactgctgc acaatgtgaa cgctggcaag     1560
agtaccacaa acatcatgat caccaccatc atcatcgtga tcattgtgat cctgctgagt     1620
ctgatcgccg tgggcctgct gctgtactgc aaggcccgca gcaccctgt gaccctgtcc      1680 aaggatcagc tgtccggcat caacaatatc gccttctcca actga                     1725

<210> SEQ ID NO 4
<211> LENGTH: 574
<212> TYPE: PRT
<213> ORGANISM: hRSV strain A2

<400> SEQUENCE: 4

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
```

```
            130                 135                 140
Gly Ser Ala Ile Ala Ser Gly Val Ala Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Met Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560
```

Lys Asp Gln Leu Ser Gly Ile Asn Asn Ile Ala Phe Ser Asn
            565                 570

<210> SEQ ID NO 5
<211> LENGTH: 1725
<212> TYPE: DNA
<213> ORGANISM: hRSV strain A-Long

<400> SEQUENCE: 5
atggaactgc ccatcctgaa ggccaacgcc atcaccacaa tcctggccgc cgtgaccttc      60
tgcttcgcca gcagccagaa catcaccgag gaattctacc agagcacctg tagcgccgtg     120
agcaagggct acctgagcgc cctgagaacc ggctggtaca cctccgtgat caccatcgag     180
ctgtccaaca tcaaagaaaa caagtgcaac ggcaccgacg ccaaagtgaa gctgatcaag     240
caggaactgg acaagtacaa gaacgccgtg accgaactcc agctcctcat gcagtccacc     300
cctgccgcca caaccggggc agaagagaa ctgccccggt ttatgaacta cacactgaac     360
aacaccaaaa agaccaatgt gacccggagc aagaagcgga gcggcggtt cctgggcttt     420
ctgctgggcg tgggcagcgc cattgccagc ggcattgccg tgtccaaggt gctgcacctg     480
gaaggcgaag tgaacaagat caagagcgcc ctgctgtcca ccaacaaggc cgtggtgtcc     540
ctgagcaacg gcgtgagcgt gctgaccagc aaggtgctgg atctgaagaa ctacatcgac     600
aagcagctcc tgcccatcgt gaacaagcag agctgccgga tcagcaacat cgagacagtg     660
atcgagttcc agcagaagaa caaccggctg ctggaaatca cccgggagtt cagcgtgaac     720
gtgggcgtga ccacccccgt gtccacctac atgctgacca cagcgagct gctgtccctg     780
atcaatgaca tgcccatcac caacgaccag aagaaactga tgagcaacaa cgtgcagatc     840
gtgcggcagc agagctacag catcatgagc atcatcaaag aagaggtgct ggcctacgtg     900
gtgcagctgc ccctgtacgg cgtgatcgac acccctgct ggaagctgca caccagcccc     960
ctgtgcacca ccaacacaaa agagggcagt aacatctgcc tgacccggac cgacagaggc    1020
tggtactgcg acaacgccgg cagcgtgtca ttctttccac aggccgagac atgcaaggtg    1080
cagagcaacc gggtgttctg cgacaccatg aacagcctga ccctgccctc cgaagtcaac    1140
ctgtgcaacg tggacatctt caaccccaag tacgactgca agatcatgac ttccaagacc    1200
gacgtgtcca gcagcgtgat tacctccctg ggcgccatcg tgtcctgcta cggcaagacc    1260
aagtgcaccg ccagcaacaa gaatagagga atcatcaaga ccttcagcaa cggctgcgac    1320
tacgtgtcca ataagggcgt ggacaccgtg tccgtgggca acacactgta ctacgtgaat    1380
aagcaggaag gcaagagcct gtacgtgaag ggcgagccca tcatcaactt ctacgacccc    1440
ctggtgttcc ccagcgacga gttcgacgcc agcatcagcc aggtcaacga gaagatcaac    1500
cagagcctgg ccttcatcag aaagagcgac gaactgctgc acaatgtgaa cgctggcaag    1560
agtaccacaa acatcatgat caccaccatc atcatcgtga tcattgtgat cctgctgagt    1620
ctgatcgccg tgggcctgct gctgtactgc aaggcccgca gcacccctgt gaccctgtcc    1680
aaggatcagc tgtccggcat caacaatatc gccttctcca actga                    1725

<210> SEQ ID NO 6
<211> LENGTH: 574
<212> TYPE: PRT
<213> ORGANISM: hRSV strain A-Long

<400> SEQUENCE: 6

Met Glu Leu Pro Ile Leu Lys Ala Asn Ala Ile Thr Thr Ile Leu Ala

```
1               5                   10                  15
Ala Val Thr Phe Cys Phe Ala Ser Ser Gln Asn Ile Thr Glu Glu Phe
                20                  25                  30
Tyr Gln Ser Thr Cys Ser Ala Val Ser Lys Gly Tyr Leu Ser Ala Leu
                35                  40                  45
Arg Thr Gly Trp Tyr Thr Ser Val Ile Thr Ile Glu Leu Ser Asn Ile
        50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Ala Asn Asn Arg Ala Arg Arg Glu Leu Pro
                100                 105                 110
Arg Phe Met Asn Tyr Thr Leu Asn Asn Thr Lys Lys Thr Asn Val Thr
                115                 120                 125
Leu Ser Lys Lys Arg Lys Arg Arg Phe Leu Gly Phe Leu Leu Gly Val
        130                 135                 140
Gly Ser Ala Ile Ala Ser Gly Ile Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
        195                 200                 205
Lys Gln Ser Cys Arg Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Val Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
```

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 7
<211> LENGTH: 738
<212> TYPE: DNA
<213> ORGANISM: hRSV strain B

<400> SEQUENCE: 7

```
atgattattt ccactagtct cattatcgct gctattatct tcatcattag tgccaatcat      60
aaagtcaccc tcacaaccgt caccgtgcag accattaaaa accataccga aagaatatc     120
tcaacatatc tgacacaggt ccccccgaa agagtgaact cttccaaaca gcccacaacc     180
acctccccca ttcataccaa tagtgccaca atttctccca cacaaagtc tgaaacacac     240
cacactactg ctcagacaaa gggccgaatc accacctcta ctcagaccaa taagccatca     300
acaaaatccc gctccaaaaa cccacctaaa aaacctaaag atgactatca tttcgaagtc     360
tttaatttcg tcccatgttc catttgcgga acaaccagc tctgtaaatc tatctgtaaa     420
accatcccct ctaacaagcc aaaaaagaaa cctactatta aaccaactaa taagcccacc     480
actaagacta ctaacaaacg cgatccaaaa acacccgcca aatgcctaa aaagagatc     540
attacaaacc cagccaagaa accaactctc aaaactaccg aacgggacac ctccattct     600
cagtctaccg tgctcgatac catcactccc aaatacacta ccagcagca gtcactccac     660
tcaacaacct ccgagaacac ccctcctca acccagattc ctactgcttc cgaaccatc     720
accctcaacc ccaattga                                                  738
```

<210> SEQ ID NO 8
<211> LENGTH: 245
<212> TYPE: PRT
<213> ORGANISM: hRSV strain B

<400> SEQUENCE: 8

Met Ile Ile Ser Thr Ser Leu Ile Ile Ala Ala Ile Ile Phe Ile Ile
1               5                   10                  15

Ser Ala Asn His Lys Val Thr Leu Thr Thr Val Thr Val Gln Thr Ile
                20                  25                  30

Lys Asn His Thr Glu Lys Asn Ile Ser Thr Tyr Leu Thr Gln Val Pro
            35                  40                  45

```
Pro Glu Arg Val Asn Ser Ser Lys Gln Pro Thr Thr Thr Ser Pro Ile
    50                  55                  60
His Thr Asn Ser Ala Thr Ile Ser Pro Asn Thr Lys Ser Glu Thr His
 65                  70                  75                  80
His Thr Thr Ala Gln Thr Lys Gly Arg Ile Thr Thr Ser Thr Gln Thr
                 85                  90                  95
Asn Lys Pro Ser Thr Lys Ser Arg Ser Lys Asn Pro Pro Lys Lys Pro
            100                 105                 110
Lys Asp Asp Tyr His Phe Glu Val Phe Asn Phe Val Pro Cys Ser Ile
                115                 120                 125
Cys Gly Asn Asn Gln Leu Cys Lys Ser Ile Cys Lys Thr Ile Pro Ser
    130                 135                 140
Asn Lys Pro Lys Lys Lys Pro Thr Ile Lys Pro Thr Asn Lys Pro Thr
145                 150                 155                 160
Thr Lys Thr Thr Asn Lys Arg Asp Pro Lys Thr Pro Ala Lys Met Pro
                165                 170                 175
Lys Lys Glu Ile Ile Thr Asn Pro Ala Lys Lys Pro Thr Leu Lys Thr
            180                 185                 190
Thr Glu Arg Asp Thr Ser Ile Ser Gln Ser Thr Val Leu Asp Thr Ile
                195                 200                 205
Thr Pro Lys Tyr Thr Ile Gln Gln Gln Ser Leu His Ser Thr Thr Ser
    210                 215                 220
Glu Asn Thr Pro Ser Ser Thr Gln Ile Pro Thr Ala Ser Glu Pro Ser
225                 230                 235                 240
Thr Leu Asn Pro Asn
            245

<210> SEQ ID NO 9
<211> LENGTH: 1176
<212> TYPE: DNA
<213> ORGANISM: hRSV strain A2

<400> SEQUENCE: 9
atggccctga gcaaagtgaa gctgaacgac accctgaaca aggaccagct gctgtccagc      60
tccaagtaca ccatccagag aagcaccggc gacagcatcg acacccccaa ctacgacgtg     120
cagaagcaca tcaataagct gtgcggcatg ctgctgatca ccgaggacgc caaccacaag     180
ttcaccggcc tgatcgggat gctgtacgcc atgagccggc tgggccggga ggacaccatc     240
aagatcctgc gggacgccgg ctaccacgtg aaggccaacg gcgtggacgt gaccacccac     300
cggcaggaca tcaacggcaa agaaatgaag ttcgaggtgc tgaccctggc cagcctgacc     360
accgagatcc agatcaacat cgagatcgag agccggaagt cctacaagaa aatgctgaaa     420
gaaatgggcg aggtggcccc cgagtacaga acgacagcc cgactgcgg catgatcatc     480 ctgtgtatcg ccgccctggt catcacaaag ctggccgctg cgacagatc tggcctgacc     540 gccgtgatca cgggccaa caacgtgctg aagaacgaga tgaagcggta caagggcctg     600
ctgcccaagg atatcgccaa cagcttctac gaggtgttcg aaaagcaccc ccacttcatc     660
gacgtgttcg tgcacttcgg cattgcccag agcagcacca gaggcggcag cagagtggag     720
ggcatcttcg ccggcctgtt catgaacgcc tacggcgctg ccaggtcat gctgagatgg     780 ggcgtgctgg ccaagagcgt gaagaacatc atgctgggcc acgccagcgt gcaggccgag     840
atggaacagg tggtggaggt gtacgagtac gcccagaagc tgggcggcga ggccggcttc     900
taccacatcc tgaacaaccc caaggcctcc ctgctgtccc tgacccagtt ccccacctt      960
```

```
agcagcgtgg tgctcggaaa tgcagccgga ctgggcatca tgggcgagta ccgcggcacc      1020
cccagaaacc aggacctgta cgacgccgcc aaggcctacg ccgagcagct gaaagaaaac      1080
ggcgtgatca actacagcgt gctggacctg acagccgagg aactggaagc cattaagcac      1140
cagctgaacc ctaaggacaa cgacgtggag ctgtga                                1176
```

<210> SEQ ID NO 10
<211> LENGTH: 391
<212> TYPE: PRT
<213> ORGANISM: hRSV strain A2

<400> SEQUENCE: 10

```
Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys His Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335
```

```
Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu
385                 390

<210> SEQ ID NO 11
<211> LENGTH: 54
<212> TYPE: DNA
<213> ORGANISM: Foot and Mouth Disease Virus (FMDV)

<400> SEQUENCE: 11
ctgaacttcg atctgctgaa actggccggc gacgtggaaa gcaaccctgg cccc        54

<210> SEQ ID NO 12
<211> LENGTH: 18
<212> TYPE: PRT
<213> ORGANISM: FMDV

<400> SEQUENCE: 12

Leu Asn Phe Asp Leu Leu Lys Leu Ala Gly Asp Val Glu Ser Asn Pro
1               5                   10                  15

Gly Pro

<210> SEQ ID NO 13
<211> LENGTH: 585
<212> TYPE: DNA
<213> ORGANISM: hRSV strain A2

<400> SEQUENCE: 13
atgagcagac ggaacccctg caagttcgag atccggggcc actgcctgaa cggcaagcgg     60
tgccacttca gccacaacta cttcgagtgg ccccctcatg ctctgctggt ccggcagaac    120
tttatgctga accggatcct gaagtccatg gacaagagca tcgataccct gagcgagatc    180
agcggagccg ccgaactgga tagaaccgag gaatacgccc tgggcgtggt cggagtgctg    240
gaaagctaca tcggcagcat caacaacatc accaagcaga gcgcctgcgt ggccatgagc    300
aagctgctga ccgagctgaa cagcgacgat atcaagaagc tgcgcgacaa cgaagaactg    360
aactccccca gatccggggt gtacaacaca gtgatcagct acattgagag caaccggaag    420
aacaacaagc agaccatcca tctgctgaag cggctgcccg ccgacgtgct gaaaaagacc    480
atcaagaaca ccctggacat ccacaagtcc atcaccatca taaccccaa agaaagcacc     540 gtgtccgaca ccaacgacca cgccaagaac aacgacacca cctga                   585

<210> SEQ ID NO 14
<211> LENGTH: 194
<212> TYPE: PRT
<213> ORGANISM: hRSV strain A2

<400> SEQUENCE: 14

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45
```

```
Ser Met Asp Lys Ser Ile Asp Thr Leu Ser Glu Ile Ser Gly Ala Ala
     50                  55                  60

Glu Leu Asp Arg Thr Glu Glu Tyr Ala Leu Gly Val Val Gly Val Leu
 65                  70                  75                  80

Glu Ser Tyr Ile Gly Ser Ile Asn Asn Ile Thr Lys Gln Ser Ala Cys
                 85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Ser Thr Val Ser Asp Thr Asn Asp His Ala Lys Asn Asn Asp
            180                 185                 190

Thr Thr
```

<210> SEQ ID NO 15
<211> LENGTH: 1575
<212> TYPE: DNA
<213> ORGANISM: hRSV strain A2

<400> SEQUENCE: 15

```
atggaactcc ctattctcaa agccaatgct attactacca ttctcgccgc tgtcaccttt     60
tgtttcgcct cttcccagaa tattaccgaa gagttttacc agtctacctg ttccgccgtc    120
agtaaaggat acctgtccgc cctccgcact ggttggtata ctagtgtcat acaatcgaa     180
ctctcaaata taaagaaaaa taagtgtaat gggaccgatg ctaaagtcaa actcattaaa    240
caagaactcg ataagtataa gaatgctgtc actgagctgc aactgctgat gcagtctaca    300
cccgcagcca ataatcgagc cagacgcgag ctgcctcgct ttatgaatta tactctcaat    360
aatactaaaa agacaaacgt caccctcagt aaaaagcgaa aagacggttt ctcggattc     420
ctcctcggcg tgggctctgc tatcgctagc ggaattgctg tctccaaagt cctccatctg    480
gaagggagg tcaacaaaat taagtctgct ctcctctcta caaacaaagc cgtcgtgtct    540
ctctccaatg gcgtgtctgt gctcacctct aaagtgctcg acctcaaaaa ttacattgat    600
aaacagctgc tccctattgt gaacaaacag tcttgccgca ttagcaatat cgaaaccgtc    660
attgaatttc aacaaagaa taataggctc ctcgaaatta cccgcgaatt ctccgtgaat    720
gtgggagtca caacacctgt ctctacctat atgctcacta actccgaact cctctccctc    780
attaacgata tgcccattac aaatgatcag aaaaaactca tgtctaataa cgtccagatt    840
gtccgccagc agtcttatag cattatgtcc attatcaaag aggaagtcct cgcttacgtc    900
gtccagctcc ctctgtatgg ggtcatcgat acaccttgtt ggaaactcca tacctcccca    960
ctgtgtacaa ccaataccaa agaagggtcc aatatttgcc tgacaagaac cgaccgcggg   1020
tggtactgtg ataatgccgg ctctgtctcc ttttcccccc aggccgaaac ctgtaaagtc   1080
cagtctaatc gagtcttttg cgatactatg aattccctca ccctcccttc agaagtgaat   1140
ctctgtaacg tcgatatttt caaccctaaa tatgattgca aaattatgac cagtaaaact   1200
gacgtgtcct cttccgtcat cacctcccctc ggtgctattg tgtcttgtta cggaaaaact   1260
```

```
aaatgcacgg ctagtaataa gaaccgaggc attattaaga cctttccaa cggctgtgat    1320 tatgtgtcta acaaggcgt ggatactgtc agtgtcggaa atacactcta ctatgtcaac    1380
aaacaggaag ggaaaagtct ctacgtcaaa ggggagccga taatcaattt ttacgatccc    1440
ctcgtctttc cctccgatga atttgatgcc agtatttccc aggtgaacga aaaatcaat    1500 cagtctctcg cttttattag aaaatctgat gaactcctgc ataacgtcaa tgcaggcaaa    1560
agcactacta attga                                                    1575
```

<210> SEQ ID NO 16
<211> LENGTH: 524
<212> TYPE: PRT
<213> ORGANISM: hRSV strain A2

<400> SEQUENCE: 16

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Val Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
```

| | | | | | | | | | | | |
|---|---|---|---|---|---|---|---|---|---|---|---|
| | | 305 | | | 310 | | | 315 | | | 320 |
| Leu | Cys | Thr | Thr | Asn | Thr | Lys | Glu | Gly | Ser | Asn | Ile | Cys | Leu | Thr | Arg |
| | | | | | 325 | | | | | 330 | | | | | 335 |

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn
            515                 520

<210> SEQ ID NO 17
<211> LENGTH: 1809
<212> TYPE: DNA
<213> ORGANISM: Artificial
<220> FEATURE:
<223> OTHER INFORMATION: cDNA encoding fusion protein comprising full-
      length N protein from hRSV strain A2 fused to the protease 2A
      fragment from FMDV fused to full-length M2 protein from hRSV
      strain A2.

<400> SEQUENCE: 17

```
atggccctga gcaaagtgaa gctgaacgac accctgaaca aggaccagct gctgtccagc      60
tccaagtaca ccatccagag aagcaccggc gacagcatcg acacccccaa ctacgacgtg     120
cagaagcaca tcaataagct gtgcggcatg ctgctgatca ccgaggacgc caaccacaag     180
ttcaccggcc tgatcgggat gctgtacgcc atgagccggc tgggccggga ggacaccatc     240
aagatcctgc gggacgccgg ctaccacgtg aaggccaacg gcgtggacgt gaccacccac     300
cggcaggaca tcaacggcaa agaaatgaag ttcgaggtgc tgaccctggc cagcctgacc     360
accgagatcc agatcaacat cgagatcgag agccggaagt cctacaagaa aatgctgaaa     420
gaaatgggcg aggtggcccc cgagtacaga cacgacagcc ccgactgcgg catgatcatc     480
ctgtgtatcg ccgccctggt catcacaaag ctggccgctg cgacagatc tggcctgacc     540 gccgtgatca gacgggccaa caacgtgctg aagaacgaga tgaagcggta caagggcctg     600
ctgcccaagg atatcgccaa cagcttctac gaggtgttcg aaaagcaccc ccacttcatc     660
gacgtgttcg tgcacttcgg cattgcccag agcagccacg aggcggcag cagagtggag     720 ggcatcttcg ccggcctgtt catgaacgcc tacggcgctg ccaggtcat gctgagatgg     780
```

-continued

```
ggcgtgctgg ccaagagcgt gaagaacatc atgctgggcc acgccagcgt gcaggccgag    840
atggaacagg tggtggaggt gtacgagtac gcccagaagc tgggcggcga ggccggcttc    900
taccacatcc tgaacaaccc caaggcctcc ctgctgtccc tgacccagtt ccccccacttt    960 agcagcgtgg tgctcggaaa tgcagccgga ctgggcatca tgggcgagta ccgcggcacc   1020
cccagaaacc aggacctgta cgacgccgcc aaggcctacg ccgagcagct gaaagaaaac   1080
ggcgtgatca actacagcgt gctggacctg acagccgagg aactggaagc cattaagcac   1140
cagctgaacc ctaaggacaa cgacgtggag ctgctgaact tcgatctgct gaaactggcc   1200
ggcgacgtgg aaagcaaccc tggccccagc agacggaacc cctgcaagtt cgagatccgg   1260
ggccactgcc tgaacggcaa gcggtgccac ttcagccaca actacttcga gtggcccct    1320 catgctctgc tggtccggca gaactttatg ctgaaccgga tcctgaagtc catggacaag   1380
agcatcgata ccctgagcga gatcagcgga gccgccgaac tggatagaac cgaggaatac   1440
gccctgggcg tggtcggagt gctggaaagc tacatcggca gcatcaacaa catcaccaag   1500
cagagcgcct gcgtggccat gagcaagctg ctgaccgagc tgaacagcga cgatatcaag   1560
aagctgcgcg acaacgaaga actgaactcc cccaagatcc gggtgtacaa cagtgatc     1620 agctacattg agagcaaccg gaagaacaac aagcagacca tccatctgct gaagcggctg   1680
cccgccgacg tgctgaaaaa gaccatcaag aacaccctgg acatccacaa gtccatcacc   1740
atcaataacc ccaaagaaag caccgtgtcc gacaccaacg accacgccaa gaacaacgac   1800
accacctga                                                            1809
```

<210> SEQ ID NO 18
<211> LENGTH: 602
<212> TYPE: PRT
<213> ORGANISM: Artificial
<220> FEATURE:
<223> OTHER INFORMATION: Fusion protein comprising full-length N protein
      from hRSV strain A2 fused to the protease 2A fragment from FMDV
      fused to full-length M2 protein from hRSV strain A2.

<400> SEQUENCE: 18

```
Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160
```

```
Leu Cys Ile Ala Ala Leu Val Ile Thr Lys Leu Ala Ala Gly Asp Arg
            165                 170                 175

Ser Gly Leu Thr Ala Val Ile Arg Arg Ala Asn Asn Val Leu Lys Asn
        180                 185                 190

Glu Met Lys Arg Tyr Lys Gly Leu Leu Pro Lys Asp Ile Ala Asn Ser
            195                 200                 205

Phe Tyr Glu Val Phe Glu Lys His Pro His Phe Ile Asp Val Phe Val
        210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
            245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Glu Val Tyr
        275                 280                 285

Glu Tyr Ala Gln Lys Leu Gly Gly Glu Ala Gly Phe Tyr His Ile Leu
        290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu Leu Asn Phe Asp Leu Leu Lys Leu Ala
385                 390                 395                 400

Gly Asp Val Glu Ser Asn Pro Gly Pro Ser Arg Arg Asn Pro Cys Lys
            405                 410                 415

Phe Glu Ile Arg Gly His Cys Leu Asn Gly Lys Arg Cys His Phe Ser
        420                 425                 430

His Asn Tyr Phe Glu Trp Pro Pro His Ala Leu Leu Val Arg Gln Asn
    435                 440                 445

Phe Met Leu Asn Arg Ile Leu Lys Ser Met Asp Lys Ser Ile Asp Thr
    450                 455                 460

Leu Ser Glu Ile Ser Gly Ala Ala Glu Leu Asp Arg Thr Glu Glu Tyr
465                 470                 475                 480

Ala Leu Gly Val Val Gly Val Leu Glu Ser Tyr Ile Gly Ser Ile Asn
            485                 490                 495

Asn Ile Thr Lys Gln Ser Ala Cys Val Ala Met Ser Lys Leu Leu Thr
        500                 505                 510

Glu Leu Asn Ser Asp Ile Lys Lys Leu Arg Asp Asn Glu Glu Leu
        515                 520                 525

Asn Ser Pro Lys Ile Arg Val Tyr Asn Thr Val Ile Ser Tyr Ile Glu
    530                 535                 540

Ser Asn Arg Lys Asn Asn Lys Gln Thr Ile His Leu Leu Lys Arg Leu
545                 550                 555                 560

Pro Ala Asp Val Leu Lys Lys Thr Ile Lys Asn Thr Leu Asp Ile His
            565                 570                 575

Lys Ser Ile Thr Ile Asn Asn Pro Lys Glu Ser Thr Val Ser Asp Thr
```

-continued

```
               580                 585                 590
Asn Asp His Ala Lys Asn Asn Asp Thr Thr
        595                 600

<210> SEQ ID NO 19
<211> LENGTH: 10
<212> TYPE: PRT
<213> ORGANISM: Artificial
<220> FEATURE:
<223> OTHER INFORMATION: Synthetic peptide.

<400> SEQUENCE: 19

Thr Tyr Met Leu Thr Asn Ser Glu Leu Leu
1               5                   10

<210> SEQ ID NO 20
<211> LENGTH: 9
<212> TYPE: PRT
<213> ORGANISM: Artificial
<220> FEATURE:
<223> OTHER INFORMATION: Synthetic peptide.

<400> SEQUENCE: 20

Lys Tyr Lys Asn Ala Val Thr Glu Leu
1               5

<210> SEQ ID NO 21
<211> LENGTH: 15
<212> TYPE: PRT
<213> ORGANISM: Artificial
<220> FEATURE:
<223> OTHER INFORMATION: Synthetic peptide.

<400> SEQUENCE: 21

Glu Leu Gln Leu Leu Met Gln Ser Thr Pro Ala Ala Asn Asn Arg
1               5                   10                  15

<210> SEQ ID NO 22
<211> LENGTH: 13
<212> TYPE: PRT
<213> ORGANISM: Artificial
<220> FEATURE:
<223> OTHER INFORMATION: Synthetic peptide.

<400> SEQUENCE: 22

Trp Ala Ile Cys Lys Arg Ile Pro Asn Lys Lys Pro Gly
1               5                   10

<210> SEQ ID NO 23
<211> LENGTH: 9
<212> TYPE: PRT
<213> ORGANISM: Artificial
<220> FEATURE:
<223> OTHER INFORMATION: Synthetic peptide.

<400> SEQUENCE: 23

Lys Tyr Thr Ile Gln Arg Ser Thr Gly
1               5

<210> SEQ ID NO 24
<211> LENGTH: 9
<212> TYPE: PRT
<213> ORGANISM: Artificial
<220> FEATURE:
<223> OTHER INFORMATION: Synthetic peptide.

<400> SEQUENCE: 24
```

```
Leu Ser Leu Thr Gln Phe Pro Asn Phe
1               5
```

<210> SEQ ID NO 25
<211> LENGTH: 9
<212> TYPE: PRT
<213> ORGANISM: Artificial
<220> FEATURE:
<223> OTHER INFORMATION: Synthetic peptide.

<400> SEQUENCE: 25

```
Ser Arg Leu Gly Arg Glu Asp Thr Ile
1               5
```

<210> SEQ ID NO 26
<211> LENGTH: 9
<212> TYPE: PRT
<213> ORGANISM: Artificial
<220> FEATURE:
<223> OTHER INFORMATION: Synthetic peptide.

<400> SEQUENCE: 26

```
Ile Pro Lys Asp Ile Ala Asn Ser Phe
1               5
```

<210> SEQ ID NO 27
<211> LENGTH: 9
<212> TYPE: PRT
<213> ORGANISM: Artificial
<220> FEATURE:
<223> OTHER INFORMATION: Synthetic peptide.

<400> SEQUENCE: 27

```
Ser Tyr Ile Gly Ser Ile Asn Asn Ile
1               5
```

<210> SEQ ID NO 28
<211> LENGTH: 1725
<212> TYPE: DNA
<213> ORGANISM: hRSV strain A2

<400> SEQUENCE: 28

```
atggagttgc taatcctcaa agcaaatgca attaccacaa tcctcactgc agtcacattt      60
tgttttgctt ctggtcaaaa catcactgaa gaatttatc  aatcaacatg cagtgcagtt     120
agcaaaggct atcttagtgc tctgagaact ggttggtata ccagtgttat aactatagaa     180
ttaagtaata tcaaggaaaa taagtgtaat ggaacagatg ctaaggtaaa attgataaaa     240
caagaattag ataaatataa aaatgctgta acagaattgc agttgctcat gcaaagcaca     300
ccaccaacaa acaatcgagc cagaagagaa ctaccaaggt ttatgaatta tacactcaac     360
aatgccaaaa aaaccaatgt aacattaagc aagaaaagga aagaagatt  tcttggtttt     420
ttgttaggtg ttggatctgc aatcgccagt ggcgttgctg tatctaaggt cctgcaccta     480
gaagggaag  tgaacaagat caaaagtgct ctactatcca caacaaggc  tgtagtcagc     540
ttatcaaatg gagttagtgt cttaaccagc aaagtgttag acctcaaaaa ctatatagat     600
aaacaattgt tacctattgt gaacaagcaa agctgcagca tatcaaatat agaaactgtg     660
atagagttcc aacaaaagaa caacagacta ctagagatta ccagggaatt tagtgttaat     720
gcaggtgtaa ctacacctgt aagcacttac atgttaacta atagtgaatt attgtcatta     780
atcaatgata tgcctataac aaatgatcag aaaaagttaa tgtccaacaa tgttcaaata     840
```

```
gttagacagc aaagttactc tatcatgtcc ataataaaag aggaagtctt agcatatgta      900
gtacaattac cactatatgg tgttatagat acaccctgtt ggaaactaca cacatcccct      960
ctatgtacaa ccaacacaaa agaagggtcc aacatctgtt taacaagaac tgacagagga     1020
tggtactgtg acaatgcagg atcagtatct ttcttcccac aagctgaaac atgtaaagtt     1080
caatcaaatc gagtattttg tgacacaatg aacagtttaa cattaccaag tgaaataaat     1140
ctctgcaatg ttgacatatt caaccccaaa tatgattgta aaattatgac ttcaaaaaca     1200
gatgtaagca gctccgttat cacatctcta ggagccattg tgtcatgcta tggcaaaact     1260
aaatgtacag catccaataa aaatcgtgga atcataaaga cattttctaa cgggtgcgat     1320
tatgtatcaa ataaagggat ggacactgtg tctgtaggta acacattata ttatgtaaat     1380
aagcaagaag gtaaaagtct ctatgtaaaa ggtgaaccaa taataaattt ctatgaccca     1440
ttagtattcc cctctgatga atttgatgca tcaatatctc aagtcaacga gaagattaac     1500
cagagcctag catttattcg taatcccgat gaattattac ataatgtaaa tgctggtaaa     1560
tccaccacaa atatcatgat aactactata attatatgtga ttatagtaat attgttatca     1620
ttaattgctg ttggactgct cttatactgt aaggccagaa gcacaccagt cacactaagc     1680
aaagatcaac tgagtggtat aaataatatt gcatttagta actaa                      1725
```

<210> SEQ ID NO 29
<211> LENGTH: 574
<212> TYPE: PRT
<213> ORGANISM: hRSV strain A2

<400> SEQUENCE: 29

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Met Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 30
<211> LENGTH: 897
<212> TYPE: DNA
<213> ORGANISM: hRSV strain A2

<400> SEQUENCE: 30
atgagcaaga acaaggacca gcggaccgcc aagaccctgg aacggacctg ggacaccctg     60
aaccatctgc tgttcatcag tagctgcctg tacaagctga acctgaagtc cgtggcccag     120

-continued

```
atcaccctga gcatcctggc catgatcatc agcaccagcc tgatcattgc cgccatcatc      180
tttatcgcca cgccaacca caaagtgacc cccaccacag ccatcatcca ggacgccacc      240
tcccagatca agaacaccac ccccacctac ctgacccaga ccctcagct gggcatcagc      300
cccagcaacc ccagcgagat caccagccag atcacaacca tcctggcctc caccacccct      360
ggcgtgaagt ccaccctgca gagcaccacc gtgaaaacca gaataccac caccacacag      420
acccagccca gcaagcccac caccaagcag agacagaaca gcccccctc caagcccaac      480
aacgacttcc acttcgaggt gttcaacttc gtgccctgca gcatctgcag caacaacccc      540
acctgttggg ccatctgcaa gcggatcccc aacaagaagc ccggcaagaa aaccacaacc      600
aagcctacca agaagcctac cctgaaaacc accaagaagg accccaagcc ccagaccacc      660
aagagcaaag aggtgccaac caccaagccc accgaggaac ccaccatcaa caccaccaag      720
accaacatca tcaccaccct gctgacctcc aacaccaccg caaccccga gctgacaagc      780
cagatggaaa ccttccacag caccagcagc gagggcaacc ctagccctag ccaggtgtcc      840
accacctccg agtaccccag ccagcctagc agccccccca cacccccag acagtga         897
```

<210> SEQ ID NO 31
<211> LENGTH: 298
<212> TYPE: PRT
<213> ORGANISM: hRSV strain A2

<400> SEQUENCE: 31

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240
```

Thr Asn Ile Ile Thr Thr Leu Leu Thr Ser Asn Thr Thr Gly Asn Pro
            245                 250                 255

Glu Leu Thr Ser Gln Met Glu Thr Phe His Ser Thr Ser Glu Gly
    260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
        290                 295

<210> SEQ ID NO 32
<211> LENGTH: 585
<212> TYPE: DNA
<213> ORGANISM: hRSV strain A2

<400> SEQUENCE: 32
atgtcacgaa ggaatccttg caaatttgaa attcgaggtc attgcttaaa tggtaagagg     60
tgtcatttta gtcataatta ttttgaatgg ccaccccatg cactgcttgt aagacaaaac    120
tttatgttaa acagaatact taagtctatg gataaaagta tagatacctt atcagaaata    180
agtggagctg cagagttgga cagaacagaa gagtatgctc ttggtgtagt tggagtgcta    240
gagagttata taggatcaat aaacaatata actaaacaat cagcatgtgt tgccatgagc    300
aaactcctca ctgaactcaa tagtgatgat atcaaaaagc tgagggacaa tgaagagcta    360
aattcaccca gataagagt gtacaatact gtcatatcat atattgaaag caacaggaaa    420 acaataaac aaactatcca tctgttaaaa agattgccag cagacgtatt gaagaaaacc    480
atcaaaaaca cattggatat ccataagagc ataaccatca caacccaaa agaatcaact    540 gttagtgata caaatgacca tgccaaaaat aatgatacta cctga                   585

<210> SEQ ID NO 33
<211> LENGTH: 194
<212> TYPE: PRT
<213> ORGANISM: hRSV strain A2

<400> SEQUENCE: 33

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro 165                 170                 175
Lys Glu Ser Thr Val Ser Asp Thr Asn Asp His Ala Lys Asn Asn Asp
            180                 185                 190

Thr Thr

<210> SEQ ID NO 34
<211> LENGTH: 1176
<212> TYPE: DNA
<213> ORGANISM: hRSV strain A2

<400> SEQUENCE: 34

| | | | | | |
|---|---|---|---|---|---|
| atggctctta | gcaaagtcaa | gttgaatgat | acactcaaca | agatcaact | tctgtcatcc | 60 |
| agcaaataca | ccatccaacg | gagcacagga | gatagtattg | atactcctaa | ttatgatgtg | 120 |
| cagaaacaca | tcaataagtt | atgtggcatg | ttattaatca | cagaagatgc | taatcataaa | 180 |
| ttcactgggt | taataggtat | gttatatgcg | atgtctaggt | taggaagaga | agacaccata | 240 |
| aaaatactca | gagatgcggg | atatcatgta | aaagcaaatg | gagtagatgt | aacaacacat | 300 |
| cgtcaagaca | ttaatggaaa | agaaatgaaa | tttgaagtgt | taacattggc | aagcttaaca | 360 |
| actgaaattc | aaatcaacat | tgagatagaa | tctagaaaat | cctacaaaaa | aatgctaaaa | 420 |
| gaaatgggag | aggtagctcc | agaatacagg | catgactctc | ctgattgtgg | gatgataata | 480 |
| ttatgtatag | cagcattagt | aataactaaa | ttagcagcag | gggacagatc | tggtcttaca | 540 |
| gccgtgatta | ggagagctaa | taatgtccta | aaaaatgaaa | tgaaacgtta | caaaggctta | 600 |
| ctacccaagg | acatagccaa | cagcttctat | gaagtgtttg | aaaaacatcc | ccactttata | 660 |
| gatgttttg | ttcattttgg | tatagcacaa | tcttctacca | gaggtggcag | tagagttgaa | 720 |
| gggattttg | caggattgtt | tatgaatgcc | tatggtgcag | ggcaagtgat | gttacgtggg | 780 |
| ggagtcttag | caaaatcagt | taaaaatatt | atgttaggac | atgctagtgt | gcaagcagaa | 840 |
| atggaacaag | ttgttgaggt | ttatgaatat | gcccaaaaat | tgggtggtga | agcaggattc | 900 |
| taccatatat | tgaacaaccc | aaaagcatca | ttattatctt | tgactcaatt | tcctcacttc | 960 |
| tccagtgtag | tattaggcaa | tgctgctggc | ctaggcataa | tgggagagta | cagaggtaca | 1020 |
| ccgaggaatc | aagatctata | tgatgcagca | aaggcatatg | ctgaacaact | caaagaaaat | 1080 |
| ggtgtgatta | actacagtgt | actagacttg | acagcagaag | aactagaggc | tatcaaacat | 1140 |
| cagcttaatc | caaaagataa | tgatgtagag | ctttga | | | 1176 |

<210> SEQ ID NO 35
<211> LENGTH: 391
<212> TYPE: PRT
<213> ORGANISM: hRSV strain A2

<400> SEQUENCE: 35

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp

```
                    85                  90                  95
Val Thr Thr His Arg Gln Asp Ile Asn Gly Lys Glu Met Lys Phe Glu
                100                 105                 110

Val Leu Thr Leu Ala Ser Leu Thr Thr Glu Ile Gln Ile Asn Ile Glu
                115                 120                 125

Ile Glu Ser Arg Lys Ser Tyr Lys Lys Met Leu Lys Glu Met Gly Glu
            130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
                180                 185                 190

Glu Met Lys Arg Tyr Lys Gly Leu Leu Pro Lys Asp Ile Ala Asn Ser
            195                 200                 205

Phe Tyr Glu Val Phe Glu Lys His Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Glu Val Tyr
    275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
        370                 375                 380

Lys Asp Asn Asp Val Glu Leu
385                 390

<210> SEQ ID NO 36
<211> LENGTH: 27
<212> TYPE: DNA
<213> ORGANISM: Artificial
<220> FEATURE:
<223> OTHER INFORMATION: RT-PCR primer.

<400> SEQUENCE: 36
gaactcagtg taggtagaat gtttgca                                      27

<210> SEQ ID NO 37
<211> LENGTH: 25
<212> TYPE: DNA
<213> ORGANISM: Artificial
<220> FEATURE:
<223> OTHER INFORMATION: RT-PCR primer.
```

```
<400> SEQUENCE: 37
ttcagctatc attttctctg ccaat                                          25

<210> SEQ ID NO 38
<211> LENGTH: 27
<212> TYPE: DNA
<213> ORGANISM: Artificial
<220> FEATURE:
<223> OTHER INFORMATION: RT-PCR probe.

<400> SEQUENCE: 38
tttgaacctg tctgaacatt cccggtt                                        27

<210> SEQ ID NO 39
<211> LENGTH: 40
<212> TYPE: DNA
<213> ORGANISM: Artificial
<220> FEATURE:
<223> OTHER INFORMATION: Synthetic promoter.

<400> SEQUENCE: 39
aaaaattgaa attttatttt tttttttttgg aatataaata                         40

<210> SEQ ID NO 40
<211> LENGTH: 104
<212> TYPE: DNA
<213> ORGANISM: Artificial
<220> FEATURE:
<223> OTHER INFORMATION: Synthetic promoter.

<400> SEQUENCE: 40
tccaaaccca cccgcttttt atagtaagtt tttcacccat aaataataaa tacaataatt    60
aatttctcgt aaaagtagaa aatatattct aatttattgc acgg                    104

<210> SEQ ID NO 41
<211> LENGTH: 73
<212> TYPE: DNA
<213> ORGANISM: Artificial
<220> FEATURE:
<223> OTHER INFORMATION: Synthetic promoter.

<400> SEQUENCE: 41
taaaaattga aaaatatttc taatttatag gacggttttg attttctttt tttctattct    60
ataaataata aat                                                      73

<210> SEQ ID NO 42
<211> LENGTH: 227
<212> TYPE: DNA
<213> ORGANISM: Artificial
<220> FEATURE:
<223> OTHER INFORMATION: Synthetic promoter.

<400> SEQUENCE: 42
gttttgaaaa tttttttata ataaatatcc ggtaaaaatt gaaaaactat tctaatttat    60
tgcacggtcc ggtaaaaatt gaaaaactat tctaatttat tgcacggtcc ggtaaaaatt   120
gaaaaactat tctaatttat tgcacggtcc ggtaaaaatt gaaaaactat tctaatttat   180
tgcacggtcc ggtaaaaatt gaaaaactat tctaatttat tgcacgg                227

<210> SEQ ID NO 43
<211> LENGTH: 112
<212> TYPE: DNA
<213> ORGANISM: Artificial
```

-continued

```
<220> FEATURE:
<223> OTHER INFORMATION: Synthetic promoter.

<400> SEQUENCE: 43
tacttaaaaa ttgaaaataa atacaaaggt tcttgagggt tgtgttaaat tgaaagcgag      60
aaataatcat aaataatttc attatcgcga tatccgttaa gtttgtatcg ta             112
```